United States Patent
Zhao et al.

(10) Patent No.: US 10,254,283 B2
(45) Date of Patent: Apr. 9, 2019

(54) BIOMARKER FOR MELK ACTIVITY AND METHODS OF USING SAME

(71) Applicant: Dana-Farber Cancer Institute, Inc., Boston, MA (US)

(72) Inventors: Jean Zhao, Brookline, MA (US); Yubao Wang, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/034,955

(22) PCT Filed: Nov. 12, 2014

(86) PCT No.: PCT/US2014/065173
§ 371 (c)(1),
(2) Date: May 6, 2016

(87) PCT Pub. No.: WO2015/073509
PCT Pub. Date: May 21, 2015

(65) Prior Publication Data
US 2016/0291017 A1     Oct. 6, 2016

Related U.S. Application Data

(60) Provisional application No. 61/954,046, filed on Mar. 17, 2014, provisional application No. 61/902,877, filed on Nov. 12, 2013.

(51) Int. Cl.
```
G01N 33/574    (2006.01)
G01N 33/573    (2006.01)
G01N 33/68     (2006.01)
C12Q 1/48      (2006.01)
```

(52) U.S. Cl.
CPC .......... *G01N 33/573* (2013.01); *C12Q 1/485* (2013.01); *G01N 33/5748* (2013.01); *G01N 33/6875* (2013.01); *G01N 2333/47* (2013.01); *G01N 2333/912* (2013.01); *G01N 2500/02* (2013.01)

(58) Field of Classification Search
CPC ..... G01N 33/53; G01N 33/574; G01N 33/573
USPC ........................................ 436/501; 424/133.1
See application file for complete search history.

(56) References Cited

U.S. PATENT DOCUMENTS

| | | | | |
|---|---|---|---|---|
| 2008/0293044 | A1* | 11/2008 | Kadyk ................. | C12Q 1/485 435/6.14 |
| 2011/0212053 | A1* | 9/2011 | Qian ..................... | A61K 31/437 424/85.2 |
| 2013/0217671 | A1 | 8/2013 | Matsuo et al. | |

FOREIGN PATENT DOCUMENTS

| | | |
|---|---|---|
| CN | 103173527 A | 6/2013 |
| WO | WO-2013/045539 A1 | 4/2013 |
| WO | WO-2013/109388 A2 | 7/2013 |

OTHER PUBLICATIONS

Badouel et al., "M-phase MELK Activity is Regulated by MPF and MAPK," Cell Cycle 5:883-889 (2006).
Badouel et al., "Maternal embryonic leucine zipper kinase is stabilized in mitosis by phosphorylation and is partially degraded upon mitotic exit," Exp. Cell Res. 316:2166-2173 (2010).
Canevari et al., "Structural insight into Maternal Embryonic Leucine zipper Kinase (MELK) conformation and inhibition towards structure-based drug design," Biochem. 52:6380-6387 (2013).
Cao et al., "Structural Basis for the Regulation of Maternal Embryonic Leucine Zipper Kinase," PLoS One 8:e70031 (2013).
Chung et al., "Development of an orally-administrative MELK-targeting inhibitor that suppresses the growth of various types of human cancer," Oncotarget 3:1629-1640 (2012).
Hebbard et al., "Maternal Embryonic Leucine Zipper Kinase Is Upregulated and Required in Mammary Tumor-Initiating Cells In vivo," Cancer Res. 70:8863-8873 (2010).
Komatsu et al., "Molecular features of triple negative breast cancer cells by genome-wide gene expression profiling analysis," Int. J. Oncol. 42:478-506 (2013).
Lin et al., "Involvement of maternal embryonic leucine zipper kinase (MELK) in mammary carcinogenesis through interaction with Bcl-G, a pro-apoptotic member of the Bcl-2 Family," Breast Cancer Res. 9:R17 (2007).
Mehta et al., "SP600125 selectively inhibits histone H3-Ser10 phosphorylation," retrieved from the internet dated Dec. 14, 2005, 2015 at <http://www.med.miami.edu/mnbws/documents/06MehtaKamal.pdf> [accessed on Aug. 15, 2015].
Pickard et al., "Dysregulated expression of Fau and MELK is associated with poor prognosis in breast cancer," Breast Cancer Res. 11:R60 (2009).

(Continued)

*Primary Examiner* — Yan Xiao
(74) *Attorney, Agent, or Firm* — Foley Hoag LLP

(57) ABSTRACT

The methods of the present invention, relate to the surprising determination that the level of phosphorylation of position 406 (e.g., a serine residue) of human eukaryotic initiation factor 4B (eIF4B), or a corresponding phosphorylatable amino acid of an ortholog thereof, serves as a biomarker for MELK enzymatic (e.g., kinase) and/or oncogenic activity. The methods of the present invention further relate to the surprising determination that the level of phosphorylation of position 3 (e.g., a threonine residue) and/or position 10 (e.g., a serine residue) and/or position 11 (e.g., a threonine residue) of human Histone M3, or a corresponding phosphorylatable amino acid of an ortholog thereof, also serves as a biomarker for MELK enzymatic (e.g., kinase) and/or oncogenic activity.

18 Claims, 8 Drawing Sheets
Specification includes a Sequence Listing.

(56) References Cited

OTHER PUBLICATIONS

Wang et al., "MELK is an oncogenic kinase essential for mitotic progression in basal-like breast cancer cells," eLife 3:e01763 (2014).
Yang et al., "eIF4B Phosphorylation by Pim Kinases Plays a Critical Role in Cellular Transformation by Abl Oncogenes," Cancer Res. 73:4898-4908 (2013).
International Search Report dated Nov. 12, 2015 from PCT/US2014/065173.
Chung et al., "MELK inhibitor, novel molecular targeted therapeutics for human cancer stem cells," Cell Cycle, 12(11): 1655-1656 (2013).
International Preliminary Report on Patentability dated May 17, 2016, from PCT/US2014/065173.
Nakano et al., "Maternal embryonic leucine zipper kinase is a key regulator of the proliferation of malignant brain tumors, including brain tumor stem cells," J Neurosci Res, 86(1): 48-60 (2008).
Nakano et al., "Siomycin a targets brain tumor stem cells partially through a MELK-mediated pathway," Neuro-Oncology, 13(6): 622-634 (2011).
Partial Supplementary European Search Report issued by the European Patent Office in corresponding International Application No. 14862279.8, dated May 22, 2017.
Wang et al., "Mitotic MELK-eIF4B signaling controls protein synthesis and tumor cell survival," Proc Natl Acad Sci U S A, 113(35): 9810-9815 (2016).
Wenbin et al., "OTSSP167 Abrogates Mitotic Checkpoint through Inhibiting Multiple Mitotic Kinases," PLoS One, 11(4): e0153518 (2016).
Zhang, "Cloning of Pig Maternal Embryonic Leucine Zipper Kinase MELK gene," China Master's Theses Full-text Database, Agricultural Technology Section, D050-56.
Extended European Search Report for European Application No. 14862279.8 dated Aug. 31, 2017.

* cited by examiner c-Myc 5'UTR
or
ODC1 5'UTR

SEQUENCE LISTING

```
<160> NUMBER OF SEQ ID NOS: 45

<210> SEQ ID NO 1
<211> LENGTH: 1956
<212> TYPE: DNA
<213> ORGANISM: Homo sapiens

<400> SEQUENCE: 1
atgaaagatt atgatgaact tctcaaatat tatgaattac atgaaactat tgggacaggt      60
ggctttgcaa aggtcaaact tgcctgccat atccttactg gagagatggt agctataaaa     120
atcatggata aaaacacact agggagtgat ttgccccgga tcaaaacgga gattgaggcc     180
ttgaagaacc tgagacatca gcatatatgt caactctacc atgtgctaga dacagccaac     240
aaaatattca tggttcttga gtactgccct ggaggagagc tgtttgacta tataatttcc     300
caggatcgcc tgtcagaaga ggagacccgg gttgtcttcc gtcagatagt atctgctgtt     360
gcttatgtgc acagccaggg ctatgctcac agggacctca agccagaaaa tttgctgttt     420
gatgaatatc ataaattaaa gctgattgac tttggtctct gtgcaaaacc caagggtaac     480
aaggattacc atctacagac atgctgtggg agtctggctt atgcagcacc tgagttaata     540
caaggcaaat catatcttgg atcagaggca gatgtttgga gcatgggcat actgttatat     600
gttcttatgt gtggatttct accatttgat gatgataatg taatggcttt atacaagaag     660
attatgagag gaaaatatga tgttcccaag tggctctctc ccagtagcat tctgcttctt     720
caacaaatgc tgcaggtgga cccaaagaaa cggatttcta tgaaaaatct attgaaccat     780
ccctggatca tgcaagatta caactatcct gttgagtggc aaagcaagaa tccttttatt     840
cacctcgatg atgattgcgt aacagaactt tctgtacatc acagaaacaa caggcaaaca     900
atggaggatt taatttcact gtggcagtat gatcacctca cggctaccta tcttctgctt     960
ctagccaaga aggctcgggg aaaaccagtt cgtttaaggc tttcttcttt ctcctgtgga    1020
caagccagtg ctaccccatt cacagacatc aagtcaaata attggagtct ggaagatgtg    1080
accgcaagtg ataaaatta tgtggcggga ttaatagact atgattggtg tgaagatgat    1140
ttatcaacag gtgctgctac tcccgaaaca tcacagttta ccaagtactg gacagaatca    1200
aatggggtgg aatctaaatc attaactcca gccttatgca gaacacctgc aaataaatta    1260
aagaacaaag aaaatgtata tactcctaag tctgctgtaa agaatgaaga gtactttatg    1320
tttcctgagc caaagactcc agttaataag aaccagcata agagagaaat actcactacg    1380
ccaaatcgtt acactacacc ctcaaaagct agaaaccagt gcctgaaaga aactccaatt    1440
aaaataccag taaattcaac aggaacagac aagttaatga caggtgtcat tagccctgag    1500
aggcggtgcc gctcagtgga attggatctc aaccaagcac atatggagga gactccaaaa    1560
agaaagggag ccaaagtgtt tgggagcctt gaaaggggggt tggataaggt tatcactgtg    1620
ctcaccagga gcaaaaggaa gggttctgcc agagacgggc ccagaagact aaagcttcac    1680
```

-continued

```
tataacgtga ctacaactag attagtgaat ccagatcaac tgttgaatga aataatgtct   1740
attcttccaa agaagcatgt tgactttgta caaaagggtt atacactgaa gtgtcaaaca   1800
cagtcagatt ttgggaaagt gacaatgcaa tttgaattag aagtgtgcca gcttcaaaaa   1860
cccgatgtgg tgggtatcag gaggcagcgg cttaagggcg atgcctgggt ttacaaaaga   1920
ttagtggaag acatcctatc tagctgcaag gtataa                             1956
```

<210> SEQ ID NO 2
<211> LENGTH: 651
<212> TYPE: PRT
<213> ORGANISM: Homo sapiens

<400> SEQUENCE: 2

```
Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
    50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
        275                 280                 285

Glu Leu Ser Val His His Arg Asn Asn Arg Gln Thr Met Glu Asp Leu
    290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
```

```
                        325                 330                 335
Phe Ser Cys Gly Gln Ala Ser Ala Thr Pro Phe Thr Asp Ile Lys Ser
            340                 345                 350
Asn Asn Trp Ser Leu Glu Asp Val Thr Ala Ser Asp Lys Asn Tyr Val
        355                 360                 365
Ala Gly Leu Ile Asp Tyr Asp Trp Cys Glu Asp Leu Ser Thr Gly
    370                 375                 380
Ala Ala Thr Pro Arg Thr Ser Gln Phe Thr Lys Tyr Trp Thr Glu Ser
385                 390                 395                 400
Asn Gly Val Glu Ser Lys Ser Leu Thr Pro Ala Leu Cys Arg Thr Pro
                405                 410                 415
Ala Asn Lys Leu Lys Asn Lys Glu Asn Val Tyr Thr Pro Lys Ser Ala
            420                 425                 430
Val Lys Asn Glu Glu Tyr Phe Met Phe Pro Gly Pro Lys Thr Pro Val
        435                 440                 445
Asn Lys Asn Gln His Lys Arg Glu Ile Leu Thr Thr Pro Asn Arg Tyr
    450                 455                 460
Thr Thr Pro Ser Lys Ala Arg Asn Gln Cys Leu Lys Glu Thr Pro Ile
465                 470                 475                 480
Lys Ile Pro Val Asn Ser Thr Gly Thr Asp Lys Leu Met Thr Gly Val
                485                 490                 495
Ile Ser Pro Glu Arg Arg Cys Arg Ser Val Glu Leu Asp Leu Asn Gln
            500                 505                 510
Ala His Met Glu Glu Thr Pro Lys Arg Lys Gly Ala Lys Val Phe Gly
        515                 520                 525
Ser Leu Glu Arg Gly Leu Asp Lys Val Ile Thr Val Leu Thr Arg Ser
    530                 535                 540
Lys Arg Lys Gly Ser Ala Arg Asp Gly Pro Arg Arg Leu Lys Leu His
545                 550                 555                 560
Tyr Asn Val Thr Thr Thr Arg Leu Val Asn Pro Asp Gln Leu Leu Asn
                565                 570                 575
Glu Ile Met Ser Ile Leu Pro Lys Lys His Val Asp Phe Val Gln Lys
            580                 585                 590
Gly Tyr Thr Leu Lys Cys Gln Thr Gln Ser Asp Phe Gly Lys Val Thr
        595                 600                 605
Met Gln Phe Glu Leu Glu Val Cys Gln Leu Gln Lys Pro Asp Val Val
    610                 615                 620
Gly Ile Arg Arg Gln Arg Leu Lys Gly Asp Ala Trp Val Tyr Lys Arg
625                 630                 635                 640
Leu Val Glu Asp Ile Leu Ser Ser Cys Lys Val
                645                 650

<210> SEQ ID NO 3
<211> LENGTH: 1833
<212> TYPE: DNA
<213> ORGANISM: Homo sapiens

<400> SEQUENCE: 3
atgaaagatt atgatgaact tctcaaatat tatgaattac atgaaactat tgggacaggt      60
ggctttgcaa aggtcaaact tgcctgccat atccttactg agagatggt agctataaaa      120 atcatggata aaacacacact agggagtgat ttgccccgga tcaaaacgga gattgaggcc     180
ttgaagaacc tgagacatca gcatatatgt caactctacc atgtgctaga dacagccaac     240
aaaatattca tggttcttga gtactgccct ggaggagagc tgtttgacta taatttcc      300
```

```
caggatcgcc tgtcagaaga ggagacccgg gttgtcttcc gtcagatagt atctgctgtt    360
gcttatgtgc acagccaggg ctatgctcac agggacctca agccagaaaa tttgctgttt    420
gatgaatatc ataaattaaa gctgattgac tttggtctct gtgcaaaacc caagggtaac    480
aaggattacc atctacagac atgctgtggg agtctggctt atgcagcacc tgagttaata    540
caaggcaaat catatcttgg atcagaggca gatgtttgga gcatgggcat actgttatat    600
gttcttatgt gtggatttct accatttgat gatgataatg taatggcttt atacaagaag    660
attatgagag gaaaatatga tgttcccaag tggctctctc ccagtagcat tctgcttctt    720
caacaaatgc tgcaggtgga cccaaagaaa cggatttcta tgaaaaatct attgaaccat    780
ccctggatca tgcaagatta caactatcct gttgagtggc aaagcaagaa tccttttatt    840
cacctcgatg atgattgcgt aacagaactt tctgtacatc acagaaacaa caggcaaaca    900
atggaggatt taatttcact gtggcagtat gatcacctca cggctaccta tcttctgctt    960
ctagccaaga aggctcgggg aaaaccagtt cgtttaaggc tttcttcttt ctcctgtgga   1020
caagccagtg ctaccccatt cacagacatc aagtttacca agtactggac agaatcaaat   1080
gggtggaat ctaaatcatt aactccagcc ttatgcagaa cacctgcaaa taaattaaag   1140
aacaaagaaa atgtatatac tcctaagtct gctgtaaaga atgaagagta ctttatgttt   1200
cctgagccaa agactccagt taataagaac cagcataaga gagaaatact cactacgcca   1260
aatcgttaca ctacaccctc aaaagctaga aaccagtgcc tgaaagaaac tccaattaaa   1320
ataccagtaa attcaacagg aacagacaag ttaatgacag gtgtcattag ccctgagagg   1380
cggtgccgct cagtggaatt ggatctcaac caagcacata tggaggagac tccaaaaaga   1440
aagggagcca aagtgtttgg gagccttgaa aggggggttgg ataaggttat cactgtgctc   1500
accaggagca aaaggaaggg ttctgccaga gacgggccca gaagactaaa gcttcactat   1560
aacgtgacta caactagatt agtgaatcca gatcaactgt tgaatgaaat aatgtctatt   1620
cttccaaaga agcatgttga ctttgtacaa aagggttata cactgaagtg tcaaacacag   1680
tcagattttg ggaaagtgac aatgcaattt gaattagaag tgtgccagct tcaaaaaccc   1740
gatgtggtgg gtatcaggag gcagcggctt aagggcgatg cctgggttta caaaagatta   1800
gtggaagaca tcctatctag ctgcaaggta taa                                1833
```

<210> SEQ ID NO 4
<211> LENGTH: 610
<212> TYPE: PRT
<213> ORGANISM: Homo sapiens

<400> SEQUENCE: 4

```
Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
    50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95
```

-continued

Tyr Ile Ile Ser Gln Asp Arg Leu Ser Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
        130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
        180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
        210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
        275                 280                 285

Glu Leu Ser Val His His Arg Asn Asn Arg Gln Thr Met Glu Asp Leu
        290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
                325                 330                 335

Phe Ser Cys Gly Gln Ala Ser Ala Thr Pro Phe Thr Asp Ile Lys Phe
            340                 345                 350

Thr Lys Tyr Trp Thr Glu Ser Asn Gly Val Glu Ser Lys Ser Leu Thr
        355                 360                 365

Pro Ala Leu Cys Arg Thr Pro Ala Asn Lys Leu Lys Asn Lys Glu Asn
370                 375                 380

Val Tyr Thr Pro Lys Ser Ala Val Lys Asn Glu Glu Tyr Phe Met Phe
385                 390                 395                 400

Pro Glu Pro Lys Thr Pro Val Asn Lys Asn Gln His Lys Arg Glu Ile
                405                 410                 415

Leu Thr Thr Pro Asn Arg Tyr Thr Thr Pro Ser Lys Ala Arg Asn Gln
            420                 425                 430

Cys Leu Lys Glu Thr Pro Ile Lys Ile Pro Val Asn Ser Thr Gly Thr
        435                 440                 445

Asp Lys Leu Met Thr Gly Val Ile Ser Pro Glu Arg Arg Cys Arg Ser
450                 455                 460

Val Glu Leu Asp Leu Asn Gln Ala His Met Glu Glu Thr Pro Lys Arg
465                 470                 475                 480

Lys Gly Ala Lys Val Phe Gly Ser Leu Glu Arg Gly Leu Asp Lys Val
                485                 490                 495

Ile Thr Val Leu Thr Arg Ser Lys Arg Lys Gly Ser Ala Arg Asp Gly
            500                 505                 510

Pro Arg Arg Leu Lys Leu His Tyr Asn Val Thr Thr Thr Arg Leu Val

```
               515                 520                 525
Asn Pro Asp Gln Leu Leu Asn Glu Ile Met Ser Ile Leu Pro Lys Lys
   530                 535                 540

His Val Asp Phe Val Gln Lys Gly Tyr Thr Leu Lys Cys Gln Thr Gln
545                 550                 555                 560

Ser Asp Phe Gly Lys Val Thr Met Gln Phe Glu Leu Glu Val Cys Gln
               565                 570                 575

Leu Gln Lys Pro Asp Val Val Gly Ile Arg Arg Gln Arg Leu Lys Gly
           580                 585                 590

Asp Ala Trp Val Tyr Lys Arg Leu Val Glu Asp Ile Leu Ser Ser Cys
           595                 600                 605

Lys Val
   610

<210> SEQ ID NO 5
<211> LENGTH: 1812
<212> TYPE: DNA
<213> ORGANISM: Homo sapiens

<400> SEQUENCE: 5
```

| | | | |
|---|---|---|---|
| atgaaagatt tgatgaact tctcaaatat tatgaattac atgaaactat tgggacaggt | | | 60 |
| ggctttgcaa aggtcaaact tgcctgccat atccttactg agagatggt agctataaaa | | | 120 |
| atcatggata aaacacact agggagtgat ttgccccgga tcaaaacgga gattgaggcc | | | 180 |
| ttgaagaacc tgagacatca gcatatatgt caactctacc atgtgctaga cagccaac | | | 240 |
| aaaatattca tggttcttga ggaaaatttg ctgtttgatg aatatcataa attaaagctg | | | 300 |
| attgactttg gtctctgtgc aaaacccaag ggtaacaagg attaccatct acagacatgc | | | 360 |
| tgtgggagtc tggcttatgc agcacctgag ttaatacaag gcaaatcata tcttggatca | | | 420 |
| gaggcagatg tttggagcat gggcatactg ttatatgttc ttatgtgtgg atttctacca | | | 480 |
| tttgatgatg ataatgtaat ggcttttatac aagaagatta tgagaggaaa atatgatgtt | | | 540 |
| cccaagtggc tctctcccag tagcattctg cttcttcaac aaatgctgca ggtggaccca | | | 600 |
| aagaaacgga tttctatgaa aaatctattg aaccatccct ggatcatgca agattacaac | | | 660 |
| tatcctgttg agtggcaaag caagaatcct tttattcacc tcgatgatga ttgcgtaaca | | | 720 |
| gaactttctg tacatcacag aaacaacagg caaacaatgg aggatttaat ttcactgtgg | | | 780 |
| cagtatgatc acctcacggc tacctatctt ctgcttctag ccaagaaggc tcggggaaaa | | | 840 |
| ccagttcgtt taaggctttc ttctttctcc tgtggacaag ccagtgctac cccattcaca | | | 900 |
| gacatcaagt caaataattg gagtctggaa gatgtgaccg caagtgataa aaattatgtg | | | 960 |
| gcgggattaa tagactatga ttggtgtgaa gatgatttat caacaggtgc tgctactccc | | | 1020 |
| cgaacatcac agtttaccaa gtactggaca gaatcaaatg gggtggaatc taaatcatta | | | 1080 |
| actccagcct tatgcagaac acctgcaaat aaattaaaga caaagaaaa tgtatatact | | | 1140 |
| cctaagtctg ctgtaaagaa tgaagagtac tttatgtttc ctgagccaaa gactccagtt | | | 1200 |
| aataagaacc agcataagag agaaatactc actacgccaa atcgttacac tacaccctca | | | 1260 |
| aaagctagaa accagtgcct gaaagaaact ccaattaaaa taccagtaaa ttcaacagga | | | 1320 |
| acagacaagt taatgacagg tgtcattagc cctgagaggc ggtgccgctc agtggaattg | | | 1380 |
| gatctcaacc aagcacatat ggaggagact ccaaaaagaa agggagccaa agtgtttggg | | | 1440 |
| agccttgaaa gggggttgga taaggttatc actgtgctca ccaggagcaa aggaagggt | | | 1500 |
| tctgccagag acgggcccag aagactaaag cttcactata acgtgactac aactagatta | | | 1560 |

```
gtgaatccag atcaactgtt gaatgaaata atgtctattc ttccaaagaa gcatgttgac    1620
tttgtacaaa agggttatac actgaagtgt caaacacagt cagattttgg gaaagtgaca    1680
atgcaatttg aattagaagt gtgccagctt caaaaacccg atgtggtggg tatcaggagg    1740
cagcggctta aggcgatgc ctgggtttac aaaagattag tggaagacat cctatctagc     1800
tgcaaggtat aa                                                        1812

<210> SEQ ID NO 6
<211> LENGTH: 603
<212> TYPE: PRT
<213> ORGANISM: Homo sapiens

<400> SEQUENCE: 6
```

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
                20                  25                  30

Thr Gly Glu Met Val Ala Ile Lys Ile Met Asp Lys Asn Thr Leu Gly
            35                  40                  45

Ser Asp Leu Pro Arg Ile Lys Thr Glu Ile Glu Ala Leu Lys Asn Leu
        50                  55                  60

Arg His Gln His Ile Cys Gln Leu Tyr His Val Leu Glu Thr Ala Asn
65                  70                  75                  80

Lys Ile Phe Met Val Leu Glu Glu Asn Leu Leu Phe Asp Glu Tyr His
                85                  90                  95

Lys Leu Lys Leu Ile Asp Phe Gly Leu Cys Ala Lys Pro Lys Gly Asn
            100                 105                 110

Lys Asp Tyr His Leu Gln Thr Cys Cys Gly Ser Leu Ala Tyr Ala Ala
        115                 120                 125

Pro Glu Leu Ile Gln Gly Lys Ser Tyr Leu Gly Ser Glu Ala Asp Val
    130                 135                 140

Trp Ser Met Gly Ile Leu Leu Tyr Val Leu Met Cys Gly Phe Leu Pro
145                 150                 155                 160

Phe Asp Asp Asp Asn Val Met Ala Leu Tyr Lys Lys Ile Met Arg Gly
                165                 170                 175

Lys Tyr Asp Val Pro Lys Trp Leu Ser Pro Ser Ser Ile Leu Leu Leu
            180                 185                 190

Gln Gln Met Leu Gln Val Asp Pro Lys Lys Arg Ile Ser Met Lys Asn
        195                 200                 205

Leu Leu Asn His Pro Trp Ile Met Gln Asp Tyr Asn Tyr Pro Val Glu
    210                 215                 220

Trp Gln Ser Lys Asn Pro Phe Ile His Leu Asp Asp Asp Cys Val Thr
225                 230                 235                 240

Glu Leu Ser Val His His Arg Asn Asn Arg Gln Thr Met Glu Asp Leu
                245                 250                 255

Ile Ser Leu Trp Gln Tyr Asp His Leu Thr Ala Thr Tyr Leu Leu Leu
            260                 265                 270

Leu Ala Lys Lys Ala Arg Gly Lys Pro Val Arg Leu Arg Leu Ser Ser
        275                 280                 285

Phe Ser Cys Gly Gln Ala Ser Ala Thr Pro Phe Thr Asp Ile Lys Ser
    290                 295                 300

Asn Asn Trp Ser Leu Glu Asp Val Thr Ala Ser Asp Lys Asn Tyr Val
305                 310                 315                 320

```
Ala Gly Leu Ile Asp Tyr Asp Trp Cys Glu Asp Leu Ser Thr Gly
            325                 330                 335
Ala Ala Thr Pro Arg Thr Ser Gln Phe Thr Lys Tyr Trp Thr Glu Ser
340                 345                 350
Asn Gly Val Glu Ser Lys Ser Leu Thr Pro Ala Leu Cys Arg Thr Pro
            355                 360                 365
Ala Asn Lys Leu Lys Asn Lys Glu Asn Val Tyr Thr Pro Lys Ser Ala
370                 375                 380
Val Lys Asn Glu Glu Tyr Phe Met Phe Pro Glu Pro Lys Thr Pro Val
385                 390                 395                 400
Asn Lys Asn Gln His Lys Arg Glu Ile Leu Thr Thr Pro Asn Arg Tyr
            405                 410                 415
Thr Thr Pro Ser Lys Ala Arg Asn Gln Cys Leu Lys Glu Thr Pro Ile
            420                 425                 430
Lys Ile Pro Val Asn Ser Thr Gly Thr Asp Lys Leu Met Thr Gly Val
            435                 440                 445
Ile Ser Pro Glu Arg Arg Cys Arg Ser Val Glu Leu Asp Leu Asn Gln
450                 455                 460
Ala His Met Glu Glu Thr Pro Lys Arg Lys Gly Ala Lys Val Phe Gly
465                 470                 475                 480
Ser Leu Glu Arg Gly Leu Asp Lys Val Ile Thr Val Leu Thr Arg Ser
            485                 490                 495
Lys Arg Lys Gly Ser Ala Arg Asp Gly Pro Arg Arg Leu Lys Leu His
            500                 505                 510
Tyr Asn Val Thr Thr Thr Arg Leu Val Asn Pro Asp Gln Leu Leu Asn
            515                 520                 525
Glu Ile Met Ser Ile Leu Pro Lys Lys His Val Asp Phe Val Gln Lys
530                 535                 540
Gly Tyr Thr Leu Lys Cys Gln Thr Gln Ser Asp Phe Gly Lys Val Thr
545                 550                 555                 560
Met Gln Phe Glu Leu Glu Val Cys Gln Leu Gln Lys Pro Asp Val Val
                565                 570                 575
Gly Ile Arg Arg Gln Arg Leu Lys Gly Asp Ala Trp Val Tyr Lys Arg
            580                 585                 590
Leu Val Glu Asp Ile Leu Ser Ser Cys Lys Val
            595                 600

<210> SEQ ID NO 7
<211> LENGTH: 1743
<212> TYPE: DNA
<213> ORGANISM: Homo sapiens

<400> SEQUENCE: 7
atgaaagatt atgatgaact tctcaaatat tatgaattac atgaaactat tgggacaggt     60
ggctttgcaa aggtcaaact tgcctgccat atccttactg agagatggt agctataaaa     120 atcatggata aaaacacact agggagtgat ttgccccgga tcaaaacgga gattgaggcc     180
ttgaagaacc tgagacatca gcatatatgt caactctacc atgtgctaga cagccaac      240 aaaatattca tggttcttga gggtaacaag gattaccatc tacagacatg ctgtgggagt     300
ctggcttatg cagcacctga gttaatacaa ggcaaatcat atcttggatc agaggcagat     360
gtttggagca tgggcatact gttatatgtt cttatgtgtg gatttctacc atttgatgat     420
gataatgtaa tggctttata caagaagatt atgagaggaa atatgatgt cccaagtgg      480 ctctctccca gtagcattct gcttcttcaa caaatgctgc aggtggaccc aaagaaacgg     540
```

```
atttctatga aaaatctatt gaaccatccc tggatcatgc aagattacaa ctatcctgtt    600
gagtggcaaa gcaagaatcc ttttattcac ctcgatgatg attgcgtaac agaactttct    660
gtacatcaca gaaacaacag gcaaacaatg gaggatttaa tttcactgtg cagtatgat     720 cacctcacgg ctacctatct tctgcttcta gccaagaagg ctcggggaaa accagttcgt    780
ttaaggcttt cttctttctc ctgtggacaa gccagtgcta ccccattcac agacatcaag    840
tcaaataatt ggagtctgga agatgtgacc gcaagtgata aaaattatgt ggcgggatta    900
atagactatg attggtgtga agatgattta tcaacaggtg ctgctactcc ccgaacatca    960
cagtttacca agtactggac agaatcaaat ggggtggaat ctaaatcatt aactccagcc   1020
ttatgcagaa cacctgcaaa taattaaag aacaagaaa atgtatatac tcctaagtct     1080
gctgtaaaga atgaagagta ctttatgttt cctgagccaa agactccagt taataagaac   1140
cagcataaga gagaaatact cactacgcca atcgttaca ctacaccctc aaaagctaga    1200
aaccagtgcc tgaaagaaac tccaattaaa ataccagtaa attcaacagg aacagacaag   1260
ttaatgacag gtgtcattag ccctgagagg cggtgccgct cagtggaatt ggatctcaac   1320
caagcacata tggaggagac tccaaaaaga aagggagcca agtgtttggg agccttgaa    1380 agggggttgg ataaggttat cactgtgctc accaggagca aaaggaaggg ttctgccaga   1440
gacgggccca gaagactaaa gcttcactat aacgtgacta caactagatt agtgaatcca   1500
gatcaactgt tgaatgaaat aatgtctatt cttccaaaga agcatgttga ctttgtacaa   1560
aagggttata cactgaagtg tcaaacacag tcagattttg ggaaagtgac aatgcaattt   1620
gaattagaag tgtgccagct tcaaaaaccc gatgtggtgg gtatcaggag cagcggctt    1680 aagggcgatg cctgggttta caaaagatta gtggaagaca tcctatctag ctgcaaggta   1740
taa                                                                 1743
```

<210> SEQ ID NO 8
<211> LENGTH: 580
<212> TYPE: PRT
<213> ORGANISM: Homo sapiens

<400> SEQUENCE: 8

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
                20                  25                  30

Thr Gly Glu Met Val Ala Ile Lys Ile Met Asp Lys Asn Thr Leu Gly
            35                  40                  45

Ser Asp Leu Pro Arg Ile Lys Thr Glu Ile Glu Ala Leu Lys Asn Leu
        50                  55                  60

Arg His Gln His Ile Cys Gln Leu Tyr His Val Leu Glu Thr Ala Asn
65                  70                  75                  80

Lys Ile Phe Met Val Leu Glu Gly Asn Lys Asp Tyr His Leu Gln Thr
                85                  90                  95

Cys Cys Gly Ser Leu Ala Tyr Ala Ala Pro Glu Leu Ile Gln Gly Lys
            100                 105                 110

Ser Tyr Leu Gly Ser Glu Ala Asp Val Trp Ser Met Gly Ile Leu Leu
        115                 120                 125

Tyr Val Leu Met Cys Gly Phe Leu Pro Phe Asp Asp Asp Asn Val Met
    130                 135                 140

Ala Leu Tyr Lys Lys Ile Met Arg Gly Lys Tyr Asp Val Pro Lys Trp

```
            145                 150                 155                 160
Leu Ser Pro Ser Ser Ile Leu Leu Gln Gln Met Leu Gln Val Asp
                165                 170                 175
Pro Lys Lys Arg Ile Ser Met Lys Asn Leu Leu Asn His Pro Trp Ile
                180                 185                 190
Met Gln Asp Tyr Asn Tyr Pro Val Glu Trp Gln Ser Lys Asn Pro Phe
                195                 200                 205
Ile His Leu Asp Asp Cys Val Thr Glu Leu Ser Val His His Arg
        210                 215                 220
Asn Asn Arg Gln Thr Met Glu Asp Leu Ile Ser Leu Trp Gln Tyr Asp
225                 230                 235                 240
His Leu Thr Ala Thr Tyr Leu Leu Leu Ala Lys Lys Ala Arg Gly
                245                 250                 255
Lys Pro Val Arg Leu Arg Leu Ser Ser Phe Ser Cys Gly Gln Ala Ser
                260                 265                 270
Ala Thr Pro Phe Thr Asp Ile Lys Ser Asn Asn Trp Ser Leu Glu Asp
        275                 280                 285
Val Thr Ala Ser Asp Lys Asn Tyr Val Ala Gly Leu Ile Asp Tyr Asp
        290                 295                 300
Trp Cys Glu Asp Asp Leu Ser Thr Gly Ala Ala Thr Pro Arg Thr Ser
305                 310                 315                 320
Gln Phe Thr Lys Tyr Trp Thr Glu Ser Asn Gly Val Glu Ser Lys Ser
                325                 330                 335
Leu Thr Pro Ala Leu Cys Arg Thr Pro Ala Asn Lys Leu Lys Asn Lys
                340                 345                 350
Glu Asn Val Tyr Thr Pro Lys Ser Ala Val Lys Asn Glu Glu Tyr Phe
                355                 360                 365
Met Phe Pro Glu Pro Lys Thr Pro Val Asn Lys Asn Gln His Lys Arg
                370                 375                 380
Glu Ile Leu Thr Thr Pro Asn Arg Tyr Thr Thr Pro Ser Lys Ala Arg
385                 390                 395                 400
Asn Gln Cys Leu Lys Glu Thr Pro Ile Lys Ile Pro Val Asn Ser Thr
                405                 410                 415
Gly Thr Asp Lys Leu Met Thr Gly Val Ile Ser Pro Glu Arg Arg Cys
                420                 425                 430
Arg Ser Val Glu Leu Asp Leu Asn Gln Ala His Met Glu Glu Thr Pro
                435                 440                 445
Lys Arg Lys Gly Ala Lys Val Phe Gly Ser Leu Glu Arg Gly Leu Asp
450                 455                 460
Lys Val Ile Thr Val Leu Thr Arg Ser Lys Arg Lys Gly Ser Ala Arg
465                 470                 475                 480
Asp Gly Pro Arg Arg Leu Lys Leu His Tyr Asn Val Thr Thr Thr Arg
                485                 490                 495
Leu Val Asn Pro Asp Gln Leu Leu Asn Glu Ile Met Ser Ile Leu Pro
                500                 505                 510
Lys Lys His Val Asp Phe Val Gln Lys Gly Tyr Thr Leu Lys Cys Gln
                515                 520                 525
Thr Gln Ser Asp Phe Gly Lys Val Thr Met Gln Phe Glu Leu Glu Val
                530                 535                 540
Cys Gln Leu Gln Lys Pro Asp Val Val Gly Ile Arg Arg Gln Arg Leu
545                 550                 555                 560
Lys Gly Asp Ala Trp Val Tyr Lys Arg Leu Val Glu Asp Ile Leu Ser
                565                 570                 575
```

<210> SEQ ID NO 9
<211> LENGTH: 1860
<212> TYPE: DNA
<213> ORGANISM: Homo sapiens

<400> SEQUENCE: 9

```
atgatgaact tctcaaatat tatgaattac atgaaactat tgggacagag tgatttgccc      60
cggatcaaaa cggagattga ggccttgaag aacctgagac atcagcatat atgtcaactc     120
taccatgtgc tagagacagc caacaaaata ttcatggttc ttgagtactg ccctggagga     180
gagctgtttg actatataat ttcccaggat cgcctgtcag aagaggagac ccggggttgtc    240
ttccgtcaga tagtatctgc tgttgcttat gtgcacagcc agggctatgc tcacagggac     300
ctcaagccag aaaatttgct gtttgatgaa tatcataaat taaagctgat tgactttggt     360
ctctgtgcaa acccaagggt aacaaggat taccatctac agacatgctg tgggagtctg      420
gcttatgcag cacctgagtt aatacaaggc aaatcatatc ttggatcaga ggcagatgtt     480
tggagcatgg gcatactgtt atatgttctt atgtgtggat ttctaccatt tgatgatgat     540
aatgtaatgg ctttatacaa gaagattatg agaggaaaat atgatgttcc caagtggctc     600
tctcccagta gcattctgct tcttcaacaa atgctgcagg tggacccaaa gaacggatt     660
tctatgaaaa atctattgaa ccatccctgg atcatgcaag attacaacta tcctgttgag     720
tggcaaagca agaatccttt tattcacctc gatgatgatt gcgtaacaga actttctgta     780
catcacagaa acaacaggca acaatggagg atttaatttc actgtggca gtatgatcac      840
ctcacggcta cctatcttct gcttctagcc aagaaggctc ggggaaaacc agttcgttta     900
aggctttctt ctttctcctg tggacaagcc agtgctaccc cattcacaga catcaagtca     960
aataattgga gtctggaaga tgtgaccgca agtgataaaa attatgtggc gggattaata    1020
gactatgatt ggtgtgaaga tgatttatca acaggtgctg ctactccccg aacatcacag    1080
tttaccaagt actggacaga atcaaatggg gtggaatcta aatcattaac tccagcctta    1140
tgcagaacac ctgcaaataa attaaagaac aaagaaaatg tatatactcc taagtctgct    1200
gtaaagaatg aagagtactt tatgtttcct gagccaaaga ctccagttaa taagaaccag    1260
cataagagag aaatactcac tacgccaaat cgttcacta cacccctcaaa agctagaaac    1320
cagtgcctga agaaactcc aattaaaata ccagtaaatt caacaggaac agacaagtta    1380
atgacaggtg tcattagccc tgagaggcgg tgccgctcag tggaattgga tctcaaccaa    1440
gcacatatgg aggagactcc aaaaagaaag ggagccaaag tgtttgggag ccttgaaagg    1500
gggttggata aggttatcac tgtgctcacc aggagcaaaa ggaagggttc tgccagagac    1560
gggcccagaa gactaaagct tcactataac gtgactacaa ctagattagt gaatccagat    1620
caactgttga atgaaataat gtctattctt ccaaagaagc atgttgactt tgtacaaaag    1680
ggttatacac tgaagtgtca aacacagtca gattttggga agtgacaat gcaatttgaa    1740
ttagaagtgt gccagcttca aaacccgat gtggtgggta tcaggaggca gcggcttaag    1800
ggcgatgcct gggtttacaa aagattagtg gaagacatcc tatctagctg caaggtataa    1860
```

<210> SEQ ID NO 10
<211> LENGTH: 619
<212> TYPE: PRT
<213> ORGANISM: Homo sapiens

<400> SEQUENCE: 10

```
Met Met Asn Phe Ser Asn Ile Met Asn Tyr Met Lys Leu Leu Gly Gln
1               5                   10                  15

Ser Asp Leu Pro Arg Ile Lys Thr Glu Ile Glu Ala Leu Lys Asn Leu
            20                  25                  30

Arg His Gln His Ile Cys Gln Leu Tyr His Val Leu Glu Thr Ala Asn
        35                  40                  45

Lys Ile Phe Met Val Leu Glu Tyr Cys Pro Gly Gly Glu Leu Phe Asp
    50                  55                  60

Tyr Ile Ile Ser Gln Asp Arg Leu Ser Glu Glu Thr Arg Val Val
65                  70                  75                  80

Phe Arg Gln Ile Val Ser Ala Val Ala Tyr Val His Ser Gln Gly Tyr
                85                  90                  95

Ala His Arg Asp Leu Lys Pro Glu Asn Leu Leu Phe Asp Glu Tyr His
            100                 105                 110

Lys Leu Lys Leu Ile Asp Phe Gly Leu Cys Ala Lys Pro Lys Gly Asn
            115                 120                 125

Lys Asp Tyr His Leu Gln Thr Cys Cys Gly Ser Leu Ala Tyr Ala Ala
    130                 135                 140

Pro Glu Leu Ile Gln Gly Lys Ser Tyr Leu Gly Ser Glu Ala Asp Val
145                 150                 155                 160

Trp Ser Met Gly Ile Leu Leu Tyr Val Leu Met Cys Gly Phe Leu Pro
                165                 170                 175

Phe Asp Asp Asp Asn Val Met Ala Leu Tyr Lys Lys Ile Met Arg Gly
            180                 185                 190

Lys Tyr Asp Val Pro Lys Trp Leu Ser Pro Ser Ser Ile Leu Leu Leu
    195                 200                 205

Gln Gln Met Leu Gln Val Asp Pro Lys Lys Arg Ile Ser Met Lys Asn
    210                 215                 220

Leu Leu Asn His Pro Trp Ile Met Gln Asp Tyr Asn Tyr Pro Val Glu
225                 230                 235                 240

Trp Gln Ser Lys Asn Pro Phe Ile His Leu Asp Asp Asp Cys Val Thr
                245                 250                 255

Glu Leu Ser Val His His Arg Asn Asn Arg Gln Thr Met Glu Asp Leu
            260                 265                 270

Ile Ser Leu Trp Gln Tyr Asp His Leu Thr Ala Thr Tyr Leu Leu Leu
    275                 280                 285

Leu Ala Lys Lys Ala Arg Gly Lys Pro Val Arg Leu Arg Leu Ser Ser
    290                 295                 300

Phe Ser Cys Gly Gln Ala Ser Ala Thr Pro Phe Thr Asp Ile Lys Ser
305                 310                 315                 320

Asn Asn Trp Ser Leu Glu Asp Val Thr Ala Ser Asp Lys Asn Tyr Val
                325                 330                 335

Ala Gly Leu Ile Asp Tyr Asp Trp Cys Glu Asp Asp Leu Ser Thr Gly
            340                 345                 350

Ala Ala Thr Pro Arg Thr Ser Gln Phe Thr Lys Tyr Trp Thr Glu Ser
        355                 360                 365

Asn Gly Val Glu Ser Lys Ser Leu Thr Pro Ala Leu Cys Arg Thr Pro
    370                 375                 380

Ala Asn Lys Leu Lys Asn Lys Glu Asn Val Tyr Thr Pro Lys Ser Ala
385                 390                 395                 400

Val Lys Asn Glu Glu Tyr Phe Met Phe Pro Glu Pro Lys Thr Pro Val
```

```
                    405                 410                 415
Asn Lys Asn Gln His Lys Arg Glu Ile Leu Thr Thr Pro Asn Arg Tyr
            420                 425                 430

Thr Thr Pro Ser Lys Ala Arg Asn Gln Cys Leu Lys Glu Thr Pro Ile
        435                 440                 445

Lys Ile Pro Val Asn Ser Thr Gly Thr Asp Lys Leu Met Thr Gly Val
    450                 455                 460

Ile Ser Pro Glu Arg Arg Cys Arg Ser Val Glu Leu Asp Leu Asn Gln
465                 470                 475                 480

Ala His Met Glu Glu Thr Pro Lys Arg Lys Gly Ala Lys Val Phe Gly
                485                 490                 495

Ser Leu Glu Arg Gly Leu Asp Lys Val Ile Thr Val Leu Thr Arg Ser
            500                 505                 510

Lys Arg Lys Gly Ser Ala Arg Asp Gly Pro Arg Arg Leu Lys Leu His
        515                 520                 525

Tyr Asn Val Thr Thr Thr Arg Leu Val Asn Pro Asp Gln Leu Leu Asn
    530                 535                 540

Glu Ile Met Ser Ile Leu Pro Lys Lys His Val Asp Phe Val Gln Lys
545                 550                 555                 560

Gly Tyr Thr Leu Lys Cys Gln Thr Gln Ser Asp Phe Gly Lys Val Thr
                565                 570                 575

Met Gln Phe Glu Leu Glu Val Cys Gln Leu Gln Lys Pro Asp Val Val
            580                 585                 590

Gly Ile Arg Arg Gln Arg Leu Lys Gly Asp Ala Trp Val Tyr Lys Arg
        595                 600                 605

Leu Val Glu Asp Ile Leu Ser Ser Cys Lys Val
    610                 615

<210> SEQ ID NO 11
<211> LENGTH: 1743
<212> TYPE: DNA
<213> ORGANISM: Homo sapiens

<400> SEQUENCE: 11
atgatgaact tctcaaatat tatgaattac atgaaactat tgggacagta ctgccctgga        60
ggagagctgt ttgactatat aatttcccag gatcgcctgt cagaagagga gacccgggtt       120
gtcttccgtc agatagtatc tgctgttgct tatgtgcaca gccagggcta tgctcacagg       180
gacctcaagc cagaaaattt gctgtttgat gaatatcata aattaaagct gattgacttt       240
ggtctctgtg caaacccaa gggtaacaag gattaccatc tacagacatg ctgtgggagt       300
ctggcttatg cagcacctga gttaatacaa ggcaaatcat atcttggatc agaggcagat       360
gtttggagca tggcatact gttatatgtt cttatgtgtg gatttctacc atttgatgat       420
gataatgtaa tggctttata caagaagatt atgagaggaa aatatgatgt tcccaagtgg       480
ctctctccca gtagcattct gcttcttcaa caaatgctgc aggtggaccc aaagaaacgg       540
atttctatga aaaatctatt gaaccatccc tggatcatgc aagattacaa ctatcctgtt       600
gagtggcaaa gcaagaatcc ttttattcac ctcgatgatg attgcgtaac agaactttct       660
gtacatcaca gaaacaacag gcaaacaatg gaggatttaa tttcactgtg cagtatgat        720 caccttcacgg ctacctatct tctgcttcta gccaagaagg ctcggggaaa accagttcgt       780
ttaaggcttt cttctttctc ctgtggacaa gccagtgcta ccccattcac agacatcaag       840
tcaaataatt ggagtctgga agatgtgacc gcaagtgata aaaattatgt ggcgggatta       900
```

```
atagactatg attggtgtga agatgattta tcaacaggtg ctgctactcc ccgaacatca    960
cagtttacca agtactggac agaatcaaat ggggtggaat ctaaatcatt aactccagcc   1020
ttatgcagaa caccctgcaaa taaattaaag aacaaagaaa atgtatatac tcctaagtct   1080
gctgtaaaga atgaagagta ctttatgttt cctgagccaa agactccagt taataagaac   1140
cagcataaga gagaaatact cactacgcca aatcgttaca ctacaccctc aaaagctaga   1200
aaccagtgcc tgaaagaaac tccaattaaa ataccagtaa attcaacagg aacagacaag   1260
ttaatgacag gtgtcattag ccctgagagg cggtgccgct cagtggaatt ggatctcaac   1320
caagcacata tggaggagac tccaaaaaga aagggagcca agtgtttggg agccttgaa    1380 agggggttgg ataaggttat cactgtgctc accaggagca aaaggaaggg ttctgccaga   1440
gacgggccca gaagactaaa gcttcactat aacgtgacta caactagatt agtgaatcca   1500
gatcaactgt tgaatgaaat aatgtctatt cttccaaaga agcatgttga ctttgtacaa   1560
aagggttata cactgaagtg tcaaacacag tcagattttg ggaaagtgac aatgcaattt   1620
gaattagaag tgtgccagct tcaaaaaccc gatgtggtgg gtatcaggag gcagcggctt   1680
aagggcgatg cctgggttta caaaagatta gtggaagaca tcctatctag ctgcaaggta   1740
taa                                                                 1743
```

<210> SEQ ID NO 12
<211> LENGTH: 580
<212> TYPE: PRT
<213> ORGANISM: Homo sapiens

<400> SEQUENCE: 12

```
Met Met Asn Phe Ser Asn Ile Met Asn Tyr Met Lys Leu Leu Gly Gln
1               5                   10                  15

Tyr Cys Pro Gly Gly Glu Leu Phe Asp Tyr Ile Ile Ser Gln Asp Arg
            20                  25                  30

Leu Ser Glu Glu Thr Arg Val Val Phe Arg Gln Ile Val Ser Ala
        35                  40                  45

Val Ala Tyr Val His Ser Gln Gly Tyr Ala His Arg Asp Leu Lys Pro
    50                  55                  60

Glu Asn Leu Leu Phe Asp Glu Tyr His Lys Leu Lys Leu Ile Asp Phe
65                  70                  75                  80

Gly Leu Cys Ala Lys Pro Lys Gly Asn Lys Asp Tyr His Leu Gln Thr
                85                  90                  95

Cys Cys Gly Ser Leu Ala Tyr Ala Ala Pro Glu Leu Ile Gln Gly Lys
            100                 105                 110

Ser Tyr Leu Gly Ser Glu Ala Asp Val Trp Ser Met Gly Ile Leu Leu
        115                 120                 125

Tyr Val Leu Met Cys Gly Phe Leu Pro Phe Asp Asp Asn Val Met
    130                 135                 140

Ala Leu Tyr Lys Lys Ile Met Arg Gly Lys Tyr Asp Val Pro Lys Trp
145                 150                 155                 160

Leu Ser Pro Ser Ser Ile Leu Leu Leu Gln Gln Met Leu Gln Val Asp
                165                 170                 175

Pro Lys Lys Arg Ile Ser Met Lys Asn Leu Leu Asn His Pro Trp Ile
            180                 185                 190

Met Gln Asp Tyr Asn Tyr Pro Val Glu Trp Gln Ser Lys Asn Pro Phe
        195                 200                 205

Ile His Leu Asp Asp Asp Cys Val Thr Glu Leu Ser Val His His Arg
    210                 215                 220
```

Asn Asn Arg Gln Thr Met Glu Asp Leu Ile Ser Leu Trp Gln Tyr Asp
225                 230                 235                 240

His Leu Thr Ala Thr Tyr Leu Leu Leu Leu Ala Lys Lys Ala Arg Gly
            245                 250                 255

Lys Pro Val Arg Leu Arg Leu Ser Ser Phe Ser Cys Gly Gln Ala Ser
        260                 265                 270

Ala Thr Pro Phe Thr Asp Ile Lys Ser Asn Asn Trp Ser Leu Glu Asp
    275                 280                 285

Val Thr Ala Ser Asp Lys Asn Tyr Val Ala Gly Leu Ile Asp Tyr Asp
290                 295                 300

Trp Cys Glu Asp Asp Leu Ser Thr Gly Ala Ala Thr Pro Arg Thr Ser
305                 310                 315                 320

Gln Phe Thr Lys Tyr Trp Thr Glu Ser Asn Gly Val Glu Ser Lys Ser
            325                 330                 335

Leu Thr Pro Ala Leu Cys Arg Thr Pro Ala Asn Lys Leu Lys Asn Lys
        340                 345                 350

Glu Asn Val Tyr Thr Pro Lys Ser Ala Val Lys Asn Glu Glu Tyr Phe
    355                 360                 365

Met Phe Pro Glu Pro Lys Thr Pro Val Asn Lys Asn Gln His Lys Arg
370                 375                 380

Glu Ile Leu Thr Thr Pro Asn Arg Tyr Thr Thr Pro Ser Lys Ala Arg
385                 390                 395                 400

Asn Gln Cys Leu Lys Glu Thr Pro Ile Lys Ile Pro Val Asn Ser Thr
            405                 410                 415

Gly Thr Asp Lys Leu Met Thr Gly Val Ile Ser Pro Glu Arg Arg Cys
        420                 425                 430

Arg Ser Val Glu Leu Asp Leu Asn Gln Ala His Met Glu Glu Thr Pro
    435                 440                 445

Lys Arg Lys Gly Ala Lys Val Phe Gly Ser Leu Glu Arg Gly Leu Asp
450                 455                 460

Lys Val Ile Thr Val Leu Thr Arg Ser Lys Arg Lys Gly Ser Ala Arg
465                 470                 475                 480

Asp Gly Pro Arg Arg Leu Lys Leu His Tyr Asn Val Thr Thr Thr Arg
            485                 490                 495

Leu Val Asn Pro Asp Gln Leu Leu Asn Glu Ile Met Ser Ile Leu Pro
        500                 505                 510

Lys Lys His Val Asp Phe Val Gln Lys Gly Tyr Thr Leu Lys Cys Gln
    515                 520                 525

Thr Gln Ser Asp Phe Gly Lys Val Thr Met Gln Phe Glu Leu Glu Val
530                 535                 540

Cys Gln Leu Gln Lys Pro Asp Val Val Gly Ile Arg Arg Gln Arg Leu
545                 550                 555                 560

Lys Gly Asp Ala Trp Val Tyr Lys Arg Leu Val Glu Asp Ile Leu Ser
            565                 570                 575

Ser Cys Lys Val
        580

<210> SEQ ID NO 13
<211> LENGTH: 1716
<212> TYPE: DNA
<213> ORGANISM: Homo sapiens

<400> SEQUENCE: 13
atgatgaact tctcaaatat tatgaattac atgaaactat tgggacagag tgatttgccc        60

```
cggatcaaaa cggagattga ggccttgaag aacctgagac atcagcatat atgtcaactc      120
taccatgtgc tagagacagc caacaaaata ttcatggttc ttgaggaaaa tttgctgttt      180
gatgaatatc ataaattaaa gctgattgac tttggtctct gtgcaaaacc caagggtaac      240
aaggattacc atctacagac atgctgtggg agtctggctt atgcagcacc tgagttaata      300
caaggcaaat catatcttgg atcagaggca gatgtttgga gcatgggcat actgttatat      360
gttcttatgt gtggatttct accatttgat gatgataatg taatggcttt atacaagaag      420
attatgagag gaaaatatga tgttcccaag tggctctctc ccagtagcat tctgcttctt      480
caacaaatgc tgcaggtgga cccaagaaaa cggatttcta tgaaaaatct attgaaccat      540
ccctggatca tgcaagatta caactatcct gttgagtggc aaagcaagaa tccttttatt      600
cacctcgatg atgattgcgt aacagaactt tctgtacatc acagaaacaa caggcaaaca      660
atggaggatt taatttcact gtggcagtat gatcacctca cggctaccta tcttctgctt      720
ctagccaaga aggctcgggg aaaaccagtt cgtttaaggc tttcttcttt ctcctgtgga      780
caagccagtg ctaccccatt cacagacatc aagtcaaata attggagtct ggaagatgtg      840
accgcaagtg ataaaaatta tgtggcggga ttaatagact atgattggtg tgaagatgat      900
ttatcaacag gtgctgctac tccccgaaca tcacagtta ccaagtactg gacagaatca       960
aatggggtgg aatctaaatc attaactcca gccttatgca gaacacctgc aaataaatta     1020
aagaacaaag aaaatgtata tactcctaag tctgctgtaa agaatgaaga gtactttatg     1080
tttcctgagc caaagactcc agttaataag aaccagcata gagagaaat actcactacg     1140 ccaaatcgtt acactacacc ctcaaaagct agaaaccagt gcctgaaaga aactccaatt     1200
aaaataccag taaattcaac aggaacagac aagttaatga caggtgtcat tagccctgag     1260
aggcggtgcc gctcagtgga attggatctc aaccaagcac atatggagga gactccaaaa     1320
agaaagggag ccaaagtgtt tgggagcctt gaaggggggt tggataaggt tatcactgtg     1380
ctcaccagga gcaaaaggaa gggttctgcc agagacgggc ccagaagact aaagcttcac     1440
tataacgtga ctacaactag attagtgaat ccagatcaac tgttgaatga aataatgtct     1500
attcttccaa agaagcatgt tgactttgta caaaagggtt atacactgaa gtgtcaaaca     1560
cagtcagatt ttgggaaagt gacaatgcaa tttgaattag aagtgtgcca gcttcaaaaa     1620
cccgatgtgt gggtatcag gaggcagcgg cttaagggcg atgcctgggt ttacaaaaga     1680
ttagtggaag acatcctatc tagctgcaag gtataa                               1716
```

<210> SEQ ID NO 14  
<211> LENGTH: 571  
<212> TYPE: PRT  
<213> ORGANISM: Homo sapiens

<400> SEQUENCE: 14

```
Met Met Asn Phe Ser Asn Ile Met Asn Tyr Met Lys Leu Leu Gly Gln
1               5                   10                  15

Ser Asp Leu Pro Arg Ile Lys Thr Glu Ile Glu Ala Leu Lys Asn Leu
            20                  25                  30

Arg His Gln His Ile Cys Gln Leu Tyr His Val Leu Glu Thr Ala Asn
        35                  40                  45

Lys Ile Phe Met Val Leu Glu Glu Asn Leu Leu Phe Asp Glu Tyr His
    50                  55                  60

Lys Leu Lys Leu Ile Asp Phe Gly Leu Cys Ala Lys Pro Lys Gly Asn
65                  70                  75                  80
```

```
Lys Asp Tyr His Leu Gln Thr Cys Cys Gly Ser Leu Ala Tyr Ala Ala
                85              90                  95

Pro Glu Leu Ile Gln Gly Lys Ser Tyr Leu Gly Ser Glu Ala Asp Val
            100                 105                 110

Trp Ser Met Gly Ile Leu Leu Tyr Val Leu Met Cys Gly Phe Leu Pro
            115                 120                 125

Phe Asp Asp Asn Val Met Ala Leu Tyr Lys Lys Ile Met Arg Gly
130                 135                 140

Lys Tyr Asp Val Pro Lys Trp Leu Ser Pro Ser Ser Ile Leu Leu Leu
145                 150                 155                 160

Gln Gln Met Leu Gln Val Asp Pro Lys Lys Arg Ile Ser Met Lys Asn
                165                 170                 175

Leu Leu Asn His Pro Trp Ile Met Gln Asp Tyr Asn Tyr Pro Val Glu
            180                 185                 190

Trp Gln Ser Lys Asn Pro Phe Ile His Leu Asp Asp Asp Cys Val Thr
        195                 200                 205

Glu Leu Ser Val His His Arg Asn Asn Arg Gln Thr Met Glu Asp Leu
    210                 215                 220

Ile Ser Leu Trp Gln Tyr Asp His Leu Thr Ala Thr Tyr Leu Leu Leu
225                 230                 235                 240

Leu Ala Lys Lys Ala Arg Gly Lys Pro Val Arg Leu Arg Leu Ser Ser
                245                 250                 255

Phe Ser Cys Gly Gln Ala Ser Ala Thr Pro Phe Thr Asp Ile Lys Ser
            260                 265                 270

Asn Asn Trp Ser Leu Glu Asp Val Thr Ala Ser Asp Lys Asn Tyr Val
        275                 280                 285

Ala Gly Leu Ile Asp Tyr Asp Trp Cys Glu Asp Leu Ser Thr Gly
    290                 295                 300

Ala Ala Thr Pro Arg Thr Ser Gln Phe Thr Lys Tyr Trp Thr Glu Ser
305                 310                 315                 320

Asn Gly Val Glu Ser Lys Ser Leu Thr Pro Ala Leu Cys Arg Thr Pro
                325                 330                 335

Ala Asn Lys Leu Lys Asn Lys Glu Asn Val Tyr Thr Pro Lys Ser Ala
            340                 345                 350

Val Lys Asn Glu Glu Tyr Phe Met Phe Pro Glu Pro Lys Thr Pro Val
        355                 360                 365

Asn Lys Asn Gln His Lys Arg Glu Ile Leu Thr Thr Pro Asn Arg Tyr
    370                 375                 380

Thr Thr Pro Ser Lys Ala Arg Asn Gln Cys Leu Lys Glu Thr Pro Ile
385                 390                 395                 400

Lys Ile Pro Val Asn Ser Thr Gly Thr Asp Lys Leu Met Thr Gly Val
                405                 410                 415

Ile Ser Pro Glu Arg Arg Cys Arg Ser Val Glu Leu Asp Leu Asn Gln
            420                 425                 430

Ala His Met Glu Glu Thr Pro Lys Arg Lys Gly Ala Lys Val Phe Gly
        435                 440                 445

Ser Leu Glu Arg Gly Leu Asp Lys Val Ile Thr Val Leu Thr Arg Ser
    450                 455                 460

Lys Arg Lys Gly Ser Ala Arg Asp Gly Pro Arg Arg Leu Lys Leu His
465                 470                 475                 480

Tyr Asn Val Thr Thr Thr Arg Leu Val Asn Pro Asp Gln Leu Leu Asn
                485                 490                 495
```

```
Glu Ile Met Ser Ile Leu Pro Lys Lys His Val Asp Phe Val Gln Lys
                500                 505                 510

Gly Tyr Thr Leu Lys Cys Gln Thr Gln Ser Asp Phe Gly Lys Val Thr
            515                 520                 525

Met Gln Phe Glu Leu Glu Val Cys Gln Leu Gln Lys Pro Asp Val Val
        530                 535                 540

Gly Ile Arg Arg Gln Arg Leu Lys Gly Asp Ala Trp Val Tyr Lys Arg
545                 550                 555                 560

Leu Val Glu Asp Ile Leu Ser Ser Cys Lys Val
                565                 570

<210> SEQ ID NO 15
<211> LENGTH: 1563
<212> TYPE: DNA
<213> ORGANISM: Homo sapiens

<400> SEQUENCE: 15
```

| | | | | | |
|---|---|---|---|---|---|
| atggttcttg | aggaaaattt | gctgtttgat | gaatatcata | aattaaagct | gattgacttt | 60 |
| ggtctctgtg | caaaacccaa | gggtaacaag | gattaccatc | tacagacatg | ctgtgggagt | 120 |
| ctggcttatg | cagcacctga | gttaatacaa | ggcaaatcat | atcttggatc | agaggcagat | 180 |
| gtttggagca | tgggcatact | gttatatgtt | cttatgtgtg | gatttctacc | atttgatgat | 240 |
| gataatgtaa | tggctttata | caagaagatt | atgagaggaa | aatatgatgt | tcccaagtgg | 300 |
| ctctctccca | gtagcattct | gcttcttcaa | caaatgctgc | aggtggaccc | aaagaaacgg | 360 |
| atttctatga | aaaatctatt | gaaccatccc | tggatcatgc | aagattacaa | ctatcctgtt | 420 |
| gagtggcaaa | gcaagaatcc | ttttattcac | ctcgatgatg | attgcgtaac | agaactttct | 480 |
| gtacatcaca | gaaacaacag | gcaaacaatg | gaggatttaa | tttcactgtg | gcagtatgat | 540 |
| caccctcacgg | ctacctatct | tctgcttcta | gccaagaagg | ctcggggaaa | accagttcgt | 600 |
| ttaaggcttt | cttctttctc | ctgtggacaa | gccagtgcta | ccccattcac | agacatcaag | 660 |
| tcaaataatt | ggagtctgga | agatgtgacc | gcaagtgata | aaaattatgt | ggcgggatta | 720 |
| atagactatg | attggtgtga | agatgattta | tcaacaggtg | ctgctactcc | ccgaacatca | 780 |
| cagtttacca | agtactggac | agaatcaaat | ggggtggaat | ctaaatcatt | aactccagcc | 840 |
| ttatgcagaa | cacctgcaaa | taattaaag | aacaaagaaa | atgtatatac | tcctaagtct | 900 |
| gctgtaaaga | atgaagagta | ctttatgttt | cctgagccaa | agactccagt | taataagaac | 960 |
| cagcataaga | gagaaatact | cactacgcca | aatcgttaca | ctacaccctc | aaaagctaga | 1020 |
| aaccagtgcc | tgaaagaaac | tccaattaaa | ataccagtaa | attcaacagg | aacagacaag | 1080 |
| ttaatgacag | gtgtcattag | ccctgagagg | cggtgccgct | cagtggaatt | ggatctcaac | 1140 |
| caagcacata | tggaggagac | tccaaaaaga | aaggagccaa | agtgtttggg | agccttgaa | 1200 |
| aggggggttgg | ataaggttat | cactgtgctc | accaggagca | aaaggaaggg | ttctgccaga | 1260 |
| gacgggccca | gaagactaaa | gcttcactat | aacgtgacta | caactagatt | agtgaatcca | 1320 |
| gatcaactgt | tgaatgaaat | aatgtctatt | cttccaagaa | agcatgttga | ctttgtacaa | 1380 |
| aagggttata | cactgaagtg | tcaaacacag | tcagattttg | ggaaagtgac | aatgcaattt | 1440 |
| gaattagaag | tgtgccagct | tcaaaaaccc | gatgtggtgg | gtatcaggag | gcagcggctt | 1500 |
| aagggcgatg | cctgggttta | caaaagatta | gtggaagaca | tcctatctag | ctgcaaggta | 1560 |
| taa | | | | | | 1563 |

```
<210> SEQ ID NO 16
```

```
<211> LENGTH: 520
<212> TYPE: PRT
<213> ORGANISM: Homo sapiens

<400> SEQUENCE: 16

Met Val Leu Glu Glu Asn Leu Leu Phe Asp Glu Tyr His Lys Leu Lys
1               5                   10                  15

Leu Ile Asp Phe Gly Leu Cys Ala Lys Pro Lys Gly Asn Lys Asp Tyr
            20                  25                  30

His Leu Gln Thr Cys Cys Gly Ser Leu Ala Tyr Ala Ala Pro Glu Leu
        35                  40                  45

Ile Gln Gly Lys Ser Tyr Leu Gly Ser Glu Ala Asp Val Trp Ser Met
    50                  55                  60

Gly Ile Leu Leu Tyr Val Leu Met Cys Gly Phe Leu Pro Phe Asp Asp
65                  70                  75                  80

Asp Asn Val Met Ala Leu Tyr Lys Lys Ile Met Arg Gly Lys Tyr Asp
                85                  90                  95

Val Pro Lys Trp Leu Ser Pro Ser Ser Ile Leu Leu Leu Gln Gln Met
            100                 105                 110

Leu Gln Val Asp Pro Lys Lys Arg Ile Ser Met Lys Asn Leu Leu Asn
        115                 120                 125

His Pro Trp Ile Met Gln Asp Tyr Asn Tyr Pro Val Glu Trp Gln Ser
    130                 135                 140

Lys Asn Pro Phe Ile His Leu Asp Asp Asp Cys Val Thr Glu Leu Ser
145                 150                 155                 160

Val His His Arg Asn Asn Arg Gln Thr Met Glu Asp Leu Ile Ser Leu
                165                 170                 175

Trp Gln Tyr Asp His Leu Thr Ala Thr Tyr Leu Leu Leu Leu Ala Lys
            180                 185                 190

Lys Ala Arg Gly Lys Pro Val Arg Leu Arg Leu Ser Ser Phe Ser Cys
        195                 200                 205

Gly Gln Ala Ser Ala Thr Pro Phe Thr Asp Ile Lys Ser Asn Asn Trp
    210                 215                 220

Ser Leu Glu Asp Val Thr Ala Ser Asp Lys Asn Tyr Val Ala Gly Leu
225                 230                 235                 240

Ile Asp Tyr Asp Trp Cys Glu Asp Asp Leu Ser Thr Gly Ala Ala Thr
                245                 250                 255

Pro Arg Thr Ser Gln Phe Thr Lys Tyr Trp Thr Glu Ser Asn Gly Val
            260                 265                 270

Glu Ser Lys Ser Leu Thr Pro Ala Leu Cys Arg Thr Pro Ala Asn Lys
        275                 280                 285

Leu Lys Asn Lys Glu Asn Val Tyr Thr Pro Lys Ser Ala Val Lys Asn
    290                 295                 300

Glu Glu Tyr Phe Met Phe Pro Glu Pro Lys Thr Pro Val Asn Lys Asn
305                 310                 315                 320

Gln His Lys Arg Glu Ile Leu Thr Thr Pro Asn Arg Tyr Thr Thr Pro
                325                 330                 335

Ser Lys Ala Arg Asn Gln Cys Leu Lys Glu Thr Pro Ile Lys Ile Pro
            340                 345                 350

Val Asn Ser Thr Gly Thr Asp Lys Leu Met Thr Gly Val Ile Ser Pro
        355                 360                 365

Glu Arg Arg Cys Arg Ser Val Glu Leu Asp Leu Asn Gln Ala His Met
    370                 375                 380

Glu Glu Thr Pro Lys Arg Lys Gly Ala Lys Val Phe Gly Ser Leu Glu
```

```
                385           390           395           400
Arg Gly Leu Asp Lys Val Ile Thr Val Leu Thr Arg Ser Lys Arg Lys
                405               410               415

Gly Ser Ala Arg Asp Gly Pro Arg Arg Leu Lys Leu His Tyr Asn Val
            420               425               430

Thr Thr Thr Arg Leu Val Asn Pro Asp Gln Leu Leu Asn Glu Ile Met
            435               440               445

Ser Ile Leu Pro Lys Lys His Val Asp Phe Val Gln Lys Gly Tyr Thr
        450               455               460

Leu Lys Cys Gln Thr Gln Ser Asp Phe Gly Lys Val Thr Met Gln Phe
465             470              475                  480

Glu Leu Glu Val Cys Gln Leu Gln Lys Pro Asp Val Val Gly Ile Arg
                485              490                  495

Arg Gln Arg Leu Lys Gly Asp Ala Trp Val Tyr Lys Arg Leu Val Glu
            500              505               510

Asp Ile Leu Ser Ser Cys Lys Val
            515              520

<210> SEQ ID NO 17
<211> LENGTH: 1374
<212> TYPE: DNA
<213> ORGANISM: Homo sapiens

<400> SEQUENCE: 17
atgggcatac tgttatatgt tcttatgtgt ggatttctac catttgatga tgataatgta      60
atggctttat acaagaagat tatgagagga aaatatgatg ttcccaagtg gctctctccc     120
agtagcattc tgcttcttca acaaatgctg caggtggacc caaagaaacg gatttctatg     180
aaaaatctat tgaaccatcc ctggatcatg caagattaca actatcctgt tgagtggcaa     240
agcaagaatc cttttattca cctcgatgat gattgcgtaa cagaactttc tgtacatcac     300
agaaacaaca gcaaacaat ggaggattta atttcactgt ggcagtatga tcacctcacg     360
gctacctatc ttctgcttct agccaagaag gctcgggaa accagttcg tttaaggctt      420
tcttctttct cctgtggaca agccagtgct accccattca cagacatcaa gtcaaataat     480
tggagtctgg aagatgtgac cgcaagtgat aaaaattatg tggcgggatt aatagactat     540
gattggtgtg aagatgattt atcaacaggt gctgctactc cccgaacatc acagtttacc     600
aagtactgga cagaatcaaa tggggtggaa tctaaatcat taactccagc cttatgcaga     660
acacctgcaa ataaattaaa gaacaaagaa atgtgtata ctcctaagtc tgctgtaaag      720
aatgaagagt actttatgtt tcctgagcca agactccag ttaataagaa ccagcataag      780
agagaaatac tcactacgcc aaatcgttac actacaccct caaaagctag aaaccagtgc     840
ctgaagaaaa ctccaattaa ataccagta aattcaacag gaacagacaa gttaatgaca     900
ggtgtcatta gccctgagag gcggtgccgc tcagtggaat tggatctcaa ccaagcacat     960
atggaggaga ctccaaaaag aaagggagcc aaagtgtttg ggagccttga agggggttg     1020
gataaggtta tcactgtgct caccaggagc aaaaggaagg ttctgccag agacgggccc     1080
agaagactaa agcttcacta taacgtgact acaactagta tagtgaatcc agatcaactg    1140
ttgaatgaaa taatgtctat tcttccaaag aagcatgttg actttgtaca aaagggttat    1200
acactgaagt gtcaaacaca gtcagatttt gggaaagtga caatgcaatt tgaattagaa    1260
gtgtgccagc ttcaaaaacc cgatgtggtg ggtatcagga ggcagcggct taagggcgat    1320
gcctgggttt acaaaagatt agtggaagac atcctatcta gctgcaaggt ataa          1374
```

<210> SEQ ID NO 18
<211> LENGTH: 457
<212> TYPE: PRT
<213> ORGANISM: Homo sapiens

<400> SEQUENCE: 18

```
Met Gly Ile Leu Leu Tyr Val Leu Met Cys Gly Phe Leu Pro Phe Asp
1               5                   10                  15

Asp Asp Asn Val Met Ala Leu Tyr Lys Lys Ile Met Arg Gly Lys Tyr
            20                  25                  30

Asp Val Pro Lys Trp Leu Ser Pro Ser Ile Leu Leu Leu Gln Gln
        35                  40                  45

Met Leu Gln Val Asp Pro Lys Lys Arg Ile Ser Met Lys Asn Leu Leu
50                  55                  60

Asn His Pro Trp Ile Met Gln Asp Tyr Asn Tyr Pro Val Glu Trp Gln
65                  70                  75                  80

Ser Lys Asn Pro Phe Ile His Leu Asp Asp Cys Val Thr Glu Leu
            85                  90                  95

Ser Val His His Arg Asn Asn Arg Gln Thr Met Glu Asp Leu Ile Ser
            100                 105                 110

Leu Trp Gln Tyr Asp His Leu Thr Ala Thr Tyr Leu Leu Leu Leu Ala
        115                 120                 125

Lys Lys Ala Arg Gly Lys Pro Val Arg Leu Arg Leu Ser Ser Phe Ser
130                 135                 140

Cys Gly Gln Ala Ser Ala Thr Pro Phe Thr Asp Ile Lys Ser Asn Asn
145                 150                 155                 160

Trp Ser Leu Glu Asp Val Thr Ala Ser Asp Lys Asn Tyr Val Ala Gly
            165                 170                 175

Leu Ile Asp Tyr Asp Trp Cys Glu Asp Asp Leu Ser Thr Gly Ala Ala
        180                 185                 190

Thr Pro Arg Thr Ser Gln Phe Thr Lys Tyr Trp Thr Glu Ser Asn Gly
        195                 200                 205

Val Glu Ser Lys Ser Leu Thr Pro Ala Leu Cys Arg Thr Pro Ala Asn
210                 215                 220

Lys Leu Lys Asn Lys Glu Asn Val Tyr Thr Pro Lys Ser Ala Val Lys
225                 230                 235                 240

Asn Glu Glu Tyr Phe Met Phe Pro Glu Pro Lys Thr Pro Val Asn Lys
            245                 250                 255

Asn Gln His Lys Arg Glu Ile Leu Thr Thr Pro Asn Arg Tyr Thr Thr
            260                 265                 270

Pro Ser Lys Ala Arg Asn Gln Cys Leu Lys Glu Thr Pro Ile Lys Ile
        275                 280                 285

Pro Val Asn Ser Thr Gly Thr Asp Lys Leu Met Thr Gly Val Ile Ser
        290                 295                 300

Pro Glu Arg Arg Cys Arg Ser Val Glu Leu Asp Leu Asn Gln Ala His
305                 310                 315                 320

Met Glu Glu Thr Pro Lys Arg Lys Gly Ala Lys Val Phe Gly Ser Leu
            325                 330                 335

Glu Arg Gly Leu Asp Lys Val Ile Val Leu Thr Arg Ser Lys Arg
            340                 345                 350

Lys Gly Ser Ala Arg Asp Gly Pro Arg Arg Leu Lys Leu His Tyr Asn
        355                 360                 365

Val Thr Thr Thr Arg Leu Val Asn Pro Asp Gln Leu Leu Asn Glu Ile
```

```
                370             375             380
Met Ser Ile Leu Pro Lys Lys His Val Asp Phe Val Gln Lys Gly Tyr
385                 390                 395                 400

Thr Leu Lys Cys Gln Thr Gln Ser Asp Phe Gly Lys Val Thr Met Gln
            405                 410                 415

Phe Glu Leu Glu Val Cys Gln Leu Gln Lys Pro Asp Val Val Gly Ile
        420                 425                 430

Arg Arg Gln Arg Leu Lys Gly Asp Ala Trp Val Tyr Lys Arg Leu Val
            435                 440                 445

Glu Asp Ile Leu Ser Ser Cys Lys Val
            450                 455
```

<210> SEQ ID NO 19
<211> LENGTH: 1932
<212> TYPE: DNA
<213> ORGANISM: Mus musculus

<400> SEQUENCE: 19

```
atgaaagatt atgacgaact cctcaaatac tatgaactat atgaaacgat tgggacaggt    60
ggctttgcaa aggtcaaact ggcctgccat gtcctcactg gagagatggt agctataaaa   120
atcatggata agaatgcgct agggagtgat ttgccccgag tcaaaactga gatcgatgcg   180
ctgaagagtc tgagacatca gcacatatgt cagctctacc atgtgctgga gacaaagaac   240
aaaatattca tggttctgga gtactgtcca ggaggagagc tgtttgacta cataatctcc   300
caggatcgcc tgtcggaaga ggagacccgg gtcgtcttcc gtcagatact gtctgcagtt   360
gcgtatgtcc acagccaggg ctatgcccac agggacctca aaccagaaaa tttattattt   420
gatgaaaatc ataagctaaa gctgattgac tttggtcttt gtgcaaaacc caagggcaac   480
aaggactacc atctgcagac gtgctgtggg agccttgctt atgcagctcc tgaactaata   540
caagggaagt cgtaccttgg atcagaggca gatgtttgga gcatgggcat cctcctgtat   600
gtgctcatgt gtggatttct accatttgat gatgataatg tcatggcttt gtacaagaag   660
ataatgagag ggaaatacga agttcctaag tggctctctc ccagtagcat tctgcttctc   720
cagcagatgt tgcaggtgga cccaaagaaa cggatttcta tgagaaatct cctgaaccat   780
ccctgggtca tgcaagatta cagctgtccc gtggagtggc aaagcaagac tcctttgact   840
cacctcgatg aggattgcgt gacagagctt tctgtacatc accgcagcag caggcagaca   900
atggaggatt taatttcgtc gtggcagtac gatcacctca cagccaccta ccttctgctt   960
ctagccaaga aggcccgggg gaagccggct cgtctacagc tcctgtcctt ctcttgtgga  1020
accgccagca ccactccaaa gtcaaagaat ctgagcctgg aagatatgag cacaagtgat  1080
gataactgtg tggctggatt gatagactat gaattgtgtg aagataaatt attagctccc  1140
aagacgccac aggttaccaa acacttggca gaatcaaatc acgcagcatc taaatcacca  1200
gcgccagggg tacgcagagc agtggcaaat aaattaatgg acaaagaaaa tgtgtgcact  1260
cccaagtctt ctgtgaagaa tgaagagcag tttgtatttt ctgagccgaa gattccagtt  1320
agtaagaacc agtataagag agaaataccc gcctcaccaa cccgtttccc aacacctgca  1380
aaagctagag cccagtgcct gagagaagcc ccggttagaa caccagggaa ttccgcagga  1440
gcagacacac taacgacagg tgtcattagc cccgagagga ggtgccgttc aatggacgtg  1500
gatctcaacc aggcacacat ggaggatacc ccgaaaaaga aggaaccaa tgtgtttggg  1560
agccttgaga gaggactgga taaggttctc actgcgctca aaggaacaa gaagaagggc  1620
```

```
tctgccagag atggaccaag aaagcgaaag ctgcactaca atgtgactac aactcgcctg    1680
gtgaaccccg accagctcct gagcgaaatc atggctattc ttccaaagaa gaacgtggac    1740
ttcgtacaga aaggttacac tctaaagtgt caaacgcagt ctgattttgg caaagtgaca    1800
atgcagtttg aactggaagt gtgccagctg cagagacctg acgtggtagg catccggaga    1860
cagcggctga agggtgatgc ctgggtttac aagagattag tggaagatat cttgtctggc    1920
tgcaagatgt ga                                                         1932
```

```
<210> SEQ ID NO 20
<211> LENGTH: 643
<212> TYPE: PRT
<213> ORGANISM: Mus musculus

<400> SEQUENCE: 20
```

```
Met Lys Asp Tyr Asp Glu Leu Leu Lys Tyr Tyr Glu Leu Tyr Glu Thr
1               5                   10                  15

Ile Gly Thr Gly Gly Phe Ala Lys Val Lys Leu Ala Cys His Val Leu
            20                  25                  30

Thr Gly Glu Met Val Ala Ile Lys Ile Met Asp Lys Asn Ala Leu Gly
        35                  40                  45

Ser Asp Leu Pro Arg Val Lys Thr Glu Ile Asp Ala Leu Lys Ser Leu
    50                  55                  60

Arg His Gln His Ile Cys Gln Leu Tyr His Val Leu Glu Thr Lys Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Glu Thr Arg Val Val
            100                 105                 110

Phe Arg Gln Ile Leu Ser Ala Val Ala Tyr Val His Ser Gln Gly Tyr
        115                 120                 125

Ala His Arg Asp Leu Lys Pro Glu Asn Leu Leu Phe Asp Glu Asn His
    130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Glu Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Arg Asn
                245                 250                 255

Leu Leu Asn His Pro Trp Val Met Gln Asp Tyr Ser Cys Pro Val Glu
            260                 265                 270

Trp Gln Ser Lys Thr Pro Leu Thr His Leu Asp Glu Asp Cys Val Thr
        275                 280                 285

Glu Leu Ser Val His His Arg Ser Ser Arg Gln Thr Met Glu Asp Leu
    290                 295                 300

Ile Ser Ser Trp Gln Tyr Asp His Leu Thr Ala Thr Tyr Leu Leu Leu
305                 310                 315                 320
```

Leu Ala Lys Lys Ala Arg Gly Lys Pro Ala Arg Leu Gln Leu Leu Ser
             325                 330                 335

Phe Ser Cys Gly Thr Ala Ser Thr Thr Pro Lys Ser Lys Asn Leu Ser
            340                 345                 350

Leu Glu Asp Met Ser Thr Ser Asp Asp Asn Cys Val Ala Gly Leu Ile
        355                 360                 365

Asp Tyr Glu Leu Cys Glu Asp Lys Leu Leu Ala Pro Lys Thr Pro Gln
    370                 375                 380

Val Thr Lys His Leu Ala Glu Ser Asn His Ala Ala Ser Lys Ser Pro
385                 390                 395                 400

Ala Pro Gly Val Arg Arg Ala Val Ala Asn Lys Leu Met Asp Lys Glu
                405                 410                 415

Asn Val Cys Thr Pro Lys Ser Ser Val Lys Asn Glu Glu Gln Phe Val
            420                 425                 430

Phe Ser Glu Pro Lys Ile Pro Val Ser Lys Asn Gln Tyr Lys Arg Glu
        435                 440                 445

Ile Pro Ala Ser Pro Thr Arg Phe Pro Thr Pro Ala Lys Ala Arg Ala
    450                 455                 460

Gln Cys Leu Arg Glu Ala Pro Val Arg Thr Pro Gly Asn Ser Ala Gly
465                 470                 475                 480

Ala Asp Thr Leu Thr Thr Gly Val Ile Ser Pro Glu Arg Arg Cys Arg
                485                 490                 495

Ser Met Asp Val Asp Leu Asn Gln Ala His Met Glu Asp Thr Pro Lys
            500                 505                 510

Lys Lys Gly Thr Asn Val Phe Gly Ser Leu Glu Arg Gly Leu Asp Lys
        515                 520                 525

Val Leu Thr Ala Leu Thr Arg Asn Lys Lys Lys Gly Ser Ala Arg Asp
    530                 535                 540

Gly Pro Arg Lys Arg Lys Leu His Tyr Asn Val Thr Thr Thr Arg Leu
545                 550                 555                 560

Val Asn Pro Asp Gln Leu Leu Ser Glu Ile Met Ala Ile Leu Pro Lys
                565                 570                 575

Lys Asn Val Asp Phe Val Gln Lys Gly Tyr Thr Leu Lys Cys Gln Thr
            580                 585                 590

Gln Ser Asp Phe Gly Lys Val Thr Met Gln Phe Glu Leu Glu Val Cys
        595                 600                 605

Gln Leu Gln Arg Pro Asp Val Val Gly Ile Arg Gln Arg Leu Lys
    610                 615                 620

Gly Asp Ala Trp Val Tyr Lys Arg Leu Val Glu Asp Ile Leu Ser Gly
625                 630                 635                 640

Cys Lys Met

<210> SEQ ID NO 21
<211> LENGTH: 1836
<212> TYPE: DNA
<213> ORGANISM: Homo sapiens

<400> SEQUENCE: 21
atggcggcct cagcaaaaaa gaagaataag aaggggaaga ctatctccct aacagacttt      60
ctggctgagg atgggggtac tggtggagga agcacctatg tttccaaacc agtcagctgg     120
gctgatgaaa cggatgacct ggaaggagat gtttcgacca cttggcacag taacgatgac     180
gatgtgtata gggcgcctcc aattgaccgt tccatccttc ccactgctcc acgggctgct     240

| | |
|---|---|
| cgggaaccca atatcgaccg agccgtcctt cccaaatcgc caccctacac tgctttttcta | 300 |
| ggaaacctac cctatgatgt tacagaagag tcaattaagg aattctttcg aggattaaat | 360 |
| atcagtgcag tgcgtttacc acgtgaaccc agcaatccag agaggttgaa aggttttggt | 420 |
| tatgctgaat ttgaggacct ggattccctg ctcagtgccc tgagtctcaa tgaagagtct | 480 |
| ctaggtaaca ggagaattcg agtggacgtt gctgatcaag cacaggataa agacagggat | 540 |
| gatcgttctt ttggccgtga tagaaatcgg gattctgaca aaacagatac agactggagg | 600 |
| gctcgtcctg ctacagacag ctttgatgac tacccaccta gaagaggtga tgatagcttt | 660 |
| ggagacaagt atcgagatcg ttatgattca gaccggtatc gggatgggta tcggatgggg | 720 |
| tatcgggatg gcccacgccg ggatatggat cgatatggtg gccgggatcg ctatgatgac | 780 |
| cgaggcagca gagactatga tagaggctat gattcccgga taggcagtgg cagaagagca | 840 |
| tttggcagtg ggtatcgcag ggatgatgac tacagaggag gcggggaccg ctatgaagac | 900 |
| cgatatgaca gacgggatga tcggtcgtgg agctccagag atgattactc tcgggatgat | 960 |
| tataggcgtg atgatagagg tccccccccaa agacccaaac tgaatctaaa gcctcggagt | 1020 |
| actcctaagg aagatgattc ctctgctagt acctcccagt ccactcgagc tgcttctatc | 1080 |
| tttggagggg caaagcctgt tgacacagct gctagaaaaa gagaagtaga agaacggcta | 1140 |
| cagaaggaac aagagaagtt gcagcgtcag ctggatgagc caaaactaga acgacggcct | 1200 |
| cgggagagac acccaagctg gcgaagtgaa gaaactcagg aacgggaacg gtcgaggaca | 1260 |
| ggaagtgagt catcacaaac tgggacctcc accacatcta gcagaaatgc acgaaggaga | 1320 |
| gagagtgaga agtctctaga aaatgaaaca ctcaataagg aggaagattg ccactctcca | 1380 |
| acttctaaac ctcccaaacc tgatcagccc ctaaaggtaa tgccagcccc tccaccaaag | 1440 |
| gagaatgctt gggtgaagcg aagttctaac cctcctgctc gatctcagag ctcagacaca | 1500 |
| gagcagcagt ccctacaag tggtggggga aaagtagctc cagctcaacc atctgaggaa | 1560 |
| ggaccaggaa ggaaagatga aaataaagta gatgggatga atgccccaaa aggccaaact | 1620 |
| gggaactcta gccgtggtcc aggagacgga gggaacagag accactggaa ggagtcagat | 1680 |
| aggaaagatg gcaaaaagga tcaagactcc agatctgcac ctgagccaaa gaaacctgag | 1740 |
| gaaaatccag cttccaagtt cagttctgca agcaagtatg ctgctctctc tgttgatggt | 1800 |
| gaagatgaaa atgagggaga agattatgcc gaatag | 1836 |

<210> SEQ ID NO 22
<211> LENGTH: 611
<212> TYPE: PRT
<213> ORGANISM: Homo sapiens

<400> SEQUENCE: 22

Met Ala Ala Ser Ala Lys Lys Asn Lys Lys Gly Lys Thr Ile Ser
1               5                   10                  15

Leu Thr Asp Phe Leu Ala Glu Asp Gly Thr Gly Gly Ser Thr
            20                  25                  30

Tyr Val Ser Lys Pro Val Ser Trp Ala Asp Glu Thr Asp Leu Glu
        35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

```
Thr Ala Phe Leu Gly Asn Leu Pro Tyr Asp Val Thr Glu Ser Ile
            100                 105                 110

Lys Glu Phe Phe Arg Gly Leu Asn Ile Ser Ala Val Arg Leu Pro Arg
                115                 120                 125

Glu Pro Ser Asn Pro Glu Arg Leu Lys Gly Phe Gly Tyr Ala Glu Phe
        130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
        195                 200                 205

Asp Asp Tyr Pro Pro Arg Arg Gly Asp Asp Ser Phe Gly Asp Lys Tyr
        210                 215                 220

Arg Asp Arg Tyr Asp Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
            260                 265                 270

Arg Ile Gly Ser Gly Arg Arg Ala Phe Gly Ser Gly Tyr Arg Arg Asp
        275                 280                 285

Asp Asp Tyr Arg Gly Gly Asp Arg Tyr Glu Asp Arg Tyr Asp Arg
        290                 295                 300

Arg Asp Asp Arg Ser Trp Ser Ser Arg Asp Asp Tyr Ser Arg Asp Asp
305                 310                 315                 320

Tyr Arg Arg Asp Asp Arg Gly Pro Pro Gln Arg Pro Lys Leu Asn Leu
                325                 330                 335

Lys Pro Arg Ser Thr Pro Lys Glu Asp Asp Ser Ser Ala Ser Thr Ser
            340                 345                 350

Gln Ser Thr Arg Ala Ala Ser Ile Phe Gly Gly Ala Lys Pro Val Asp
        355                 360                 365

Thr Ala Ala Arg Glu Arg Glu Val Glu Glu Arg Leu Gln Lys Glu Gln
        370                 375                 380

Glu Lys Leu Gln Arg Gln Leu Asp Glu Pro Lys Leu Glu Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Thr Ser Thr Thr
            420                 425                 430

Ser Ser Arg Asn Ala Arg Arg Glu Ser Glu Lys Ser Leu Glu Asn
        435                 440                 445

Glu Thr Leu Asn Lys Glu Glu Asp Cys His Ser Pro Thr Ser Lys Pro
        450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Gln Ser Pro Thr Ser Gly Gly Gly Lys Val
            500                 505                 510
```

```
Ala Pro Ala Gln Pro Ser Glu Glu Gly Pro Gly Arg Lys Asp Glu Asn
            515                 520                 525

Lys Val Asp Gly Met Asn Ala Pro Lys Gly Gln Thr Gly Asn Ser Ser
        530                 535                 540

Arg Gly Pro Gly Asp Gly Gly Asn Arg Asp His Trp Lys Glu Ser Asp
545                 550                 555                 560

Arg Lys Asp Gly Lys Lys Asp Gln Asp Ser Arg Ser Ala Pro Glu Pro
            565                 570                 575

Lys Lys Pro Glu Glu Asn Pro Ala Ser Lys Phe Ser Ser Ala Ser Lys
                580                 585                 590

Tyr Ala Ala Leu Ser Val Asp Gly Glu Asp Asn Glu Gly Glu Asp
            595                 600                 605

Tyr Ala Glu
    610

<210> SEQ ID NO 23
<211> LENGTH: 1836
<212> TYPE: DNA
<213> ORGANISM: Mus musculus

<400> SEQUENCE: 23
atggcggcct cagcaaaaaa gaagaataag aaggggaaga ccatctccct aacggacttt      60
ctagctgagg atggaggaac tggtggagga agcacctatg tccccaaacc agtcagctgg    120
gctgatgaaa cagacgatct ggaaggagat gtgtcaacaa cttggcatag taacgatgat    180
gacgtgtaca gggcgcctcc aattgaccgt tccatccttc ccactgctcc acgggctgct    240
cgggaaccca atattgaccg gagccgtctt cccaagtcgc caccctacac tgctttccta    300
gggaatctgc cctatgatgt gacagaagac tccattaagg atttctttag aggattaaat    360
atcagcgctg tacgcttacc acgggaaccc agcaatccag acaggttgaa aggtttcggc    420
tacgcagaat ttgaggacct ggattctctg ctcagtgctc tgagtctcaa tgaagagtct    480
ctaggtaaca ggagaattcg tgtggatgtt gctgatcaag cacaggataa agacagggat    540
gaccgttctt ttggtcgaga tagaaatcgg gattctgaca aaacagacac agactggagg    600
gcccgtccca ccacagacag ttttgatgac tacccaccta agagaggcga tgatagcttc    660
ggagacaagt atcgagatcg ttacgattca gaccggtatc gggatgggta tagggacgga    720
tatcgggacg gcccacgcag agacatggac cgctatgggg gccgggatcg ctatgatgac    780
cgaggcagca gagactatga ccgaggctat gactccagga taggcagtgg cagaagggca    840
tttggaagtg ggtaccggag agatgatgac tacagaggag gtgggaccg ctatgaagac    900 cgctatgaca gacgggatga tcggtcgtgg agctccaggg atgactactc tcgggatgat    960
tataggcgtg atgacagagg tcccccccag agacccagac tgaacctcaa gcctcgaagc   1020
gctcctaagg aggatgacgc ctccgccagc acctcccagt ccagccgggc agcctccatc   1080 tttgagggg cgaagcctgt tgacacagct gctaggaaa gagaagtaga ggagcggcta    1140
cagaaggagc aggagaagct gcagcgtcag ctggatgagc aaaactaga ccgccggccc    1200 cgggagagac acccaagctg gcgaagtgaa gaaactcagg aaagagaacg gtcaaggaca   1260
ggaagtgagt catcgcagac tggggcctca gccacatctg gcagaaatac acgaaggaga   1320
gagagtgaga agtctctaga aaatgaaacc ctcaataaag aagaagactg tcactctcca   1380
acctctaagc ctcctaaacc tgaccagcct ctaaaggtaa tgccagcccc tccaccaaag   1440
gagaatgcgt gggtgaagcg aagctctaac cctcctgccc gatctcagag ctcagacaca   1500
```

-continued

```
gagcagccgt ccctacaag tggtggaggg aaagtagctg cagtccagcc ccctgaggaa    1560
ggaccatcaa gaaagatgg aaataaagtg gatgtggtgg gtgccacaca aggccaagct    1620
ggaagctgca gccgtggtcc cggggatgga gggagcagag accactggaa ggacttggat    1680
aggaaggatg gcaaaaaaga tcaagactcc agatctgcgc ctgagccaaa gaaacctgag    1740
gagaacccag cctctaagtt cagctctgca agcaagtacg ctgctctgtc tgtggatggc    1800
gaggatgagg atgagggcga cgactgcact gagtag                             1836
```

<210> SEQ ID NO 24
<211> LENGTH: 611
<212> TYPE: PRT
<213> ORGANISM: Mus musculus

<400> SEQUENCE: 24

```
Met Ala Ala Ser Ala Lys Lys Asn Lys Lys Gly Lys Thr Ile Ser
1               5                   10                  15

Leu Thr Asp Phe Leu Ala Glu Asp Gly Gly Thr Gly Gly Ser Thr
            20                  25                  30

Tyr Val Pro Lys Pro Val Ser Trp Ala Asp Glu Thr Asp Asp Leu Glu
        35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
            100                 105                 110

Lys Asp Phe Phe Arg Gly Leu Asn Ile Ser Ala Val Arg Leu Pro Arg
        115                 120                 125

Glu Pro Ser Asn Pro Asp Arg Leu Lys Gly Phe Gly Tyr Ala Glu Phe
    130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Thr Thr Asp Ser Phe
        195                 200                 205

Asp Asp Tyr Pro Pro Arg Arg Gly Asp Asp Ser Phe Gly Asp Lys Tyr
    210                 215                 220

Arg Asp Arg Tyr Asp Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
            260                 265                 270

Arg Ile Gly Ser Gly Arg Arg Ala Phe Gly Ser Gly Tyr Arg Arg Asp
        275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320
```

Tyr Arg Arg Asp Asp Arg Gly Pro Pro Gln Arg Pro Arg Leu Asn Leu
                325                 330                 335

Lys Pro Arg Ser Ala Pro Lys Glu Asp Ala Ser Ala Ser Thr Ser
            340                 345                 350

Gln Ser Ser Arg Ala Ala Ser Ile Phe Gly Gly Ala Lys Pro Val Asp
        355                 360                 365

Thr Ala Ala Arg Glu Arg Glu Val Glu Glu Arg Leu Gln Lys Glu Gln
    370                 375                 380

Glu Lys Leu Gln Arg Gln Leu Asp Glu Pro Lys Leu Asp Arg Arg Pro
385                 390                 395                 400

Arg Glu Arg His Pro Ser Trp Arg Ser Glu Thr Gln Glu Arg Glu
                405                 410                 415

Arg Ser Arg Thr Gly Ser Glu Ser Ser Gln Thr Gly Ala Ser Ala Thr
            420                 425                 430

Ser Gly Arg Asn Thr Arg Arg Glu Ser Glu Lys Ser Leu Glu Asn
        435                 440                 445

Glu Thr Leu Asn Lys Glu Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Pro Ser Pro Thr Ser Gly Gly Gly Lys Val
            500                 505                 510

Ala Ala Val Gln Pro Pro Glu Gly Pro Ser Arg Lys Asp Gly Asn
        515                 520                 525

Lys Val Asp Val Val Gly Ala Thr Gln Gly Gln Ala Gly Ser Cys Ser
    530                 535                 540

Arg Gly Pro Gly Asp Gly Gly Ser Arg Asp His Trp Lys Asp Leu Asp
545                 550                 555                 560

Arg Lys Asp Gly Lys Lys Asp Gln Asp Ser Arg Ser Ala Pro Glu Pro
                565                 570                 575

Lys Lys Pro Glu Glu Asn Pro Ala Ser Lys Phe Ser Ser Ala Ser Lys
            580                 585                 590

Tyr Ala Ala Leu Ser Val Asp Gly Glu Asp Glu Asp Glu Gly Asp Asp
        595                 600                 605

Cys Thr Glu
    610

<210> SEQ ID NO 25
<211> LENGTH: 2090
<212> TYPE: DNA
<213> ORGANISM: Macaca mulatta

<400> SEQUENCE: 25
ctctcccaac atggcggcct cagcaaaaaa gaagaataag aaggggaaga ctatctccct        60
aacagacttt ctggctgagg atggggtac tggtggagga agcacctatg tttccaaacc       120
agtcagctgg gctgatgaaa cggatgacct ggaaggagat gtttcaacaa cgtggcacag      180
taatgacgac gatgtgtaca gggcgcctcc aattgaccgt ccatccttc ccactgctcc       240 acgggctgct cgggaaccca atatcgaccg gagccgtctt cccaaatcgc accctacac       300 tgcttttcta gggaacctac cctatgatgt gacagaagaa tcaattaagg aattctttag      360
aggattaaat atcagtgcag tgcgtttacc acgtgaaccc agcaatccag agaggttgaa       420

```
aggttttggt tatgctgaat ttgaggacct ggattccctg ctcagtgccc tgagtctcaa    480
tgaagagtct ctaggtaaca ggagaattcg agtggacgtt gctgatcaag cacaggataa    540
agacagggat gatcgttctt ttggccgtga tagaaatcgg gattctgaca aaacagatac    600
agactggagg gctcgtcctg ctacagacag ctttgatgac tacccaccta agagaggtga    660
tgatagcttt ggagacaagt atcgagatcg ttatgattca gaccggtatc gggatgggta    720
tcgggatggc ccacgccggg atatggatcg atatggtggc cgggatcgct atgatgaccg    780
aggcagcaga gactatgata gaggctatga ttcccggata ggcagtggca gaagagcatt    840
tggcagtggg tatcgcaggg atgatgacta cagaggaggc gggaccgat atgaagaccg      900
atacgacaga cggatgatc ggtcgtggag ctccagagat gattactctc gggatgatta      960
taggcgcgat gacagaggtc cccctcaaag acccaaactg aatctaaagc ctcggagtac   1020
tcctaaggaa gatgattcct ctgctagtac ctcccagtcc agtcgagctg cttctatctt   1080
tggaggggca aagcctgttg acacagctgc tagagaaaga gaagtagaag aacggctaca   1140
gaaggaacaa gagaagttgc agcgtcagct ggatgagcca aaactagaac gacggcctcg   1200
ggagagacac ccaagctggc gaagtgaaga aactcaggaa cgggaacggt cgaggacagg   1260
aagtgagtca tcacagactg ggacctccgc cacatctggc agaaatgcac gaaggagaga   1320
gagtgagaag tctctagaaa atgaaacact caataaggag gaagattgtc actctccaac   1380
ttctaaacct cccaaacctg atcagcccct aaaggtaatg ccagcccctc caccaaagga   1440
gaatgcttgg gtgaagcgaa gttctaaccc tccagctcga tctcagagct cagacacaga   1500
gcagcaatcc cctacaagtg gtggggaaa agtagctcca gctcaaccat ctgaggaagg    1560
accagcaagg aaagatgaaa ataaagtaga tgggatgaat gtcccaaaag gccaaactgg   1620
gacctctagc cgtggaccag agacggagg gaacaaagac cactggaagg agtcagatag    1680
gaaagatggc aaaaaggatc aagactccag atctgcacct gagccaaaga aacctgagga   1740
aaatccagct tcgaagttca gttctgcaag caagtatgct gctctctctg ttgatggtga   1800
agatgaaaac gagggagaag attatgccga atagacctct acatcctgtg ctttctccta   1860
gtttctctcc accctggaac attcgagagc aaatcaaaac ctctatccag acaagacaaa   1920
ataaaactca ccatctcctg aagacctttc ttacctttt ttaaaaacaa aaaatgaaat    1980
tattttgcat gctgctgcag cctttaaagt attaaagtaa ctgagaatc gccaatatag     2040
ccagagagaa agggactaca gctttttaga ggaagagttg tggtgtgtta              2090
```

<210> SEQ ID NO 26
<211> LENGTH: 607
<212> TYPE: PRT
<213> ORGANISM: Macaca mulatta

<400> SEQUENCE: 26

```
Met Ala Ala Ser Ala Lys Lys Lys Asn Lys Lys Gly Lys Thr Ile Ser
1               5                   10                  15

Leu Thr Asp Phe Leu Ala Glu Asp Gly Gly Thr Gly Gly Gly Ser Thr
            20                  25                  30

Tyr Val Ser Lys Pro Val Ser Trp Ala Asp Glu Thr Asp Asp Leu Glu
        35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80
```

-continued

```
Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Glu Ser Ile
            100                 105                 110

Lys Glu Phe Phe Arg Gly Leu Asn Ile Ser Ala Val Arg Leu Pro Arg
        115                 120                 125

Glu Pro Ser Asn Pro Glu Arg Leu Lys Gly Phe Gly Tyr Ala Glu Phe
130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
        195                 200                 205

Asp Asp Tyr Pro Pro Arg Arg Gly Asp Asp Ser Phe Gly Asp Lys Tyr
210                 215                 220

Arg Asp Arg Tyr Asp Ser Asp Arg Tyr Arg Asp Gly Tyr Arg Asp Gly
225                 230                 235                 240

Pro Arg Arg Asp Met Asp Arg Tyr Gly Gly Arg Asp Arg Tyr Asp Asp
                245                 250                 255

Arg Gly Ser Arg Asp Tyr Asp Arg Gly Tyr Asp Ser Arg Ile Gly Ser
            260                 265                 270

Gly Arg Ala Phe Gly Ser Gly Tyr Arg Asp Asp Asp Tyr Arg
        275                 280                 285

Gly Gly Gly Asp Arg Tyr Glu Asp Arg Tyr Asp Arg Asp Arg
290                 295                 300

Ser Trp Ser Ser Arg Asp Asp Tyr Ser Arg Asp Asp Tyr Arg Arg Asp
305                 310                 315                 320

Asp Arg Gly Pro Pro Gln Arg Pro Lys Leu Asn Leu Lys Pro Arg Ser
                325                 330                 335

Thr Pro Lys Glu Asp Asp Ser Ser Ala Ser Thr Ser Gln Ser Ser Arg
            340                 345                 350

Ala Ala Ser Ile Phe Gly Gly Ala Lys Pro Val Asp Thr Ala Ala Arg
        355                 360                 365

Glu Arg Glu Val Glu Glu Arg Leu Gln Lys Glu Gln Glu Lys Leu Gln
370                 375                 380

Arg Gln Leu Asp Glu Pro Lys Leu Glu Arg Pro Arg Glu Arg His
385                 390                 395                 400

Pro Ser Trp Arg Ser Glu Glu Thr Gln Glu Arg Glu Arg Ser Arg Thr
                405                 410                 415

Gly Ser Glu Ser Ser Gln Thr Gly Thr Ser Ala Thr Ser Gly Arg Asn
            420                 425                 430

Ala Arg Arg Arg Glu Ser Glu Lys Ser Leu Glu Asn Glu Thr Leu Asn
        435                 440                 445

Lys Glu Glu Asp Cys His Ser Pro Thr Ser Lys Pro Pro Lys Pro Asp
450                 455                 460

Gln Pro Leu Lys Val Met Pro Ala Pro Pro Lys Glu Asn Ala Trp
465                 470                 475                 480

Val Lys Arg Ser Ser Asn Pro Pro Ala Arg Ser Gln Ser Ser Asp Thr
                485                 490                 495
```

```
Glu Gln Gln Ser Pro Thr Ser Gly Gly Gly Lys Val Ala Pro Ala Gln
            500                 505                 510

Pro Ser Glu Glu Gly Pro Ala Arg Lys Asp Glu Asn Lys Val Asp Gly
        515                 520                 525

Met Asn Val Pro Lys Gly Gln Thr Gly Thr Ser Ser Arg Gly Pro Gly
        530                 535                 540

Asp Gly Gly Asn Lys Asp His Trp Lys Glu Ser Asp Arg Lys Asp Gly
545                 550                 555                 560

Lys Lys Asp Gln Asp Ser Arg Ser Ala Pro Glu Pro Lys Lys Pro Glu
                565                 570                 575

Glu Asn Pro Ala Ser Lys Phe Ser Ser Ala Ser Lys Tyr Ala Ala Leu
        580                 585                 590

Ser Val Asp Gly Glu Asp Glu Asn Glu Gly Glu Asp Tyr Ala Glu
        595                 600                 605

<210> SEQ ID NO 27
<211> LENGTH: 1833
<212> TYPE: DNA
<213> ORGANISM: Bos taurus

<400> SEQUENCE: 27
atggcggcct cagcgaaaaa gaagaataag aaggggaaga ctatctccct aacagacttt        60
ctggctgagg atggagggac tggtggaggc agcacctatg tccccaaacc agtcagctgg       120
gctgatgaaa cagacgatct ggaaggggat gtttcaacca cttggcatag taatgatgat       180
gatgtgtatc gggcacctcc aattgaccgt tccatcctgc ccactgctcc acgggctgct       240
cgggaaccca atatcgaccg gagccgtctt cccaaatctc caccctacac tgctttttcta      300 gggaacctgc cctatgatgt gacagaagac tccattaagg aattctttag aggattaaat       360
atcagtgcag tgcgtttacc gcgtgaaccc agcaatcctg agaggttaaa aggttttggt       420
tatgcagagt ttgaggacct ggattccttg ctcagtgcct tgagcctcaa cgaagagtct       480
ctaggtaaca ggagaattcg agtggacgtt gctgatcaag cacaggataa agacagggat       540
gatcgttctt ttggccgaga tagaaatcgt gattctgaca aaacagatac agactggagg       600
gcccgtcctg ctgcagacag ctttgatgac taccgcccca aaggggtgat gatagcttt        660 ggagacaagt atcgagatcg ttacgattca gacagatatc gtgatgggta cgggacagt        720 taccgtgatg gcccacgccg ggacatggat cgatacgggg gccgagatcg ctatgatgac       780
cgaggtggca gagactatga cagaggctac gattccagga taggcagtgg cagaagagca       840
ttcggtagcg gtaccggag gatgatgac tacagaggag gcgggaccg ctatgaagac          900 agatacgaca gacgagatga ccggtcctgg agttccagag atgattactc tcgggatgat       960
tacaggcggg atgatagagg tccccctcaa agacccaaac tgaacctaaa gcctcggagt      1020
actcctaagg aagatgattc ctccgctagc acctcccagt ccagtcgtgc agcctctatc      1080
tttgaggggg caaagcctgt tgacacagct gctagagaac gagaagtaga gagcggcta       1140 cagaaggaac aggagaaact gcagcgtcag ctggatgagc aaaactaga acgacggcct      1200 cgggagagac acccaagctg gcgaagtgaa gaaactcagg aacgggaacg atcgaggaca      1260
ggaagtgagt catcacagac tgggacctca gccacatctg gcagaaatgc aagaagaaga      1320
gagagtgaga agtctttaga aaatgaaacc cccaataaag aggaagactg tcagtctcca      1380
acttctaagc ctcccaaacc tgaacagcct ctaaaggtaa tgccagcccc tccaccaaag      1440
gagaatgctt gggtgaagcg aagttctaac cctcctgctc gatctcagag ctcagacaca      1500
```

```
gagcagcagt cccctacaag tggtggaggg aaagtagttc cagctcaact atctgaggaa   1560
ggatcagcaa ggaaagatga aaataaagta gatggggtga gtgccccaaa aggccaaagt   1620
gggagctcca gccgtggtcc gggagatggg gggaacaaag accactggaa ggaggcagac   1680
aggaaagatg gcaaaaagga tcacgactcc agatctgcac ctgagccaaa gaaagctgaa   1740
gaaaatccag cctcgaagtt cagatctgca agcaagtacg ctactctcgc cattgacggt   1800
gaagatgaaa atgagggaga ttacaccgaa tag                                1833
```

<210> SEQ ID NO 28
<211> LENGTH: 610
<212> TYPE: PRT
<213> ORGANISM: Bos taurus

<400> SEQUENCE: 28

```
Met Ala Ala Ser Ala Lys Lys Asn Lys Gly Lys Thr Ile Ser
1               5                   10                  15

Leu Thr Asp Phe Leu Ala Glu Asp Gly Gly Thr Gly Gly Ser Thr
                20                  25                  30

Tyr Val Pro Lys Pro Val Ser Trp Ala Asp Glu Thr Asp Asp Leu Glu
            35                  40                  45

Gly Asp Val Ser Thr Thr Trp His Ser Asn Asp Asp Val Tyr Arg
        50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
                100                 105                 110

Lys Glu Phe Phe Arg Gly Leu Asn Ile Ser Ala Val Arg Leu Pro Arg
                115                 120                 125

Glu Pro Ser Asn Pro Glu Arg Leu Lys Gly Phe Gly Tyr Ala Glu Phe
            130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
                180                 185                 190

Asp Lys Thr Asp Thr Asp Trp Arg Ala Arg Pro Ala Ala Asp Ser Phe
            195                 200                 205

Asp Asp Tyr Pro Pro Arg Arg Gly Asp Asp Ser Phe Gly Asp Lys Tyr
    210                 215                 220

Arg Asp Arg Tyr Asp Ser Asp Tyr Arg Asp Gly Tyr Arg Asp Ser
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Gly Arg Asp Tyr Asp Arg Gly Tyr Asp Ser
                260                 265                 270

Arg Ile Gly Ser Gly Arg Arg Ala Phe Gly Ser Gly Tyr Arg Arg Asp
            275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320
```

Tyr Arg Arg Asp Asp Arg Gly Pro Pro Gln Arg Pro Lys Leu Asn Leu
            325                 330                 335

Lys Pro Arg Ser Thr Pro Lys Glu Asp Ser Ser Ala Ser Thr Ser
        340                 345                 350

Gln Ser Ser Arg Ala Ala Ser Ile Phe Gly Gly Ala Lys Pro Val Asp
            355                 360                 365

Thr Ala Ala Arg Glu Arg Glu Val Glu Glu Arg Leu Gln Lys Glu Gln
        370                 375                 380

Glu Lys Leu Gln Arg Gln Leu Asp Glu Pro Lys Leu Glu Arg Arg Pro
385                 390                 395                 400

Arg Glu Arg His Pro Ser Trp Arg Ser Glu Thr Gln Glu Arg Glu
                405                 410                 415

Arg Ser Arg Thr Gly Ser Glu Ser Ser Gln Thr Gly Thr Ser Ala Thr
            420                 425                 430

Ser Gly Arg Asn Ala Arg Arg Glu Ser Glu Lys Ser Leu Glu Asn
            435                 440                 445

Glu Thr Pro Asn Lys Glu Glu Asp Cys Gln Ser Pro Thr Ser Lys Pro
        450                 455                 460

Pro Lys Pro Glu Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Gln Ser Pro Thr Ser Gly Gly Gly Lys Val
            500                 505                 510

Val Pro Ala Gln Leu Ser Glu Gly Ser Ala Arg Lys Asp Glu Asn
            515                 520                 525

Lys Val Asp Gly Val Ser Ala Pro Lys Gly Gln Ser Gly Ser Ser Ser
530                 535                 540

Arg Gly Pro Gly Asp Gly Gly Asn Lys Asp His Trp Lys Glu Ala Asp
545                 550                 555                 560

Arg Lys Asp Gly Lys Lys Asp His Asp Ser Arg Ser Ala Pro Glu Pro
                565                 570                 575

Lys Lys Ala Glu Glu Asn Pro Ala Ser Lys Phe Arg Ser Ala Ser Lys
            580                 585                 590

Tyr Ala Thr Leu Ala Ile Asp Gly Glu Asp Glu Asn Glu Gly Asp Tyr
            595                 600                 605

Thr Glu
    610

<210> SEQ ID NO 29
<211> LENGTH: 1836
<212> TYPE: DNA
<213> ORGANISM: Rattus norvegicus

<400> SEQUENCE: 29
atggcggcct cagcaaaaaa gaagaataag aaggggaaga ccatctccct aacagacttt    60
ctagctgagg atgggggaac tggtggagga agcacctatg tccccaaacc agtcagctgg   120
gctgatgaaa cagacgatct ggaaggagat gtgtcaacaa cttggcatag taacgatgac   180
gatgtgtaca gggcacctcc tattgaccgt ccatccttc ccactgctcc acgggctgct   240
cgggaaccca atattgatcg gagccgtctt cccaagtcac caccctacac tgctttccta   300
gggaatctgc cctatgatgt gacagaagac tctattaagg atttctttag aggattaaat   360
atcagcgctg tacgcttgcc gcgtgagccc agcaatccag acaggttgaa aggttttggc   420

```
tatgccgaat tgaggatct ggattctctg ctcagtgctc tgagtctcaa tgaagagtct      480
ctaggtaaca ggagaattcg ggtggatgtt gctgatcaag cacaggataa agacagggat      540
gaccgttctt ttggtcgaga tagaaatcgg gattctgaca agacagacac agactggagg      600
gcccgtcctg ccacagacag ctttgatgac tacccaccta cgacgaggtga tgacagcttc     660 ggagacaagt atcgagatcg ttacgagtca gaccggtatc gggatgggta tagggacgga      720
tatcgggacg gcccacgcag agacatggac cgctatgggg gccgggatcg ctatgatgac      780
cgaggcagca gagactatga ccgaggctat gactccagga taggcagtgg cagaagagca      840
tttggaagtg ggtaccggag ggatgacgac tacagaggag gtggggaccg ctatgaagat      900
cgctatgaca gacgggacga tcggtcatgg agctccaggg acgattactc tcgggacgat      960
tacaggcgtg atgacagagg tcccccccaa agacccaaac tgaatctaaa gcctcggagt     1020
actcctaaag aagatgattc ctctgctagc acctcccagt ccagccgagc ggcttctatc     1080
tttggagggg cgaagcctgt tgacacagct gctagagaaa gagaagtaga ggagcggcta     1140
cagaaggagc aggagaagct gcagcgtcag ctggatgagc caaaactaga ccgccggccc     1200
cgggagagac acccaagttg gcgaagtgaa gaaactcagg aaagagaacg gtcgaggaca     1260
ggaagtgagt catcgcagac tgggacctca gccacatctg gcagaaatac acgaaggaga     1320
gagagtgaga agtctctaga aaatgaaacc ctcaataaag aagaagactg tcactctcca     1380
acctctaagc ctcctaaacc tgaccagcct ctaaaggtaa tgccagcccc tccaccaaag     1440
gagaatgcgt gggtgaagcg aagctctaac cctcctgctc gatctcagag ctcagacaca     1500
gagcagccgt cccctacaag tggtggaggg aaagttgctc cagctcagcc ctctgaggaa     1560
ggaccatcaa ggaaagatga aactaaagtg gatggggtga gcaccaccaa aggccagact     1620
ggacactcca gccgtggtcc tggggatgga gggagcagag accactggaa ggagttggat     1680
aggaaggacg gcaaaaaaga tcaagactcc agatctgcac ctgagccaaa gaaatctgag     1740
gagaaccgag cctctaagtt cagttctgca agcaagtacg ctgctctgtc tgtggacggt     1800
gaggatgagg atgagggaga cgactgcact gagtag                               1836
```

<210> SEQ ID NO 30
<211> LENGTH: 611
<212> TYPE: PRT
<213> ORGANISM: Rattus norvegicus

<400> SEQUENCE: 30

```
Met Ala Ala Ser Ala Lys Lys Lys Asn Lys Lys Gly Lys Thr Ile Ser
1               5                   10                  15

Leu Thr Asp Phe Leu Ala Glu Asp Gly Gly Thr Gly Gly Gly Ser Thr
            20                  25                  30

Tyr Val Pro Lys Pro Val Ser Trp Ala Asp Glu Thr Asp Asp Leu Glu
        35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
            100                 105                 110

Lys Asp Phe Phe Arg Gly Leu Asn Ile Ser Ala Val Arg Leu Pro Arg
```

```
            115                 120                 125
Glu Pro Ser Asn Pro Asp Arg Leu Lys Gly Phe Gly Tyr Ala Glu Phe
    130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
        195                 200                 205

Asp Asp Tyr Pro Pro Arg Arg Gly Asp Asp Ser Phe Gly Asp Lys Tyr
    210                 215                 220

Arg Asp Arg Tyr Glu Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Arg Gly Tyr Asp Ser
            260                 265                 270

Arg Ile Gly Ser Gly Arg Arg Ala Phe Gly Ser Gly Tyr Arg Arg Asp
        275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320

Tyr Arg Arg Asp Asp Arg Gly Pro Pro Gln Arg Pro Lys Leu Asn Leu
                325                 330                 335

Lys Pro Arg Ser Thr Pro Lys Glu Asp Asp Ser Ser Ala Ser Thr Ser
            340                 345                 350

Gln Ser Ser Arg Ala Ala Ser Ile Phe Gly Gly Ala Lys Pro Val Asp
        355                 360                 365

Thr Ala Ala Arg Glu Arg Glu Val Glu Glu Arg Leu Gln Lys Glu Gln
    370                 375                 380

Glu Lys Leu Gln Arg Gln Leu Asp Glu Pro Lys Leu Asp Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Thr Ser Ala Thr
            420                 425                 430

Ser Gly Arg Asn Thr Arg Arg Glu Ser Glu Lys Ser Leu Glu Asn
        435                 440                 445

Glu Thr Leu Asn Lys Glu Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Pro Ser Pro Thr Ser Gly Gly Lys Val
            500                 505                 510

Ala Pro Ala Gln Pro Ser Glu Glu Gly Pro Ser Arg Lys Asp Glu Thr
        515                 520                 525

Lys Val Asp Gly Val Ser Thr Thr Lys Gly Gln Thr Gly His Ser Ser
    530                 535                 540
```

```
Arg Gly Pro Gly Asp Gly Ser Arg Asp His Trp Lys Glu Leu Asp
545                 550                 555                 560

Arg Lys Asp Gly Lys Asp Gln Asp Ser Arg Ser Ala Pro Glu Pro
                565                 570                 575

Lys Lys Ser Glu Glu Asn Arg Ala Ser Lys Phe Ser Ala Ser Lys
                580                 585                 590

Tyr Ala Ala Leu Ser Val Asp Gly Glu Asp Glu Asp Gly Asp Asp
            595                 600                 605

Cys Thr Glu
    610

<210> SEQ ID NO 31
<211> LENGTH: 136
<212> TYPE: PRT
<213> ORGANISM: Homo sapiens

<400> SEQUENCE: 31

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 32
<211> LENGTH: 136
<212> TYPE: PRT
<213> ORGANISM: Mus musculus

<400> SEQUENCE: 32

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Tyr Leu Val Gly Leu Phe Glu Asp Thr Asn Leu Cys Ala
            100                 105                 110
```

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 33
<211> LENGTH: 136
<212> TYPE: PRT
<213> ORGANISM: Homo sapiens

<400> SEQUENCE: 33

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 34
<211> LENGTH: 136
<212> TYPE: PRT
<213> ORGANISM: Mus musculus

<400> SEQUENCE: 34

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ala
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135

<210> SEQ ID NO 35

```
<211> LENGTH: 136
<212> TYPE: PRT
<213> ORGANISM: Homo sapiens

<400> SEQUENCE: 35

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 36
<211> LENGTH: 136
<212> TYPE: PRT
<213> ORGANISM: Mus musculus

<400> SEQUENCE: 36

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135

<210> SEQ ID NO 37
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
```

```
atggcggcct cagcaaaaaa g                                              21
```

<210> SEQ ID NO 38
<211> LENGTH: 20
<212> TYPE: DNA
<213> ORGANISM: Artificial Sequence
<220> FEATURE:
<223> OTHER INFORMATION: /note="Description of Artificial Sequence:
     Synthetic primer"

<400> SEQUENCE: 38

```
ctattcggca taatcttctc                                                20
```

<210> SEQ ID NO 39
<211> LENGTH: 21
<212> TYPE: DNA
<213> ORGANISM: Artificial Sequence
<220> FEATURE:
<223> OTHER INFORMATION: /note="Description of Artificial Sequence:
     Synthetic shRNA"

<400> SEQUENCE: 39

```
gtggactctt gaaagtacta t                                              21
```

<210> SEQ ID NO 40
<211> LENGTH: 21
<212> TYPE: DNA
<213> ORGANISM: Artificial Sequence
<220> FEATURE:
<223> OTHER INFORMATION: /note="Description of Artificial Sequence:
     Synthetic shRNA"

<400> SEQUENCE: 40

```
ggaccaggaa ggaaagatga a                                              21
```

<210> SEQ ID NO 41
<211> LENGTH: 21
<212> TYPE: DNA
<213> ORGANISM: Artificial Sequence
<220> FEATURE:
<223> OTHER INFORMATION: /note="Description of Artificial Sequence:
     Synthetic shRNA"

<400> SEQUENCE: 41

```
gcggagaaac accttgatct t                                              21
```

<210> SEQ ID NO 42
<211> LENGTH: 16
<212> TYPE: PRT
<213> ORGANISM: Artificial Sequence
<220> FEATURE:
<223> OTHER INFORMATION: /note="Description of Artificial Sequence:
     Synthetic scanning peptide"
<220> FEATURE:
<221> NAME/KEY: VARIANT
<222> LOCATION: (3)..(7)
<223> OTHER INFORMATION: Xaa at these positions can be any amino acid
<220> FEATURE:
<221> NAME/KEY: VARIANT
<222> LOCATION: (8)..(8)
<223> OTHER INFORMATION: Xaa at this position can be Ser or Thr
<220> FEATURE:
<221> NAME/KEY: VARIANT
<222> LOCATION: (9)..(12)
<223> OTHER INFORMATION: Xaa at these positions can be any amino acid

<400> SEQUENCE: 42

Tyr Ala Xaa Xaa Xaa Xaa Xaa Xaa Xaa Xaa Xaa Xaa Ala Gly Lys Lys
1               5                   10                  15

```
<210> SEQ ID NO 43
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic eIF4B peptide"

<400> SEQUENCE: 43

Arg Glu Arg His Pro Ser Trp Arg Ser Glu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic eIF4B peptide"

<400> SEQUENCE: 44

Arg Glu Arg Ser Thr Ser Arg Lys Pro Ser
1               5                   10

<210> SEQ ID NO 45
<211> LENGTH: 16
<212> TYPE: PRT
<213> ORGANISM: Artificial Sequence
<220> FEATURE:
<223> OTHER INFORMATION: /note="Description of Artificial Sequence:
      Synthetic Histone H3 peptide"

<400> SEQUENCE: 45

Met Ala Arg Thr Lys Gln Thr Ala Arg Lys Ser Thr Gly Gly Lys Ala
1               5                   10                  15
```

BIOMARKER FOR MELK ACTIVITY AND METHODS OF USING SAME

CROSS-REFERENCE TO RELATED APPLICATIONS

This application claims the benefit of U.S. Provisional Application No. 61/954,046, filed on 17 Mar. 2014, and 61/902,877, filed on 12 Nov. 2013; the entire contents of each of said applications is incorporated herein in its entirety by this reference.

BACKGROUND OF THE INVENTION

The protein kinase, maternal embryonic leucine zipper kinase (MELK), is known to be involved in regulating cell cycle progression, cellular proliferation, apoptosis, and mRNA splicing (Badouel et al. (2006) Cell Cycle 5:883-889 and Badouel et al. (2010) Exp. Cell Res. 316:2166-2173). MELK has also been identified using gene expression profile analyses to be associated with a number of cancers, including breast, lung, bladder, lymphoma, and cervical cancer cells and mammary tumor formation in animal models (Komatsu et al. (2013) Int. J. Oncol. 42:478-506; Pickard et al. (2009) Breast Cancer Res. 11:R60; Hebbard et al. (2010) Cancer Res. 70:8863-8873; Lin et al. (2007) Breast Cancer Res. 9:R17; WO 2004/031413; WO 2007/7013665; and WO 2006/085684). Despite this association, however, functional analyses of MELK-mediated oncogenesis have not been performed to date and the mechanisms of MELK-mediated oncogenesis and, by extension, assays for determining agents useful in regulating such oncogenesis, are not known. This lack of understanding has prevented the identification of biomarkers that reliably report MELK enzymatic and/or oncogenic activity. While certain MELK-targeting inhibitors of kinase activity are known (see, for example, Chung et al. (2012) Oncotarget 3:1629-1640), there is a clear need in the art to identify biomarkers of MELK-mediated oncogenesis in order to provide rapid and effective means for evaluating MELK-targeted anti-cancer therapies.

SUMMARY OF THE INVENTION

The present invention is based, at least in part, on the discovery that the level of phosphorylation of position 406 (e.g., a serine residue) of human eukaryotic initiation factor 4B (eIF4B) is a reliable biomarker for maternal embryonic leucine zipper kinase (MELK) activity suitable for use in measuring MELK enzymatic activity for preclinical and clinical applications. Similarly, the present invention is based, at least in part, on the discovery that the level of phosphorylation of position 3 (e.g., a threonine residue) and/or position 10 (e.g., a serine residue) of human Histone H3 and/or position 11 (e.g., a threonine residue) is also a reliable biomarker for MELK activity suitable for use in measuring MELK, enzymatic activity or preclinical and clinical applications.

In one aspect, a method of identifying an agent which inhibits kinase oncogenic activity of human maternal embryonic leucine zipper kinase (MELK) or an ortholog thereof, comprising a) contacting a sample comprising i) human MELK or an ortholog thereof and ii) human eukaryotic initiation factor 4B (eIF4B) or an ortholog thereof, with the agent; and b) determining the ability of the agent to inhibit Ser-406 phosphorylation of human eIF4B or a corresponding phosphorylatable amino acid in the ortholog of human eIF4B, wherein decreased phosphorylation identifies an agent which inhibits kinase or oncogenic activity of human MELK or the ortholog thereof, is provided. In one embodiment, the inhibition of said Ser-406 phosphorylation of human eIF4B or a corresponding phosphorylatable amino acid in an ortholog of human eIF4B is determined by comparing the amount of Ser-406 phosphorylated human eIF4B or a corresponding phosphorylatable amino acid in the ortholog of human eIF4B, in the sample relative to a control. In another embodiment, the control is the amount of Ser-406 phosphorylated human eIF4B or a corresponding phosphorylatable amino acid in the ortholog of human eIF4B in the sample relative to said amount in the absence of the agent or at an earlier timepoint after contact of the sample with the agent. In still another embodiment, the inhibition of said Ser-406 phosphorylation of human eIF4B or a corresponding phosphorylatable amino acid in an ortholog of human eIF4B is determined by comparing the ratio of the amount of Ser-406 phosphorylated human eIF4B, or a corresponding phosphorylatable amino acid in the ortholog of human eIF4B, in the sample relative to the total amount of human eIF4B or ortholog thereof, to a control. In yet another embodiment, the control is the ratio of the amount of Ser-406 phosphorylated human eIF4B or a corresponding phosphorylatable amino acid in the ortholog of human eIF4B in the sample relative to said ratio in the absence of the agent or at an earlier timepoint after contact of the sample with the agent. In another embodiment, the method further comprises determining the amount of a protein translated from an RNA with highly structured 5'UTR, optionally wherein the protein is selected from the group consisting of cellular myelocytomatosis oncogene (c-Myc), X-linked inhibitor of apoptosis protein (XIAP), and ornithine decarboxylase (ODC1). In still another embodiment, the method further comprises a step of determining whether the agent directly binds said human eIF4B or said ortholog thereof, or said human MELK or said ortholog thereof. In yet another embodiment, the sample is selected from the group consisting of in vitro, ex vivo, and in vivo samples. In another embodiment, the sample comprises cells (e.g., cancer cells, such as a cancer selected from the group consisting of any cancer in which MELK or eIF4B is amplified or overexpressed, any cancer having an activating mutation of MELK or eIF4B, and any cancer in which MELK or eIF4B is activated by other kinases). In still another embodiment, the cells are obtained from a subject. In yet another embodiment, the sample is selected from the group consisting of tissue, whole blood, serum, plasma, buccal scrape, saliva, cerebrospinal fluid, urine, stool, and bone marrow. In another embodiment, the amount of Ser-406 phosphorylated human eIF4B or a corresponding phosphorylatable amino acid in the ortholog of human eIF4B is determined by an immunoassay using a reagent which specifically binds with Ser-406 phosphorylated human eIF4B or corresponding phosphorylated ortholog of human eIF4B (e.g., a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay). In still another embodiment, the enzyme immunoassay is a sandwich enzyme immunoassay using a capture antibody or fragment thereof which specifically binds with human eIF4B or corresponding ortholog of human eIF4B and a detection antibody or fragment thereof which specifically binds with Ser-406 phosphorylated human eIF4B or a corresponding phosphorylated ortholog of human eIF4B. In yet another embodiment, said human eIF4B or ortholog thereof, and/or said human MELK or ortholog thereof, comprises a nucleic acid sequence or amino acid sequence set forth in Table 1. In another embodiment, the agent is a small molecule, or an antibody or antigen-binding fragment thereof. In still another embodiment, the agent decreases the amount of Ser-406 phosphorylated human eIF4B or a corresponding phosphorylatable amino acid in the ortholog of human eIF4B by at least 50%.

In another aspect, a method for assessing the efficacy of an agent for inhibiting kinase activity of human MELK or an ortholog thereof in a subject, comprising a) detecting in a subject sample at a first point in time, the amount of Ser-406 phosphorylated human eIF4B or the amount of a human eIF4B ortholog phosphorylated at a corresponding amino acid of human eIF4B; b) repeating step a) during at one or more subsequent points in time after administration of the agent; and c) comparing the amount of phosphorylated human eIF4B or ortholog thereof detected in step a) with said amount detected in step b), wherein a higher amount of Ser-406 phosphorylated human eIF4B or the amount of the human eIF4B ortholog phosphorylated at a corresponding amino acid of human eIF4B in the first point in time relative to at least one subsequent point in time, indicates that the agent inhibits kinase activity of human MELK or the ortholog thereof, is provided. In one embodiment, the amount of Ser-406 phosphorylated human eIF4B or a corresponding phosphorylatable amino acid in the ortholog of human eIF4B is determined by an immunoassay using a reagent which specifically binds with Ser-406 phosphorylated human eIF4B or corresponding phosphorylated ortholog of human eIF4B (e.g., a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay). In another embodiment, the enzyme immunoassay is a sandwich enzyme immunoassay using a capture antibody or fragment thereof which specifically binds with human eIF4B or corresponding ortholog of human eIF4B and a detection antibody or fragment thereof which specifically binds with Ser-406 phosphorylated human eIF4B or a corresponding phosphorylated ortholog of human eIF4B. In still another embodiment, the sample is selected from the group consisting of ex vivo and in vivo samples. In yet another embodiment, the sample comprises cancer cells (e.g., cancer cells selected from the group consisting of any cancer in which MELK or eIF4B is amplified or overexpressed, any cancer having an activating mutation of MELK or eIF4B, and any cancer in which MELK or eIF4B is activated by other kinases). In another embodiment, the sample is selected from the group consisting of tissue, whole blood, serum, plasma, buccal scrape, saliva, cerebrospinal fluid, urine, stool, and bone marrow. In still another embodiment, the sample in step a) and/or step b) is a portion of a single sample obtained from the subject. In yet another embodiment, the sample in step a) and/or step b) is a portion of pooled samples obtained from the subject. In another embodiment, the subject has undergone treatment for cancer, has completed treatment for cancer, and/or is in remission from cancer between the first point in time and the subsequent point in time. In still another embodiment, said human eIF4B or ortholog thereof, and/or said human MELK or ortholog thereof, comprises a nucleic acid sequence or amino acid sequence set forth in Table 1. In yet another embodiment, the agent is a small molecule, or an antibody or antigen-binding fragment thereof. In another embodiment, the agent decreases the amount of Ser-406 phosphorylated human eIF4B or a corresponding phosphorylatable amino acid in the ortholog of human eIF4B by at least 50%.

In still another aspect, a method of treating a subject afflicted with cancer comprising administering to the subject an agent that inhibits Ser-406 phosphorylation of human eIF4B or a corresponding phosphorylatable amino acid in an ortholog of human eIF4B, thereby treating the subject afflicted with the cancer, is provided. In one embodiment, the agent is administered in a pharmaceutically acceptable formulation. In another embodiment, the agent is a small molecule, or an antibody or antigen-binding fragment thereof. In still another embodiment, the agent directly binds said human eIF4B or the ortholog thereof, or said human MELK or the ortholog thereof. In yet another embodiment, the cancer is selected from the group consisting of any cancer in which MELK or eIF4B is amplified or overexpressed, any cancer having an activating mutation of MELK or eIF4B, and any cancer in which MELK or eIF4B is activated by other kinases. In another embodiment, said human eIF4B or ortholog thereof, and/or said human MELK or ortholog thereof, comprises a nucleic acid sequence or amino acid sequence set forth in Table 1. In still another embodiment, the agent is a small molecule, or an antibody or antigen-binding fragment thereof. In yet another embodiment, the agent decreases the amount of Ser-406 phosphorylated human eIF4B or a corresponding phosphorylatable amino acid in the ortholog of human eIF4B by at least 50%. In another embodiment, the method further comprises administering one or more additional anti-cancer agents.

In yet another aspect, a method of determining the function or activity of human MELK or an ortholog, comprising a) detecting in a sample the amount of Ser-406 phosphorylated human eIF4B or the amount of a human eIF4B ortholog phosphorylated at a corresponding amino acid of human eIF4B; b) repeating step a) in the same sample or a test sample at one or more subsequent points in time after manipulation of the sample and/or manipulation of the same sample or test sample; and c) comparing the amount of phosphorylated human eIF4B or ortholog thereof detected in step a) with said amount detected in step b), wherein a modulated of Ser-406 phosphorylated human eIF4B or the amount of the human eIF4B ortholog phosphorylated at a corresponding amino acid of human eIF4B in the first point in time relative to at least one subsequent point in time and/or at least one subsequent manipulation of the same sample or test sample, indicates that the function or activity of human MEL or an ortholog thereof is modulated, is provided. In one embodiment, the amount of Ser-406 phosphorylated human eIF4B or a corresponding phosphorylatable amino acid in the ortholog of human eIF4B is determined by an immunoassay using a reagent which specifically binds with Ser-406 phosphorylated human eIF4B or corresponding phosphorylated ortholog of human eIF4B (e.g., a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay). In another embodiment, the enzyme immunoassay is a sandwich enzyme immunoassay using a capture antibody or fragment thereof which specifically binds with human eIF4B or corresponding ortholog of human eIF4B and a detection antibody or fragment thereof which specifically binds with Ser-406 phosphorylated human eIF4B or a corresponding phosphorylated ortholog of human eIF4B. In still another embodiment, the sample is selected from the group consisting of in vitro, ex vivo, and in vivo samples. In yet another embodiment, the sample comprises cells or the method uses a cell-based assay. In another embodiment, the cells are cancer cells selected from the group consisting of any cancer in which MELK or eIF4B is amplified or overexpressed, any cancer having an activating mutation of MELK or eIF4B, and any cancer in which MELK or eIF4B is activated by other kinases. In still another embodiment, the sample is selected from the group consisting of tissue, whole blood, serum, plasma, buccal scrape, saliva, cerebrospinal fluid, urine, stool, and bone marrow. In yet another embodiment, the same sample or test sample in step a) and/or step b) is a portion of a single sample obtained from a subject. In another embodiment, the same sample or test sample in step a) and/or step b) is a portion of pooled samples obtained from a subject. In still another embodiment, the subject has undergone treatment for cancer, has completed treatment for cancer, and/or is in remission from cancer between the first point in time and the subsequent point in time. In yet another embodiment, said human eIF4B or ortholog thereof, and/or said human MELK or ortholog thereof, comprises a nucleic acid sequence or amino acid sequence set forth in Table 1. In another embodiment, the manipulation of the sample is selected from the group consisting of contacting the sample with a test agent, contacting the sample with an upstream signal of the MELK signaling pathway, and contacting the sample with a MELK inhibitor. In still another embodiment, the test agent is a small molecule, or an antibody or antigen-binding fragment thereof. In yet another embodiment, the test agent decreases the amount of Ser-406 phosphorylated human eIF4B or a corresponding phosphorylatable amino acid in the ortholog of human eIF4B by at least 50%.

In another aspect, a method of identifying an agent which inhibits kinase or oncogenic activity of human MELK or an ortholog thereof, comprising: a) contacting a sample comprising i) human MELK or an ortholog thereof and human Histone H3 or an ortholog thereof, with the agent; and b) determining the ability of the agent to inhibit Thr-3 phosphorylation of human Histone H3 or a corresponding phosphorylatable amino acid in the ortholog of human Histone H3; and/or Ser-10 phosphorylation of human Histone H3 or a corresponding phosphorylatable amino acid in the ortholog of human Histone H3, and/or Thr-11 phosphorylation of human Histone H3 or a corresponding phosphorylatable amino acid in the ortholog of human Histone H3, wherein decreased phosphorylation identifies an agent which inhibits kinase oncogenic activity of human MELK or the ortholog thereof is provided. In one embodiment, the inhibition of said Thr-3 phosphorylation and/or Ser-10 phosphorylation and/or Thr-11 phosphorylation of human Histone H3, or a corresponding phosphorylatable amino acid in an ortholog of human Histone H3, is determined by comparing the amount of Thr-3 phosphorylated human Histone H3 and/or Ser-10 phosphorylated human Histone H3 and/or Thr-11 phosphorylated human Histone H3, or a corresponding phosphorylatable amino acid in the ortholog of human Histone H3, in the sample relative to a control. In another embodiment, the control is the amount of Thr-3 phosphorylated and/or Ser-10 phosphorylated and/or Thr-11 phosphorylated human Histone H3, or a corresponding phosphorylatable amino acid in the ortholog of human Histone H3, in the sample relative to said amount in the absence of the agent or at an earlier timepoint after contact of the sample with the agent. In still another embodiment, the inhibition of said Thr-3 phosphorylation and/or Ser-10 phosphorylation and/or Thr-11 phosphorylation of human Histone H3, or a corresponding phosphorylatable amino acid in an ortholog of human Histone H3, is determined by comparing the ratio of the amount of Thr-3 phosphorylated and/or Ser-10 phosphorylated and/or Thr-11 phosphorylated human Histone H3, or a corresponding phosphorylatable amino acid in the ortholog of human Histone H3 in the sample relative to the total amount of human Histone H3 or ortholog thereof, to a control. In yet another embodiment, the control is the ratio of the amount of Thr-3 phosphorylated and/or Ser-10 phosphorylated and/or Thr-11 phosphorylated human Histone H3, or a corresponding phosphorylatable amino acid in the ortholog of human Histone H3 in the sample relative to said ratio in the absence of the agent or at an earlier timepoint after contact of the sample with the agent. In another embodiment, the method further comprises determining the amount of a mitosis-specific protein. In still another embodiment, the method further comprises a step of determining whether the agent directly binds said human Histone H3 or said ortholog thereof, or said human MELK or said ortholog thereof. In yet another embodiment, the sample is selected from the group consisting of in vitro, ex vivo, and in vivo samples. In another embodiment, the sample comprises cells, such as cancer cells (e.g., cells from a cancer selected from the group consisting of any cancer in which MELK or Histone H3 is amplified or overexpressed, any cancer having an activating mutation of MELK or Histone H3, and any cancer in which MELK or Histone H3 is activated by other kinases). In still another embodiment, the cells are obtained from a subject. In yet another embodiment, the sample is selected from the group consisting of tissue, whole blood, serum, plasma, buccal scrape, saliva, cerebrospinal fluid, urine, stool, and bone marrow. In another embodiment, the amount of Thr-3 phosphorylated and/or Ser-10 phosphorylated and/or Thr-11 phosphorylated human Histone H3, or a corresponding phosphorylatable amino acid in the ortholog of human Histone H3, is determined by an immunoassay using a reagent which specifically binds with Thr-3 phosphorylated or Ser-10 phosphorylated or Thr-11 phosphorylated human Histone H3, or corresponding phosphorylated ortholog of human Histone H3. In still another embodiment, the immunoassay is a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay. In yet another embodiment, the enzyme immunoassay is a sandwich enzyme immunoassay using a capture antibody or fragment thereof which specifically binds with human Histone H3 or corresponding ortholog of human Histone H3 and a detection antibody or fragment thereof which specifically binds with Thr-3 phosphorylated or Ser-10 phosphorylated or Thr-11 phosphorylated human Histone H3, or a corresponding phosphorylated ortholog of human Histone H3. In another embodiment, the human Histone H3 or ortholog thereof, and/or said human MELK or ortholog thereof comprises a nucleic acid sequence or amino acid sequence set forth in Table 1. In still another embodiment, the agent is a small molecule, or an antibody or antigen-binding fragment thereof. In yet another embodiment, the agent decreases the amount of Thr-3 phosphorylated and/or Ser-10 phosphorylated and/or Thr-11 phosphorylated human Histone H3, or a corresponding phosphorylatable amino acid in the ortholog of human Histone H3, by at least 50%.

In still another aspect, a method for assessing the efficacy of an agent for inhibiting kinase activity of human MELK or an ortholog thereof in a subject, comprising: a) detecting in a subject sample at a first point in time, the amount of Thr-3 phosphorylated and/or Ser-10 phosphorylated and/or Thr-11 phosphorylated human Histone H3, or the amount of a human Histone H3 ortholog phosphorylated at a corresponding amino acid of human Histone H3; b) repeating step a) during at one or more subsequent points in time after administration of the agent; and c) comparing the amount of phosphorylated human Histone H3 or ortholog thereof detected in step a) with said amount detected in step b), wherein a higher amount of Thr-3 phosphorylated and/or Ser-10 phosphorylated and/or Thr-11 phosphorylated human Histone H3, or the amount of the human Histone H3 ortholog phosphorylated at a corresponding amino acid of human Histone H3, in the first point in time relative to at least one subsequent point in time, indicates that the agent inhibits kinase activity of human MELK or the ortholog thereof is provided. In one embodiment, the amount of Thr-3 phosphorylated and/or Ser-10 phosphorylated and/or Thr-11 phosphorylated human Histone H3, or a corresponding phosphorylatable amino acid in the ortholog of human Histone H3, is determined by an immunoassay using a reagent which specifically binds with Thr-3 phosphorylated human Histone H3 or Ser-10 phosphorylated human Histone H3 or Thr-11 phosphorylated human Histone H3, or corresponding phosphorylated ortholog of human Histone H3. In another embodiment, the immunoassay is a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay. In still another embodiment, the enzyme immunoassay is a sandwich enzyme immunoassay using a capture antibody or fragment thereof which specifically binds with human Histone H3 or corresponding ortholog of human Histone H3 and a detection antibody or fragment thereof which specifically binds with Thr-3 phosphorylated Ser-10 phosphorylated or Thr-11 phosphorylated human Histone H3, or a corresponding phosphorylated ortholog of human Histone H3. In yet another embodiment, the sample is selected from the group consisting of ex vivo and in vivo samples. In another embodiment, the sample comprises cancer cells (e.g., cancer cells selected from the group consisting of any cancer in which MELK or Histone H3 is amplified or overexpressed, any cancer having an activating mutation of MELK or Histone H3, and any cancer in which MELK or Histone H3 is activated by other kinases). In still another embodiment, the sample is selected from the group consisting of tissue, whole blood, serum, plasma, buccal scrape, saliva, cerebrospinal fluid, urine, stool, and bone marrow. In yet another embodiment, the sample in step a) and/or step b) is a portion of a single sample obtained from the subject. In another embodiment, the sample in step a) and/or step b) is a portion of pooled samples obtained from the subject. In still another embodiment, the subject has undergone treatment for cancer, has completed treatment for cancer, and/or is in remission from cancer between the first point in time and the subsequent point in time. In yet another embodiment, the human Histone H3 or ortholog thereof, and/or said human MELK or ortholog thereof, comprises a nucleic acid sequence or amino acid sequence set forth in Table 1. In another embodiment, the agent is a small molecule, or an antibody or antigen-binding fragment thereof. In still another embodiment, the agent decreases the amount of Thr-3 phosphorylated and/or Ser-10 phosphorylated and/or Thr-11 phosphorylated human Histone H3, or a corresponding phosphorylatable amino acid in the ortholog of human Histone H3, by at least 50%.

In yet another aspect, a method of treating a subject afflicted with cancer comprising administering to the subject an agent that inhibits Thr-3 phosphorylation and/or Ser-10 phosphorylation and/or Thr-11 phosphorylation of human Histone H3, or a corresponding phosphorylatable amino acid in an ortholog of human Histone H3, thereby treating the subject afflicted with the cancer is provided. In one embodiment, the agent is administered in a pharmaceutically acceptable formulation. In another embodiment, the agent is a small molecule, or an antibody or antigen-binding fragment thereof. In still another embodiment, the agent directly binds said human Histone H3 or the ortholog thereof, or said human MELK or the ortholog thereof. In yet another embodiment, the cancer is selected from the group consisting of any cancer in which MELK or Histone H3 is amplified or overexpressed, any cancer having an activating mutation of MELK or Histone H3, and any cancer in which MELK or Histone H3 is activated by other kinases. In another embodiment, the human Histone H3 or ortholog thereof, and/or said human MELK or ortholog thereof, comprises a nucleic acid sequence or amino acid sequence set forth in Table 1. In still another embodiment, the agent is a small molecule, or an antibody or antigen-binding fragment thereof. In yet another embodiment, the agent decreases the amount of Thr-3 phosphorylated and/or Ser-10 phosphorylated and/or Thr-11 phosphorylated human Histone H3, or a corresponding phosphorylatable amino acid in the ortholog of human Histone H3, by at least 50%. In another embodiment, the method further comprises administering one or more additional anti-cancer agents.

In another aspect, a method of determining the function or activity of human MELK or an ortholog, comprising: a) detecting in a sample the amount of Thr-3 phosphorylated and/or Ser-10 phosphorylated and/or Thr-11 phosphorylated human histone H3 or the amount of a human Histone H3 ortholog phosphorylated at a corresponding amino acid of human Histone H3; b) repeating step a) in the same sample or a test sample at one or more subsequent points in time after manipulation of the sample and/or manipulation of the same sample or test sample; and c) comparing the amount of phosphorylated human Histone H3 or ortholog thereof detected in step a) with said amount detected in step b), wherein a modulated amount of Thr-3 phosphorylated and/or Ser-10 phosphorylated and/or Thr-11 phosphorylated human Histone H3, or the amount of the human Histone H3 ortholog phosphorylated at a corresponding amino acid of human Histone H3, in the first point in time relative to at least one subsequent point in time and/or at least one subsequent manipulation of the same sample or test sample, indicates that the function or activity of human MELK or an ortholog thereof is modulated is provided. In one embodiment, the amount of Thr-3 phosphorylated and/or Ser-10 phosphorylated and/or Thr-11 phosphorylated human Histone H3, or a corresponding phosphorylatable amino acid in the ortholog of human Histone H3, is determined by an immunoassay using a reagent which specifically binds with Thr-3 phosphorylated Ser-10 phosphorylated or Thr-11 phosphorylated human Histone H3, or corresponding phosphorylated ortholog of human Histone H3. In another embodiment, the immunoassay is a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay. In still another embodiment, the enzyme immunoassay is a sandwich enzyme immunoassay using a capture antibody or fragment thereof which specifically binds with human Histone H3 or corresponding ortholog of human Histone H3 and a detection antibody or fragment thereof which specifically binds with Thr-3 phosphorylated or Ser-10 phosphorylated or Thr-11 phosphorylated human Histone H3, or a corresponding phosphorylated ortholog of human Histone H3. In yet another embodiment, the sample is selected from the group consisting of in vitro, ex vivo, and in vivo samples. In another embodiment, the sample comprises cells or the method uses a cell-based assay. In still another embodiment, the cells are cancer cells selected from the group consisting of any cancer in which MELK or Histone H3 is amplified or overexpressed, any cancer having activating mutation of MELK or Histone H3, and any cancer in which MELK or Histone H3 is activated by other kinases. In yet another embodiment, the sample is selected from the group consisting of tissue, whole blood, serum, plasma, buccal scrape, saliva, cerebrospinal fluid, urine, stool, and bone marrow. In another embodiment, the same sample or test sample in step a) and/or step b) is a portion of a single sample obtained from a subject. In still another embodiment, the same sample or test sample in step a) and/or step b) is a portion of pooled samples obtained from a subject. In yet another embodiment, the subject has undergone treatment for cancer, has completed treatment for cancer, and/or is in remission from cancer between the first point in time and the subsequent point in time. In another embodiment, the human Histone H3 or ortholog thereof, and/or said human MELK or ortholog thereof, comprises a nucleic acid sequence or amino acid sequence set forth in Table 1. In still another embodiment, the manipulation of the sample is selected from the group consisting of contacting the sample with a test agent, contacting the sample with an upstream signal of the MELK signaling pathway, and contacting the sample with a MELK inhibitor. In yet another embodiment, the test agent is a small molecule, or an antibody or antigen-binding fragment thereof. In another embodiment, the test agent decreases the amount of Thr-3 phosphorylated and/or Ser-10 phosphorylated and/or Thr-11 phosphorylated human Histone H3, or a corresponding phosphorylatable amino acid in the ortholog of human Histone H3, by at least 50%.

It will also be understood that certain embodiments of the present invention can be used with more than one method described herein, according to knowledge available to the skilled artisan.

Figure 11:
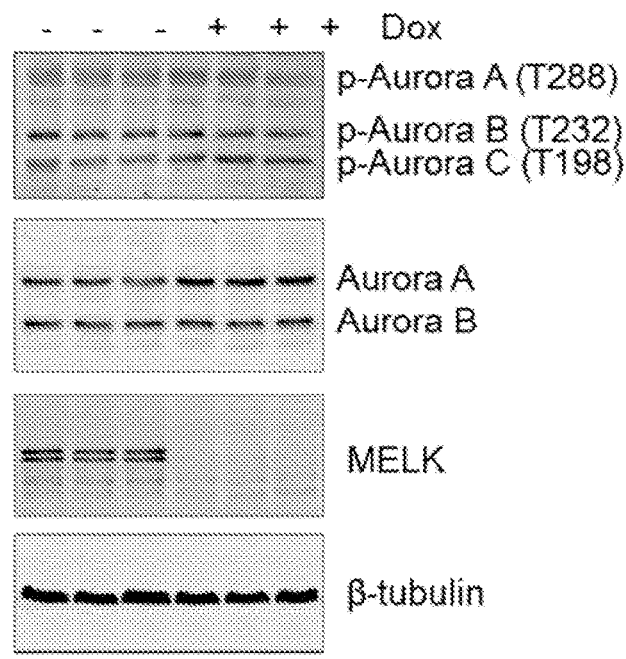

FIG. 11 shows that knocking down MELK does not affect the phosphorylation of Aurora kinases, which are known kinases for Histone H3 at Ser 10. MDA-MB-468 cells stably transduced with tet-on shMELK were untreated or treated with doxycycline (200 ng/ml) to induce gene silencing. Cells were treated with nocodazole (200 ng/ml) for 20 hours. Mitotic cells were harvested by shake-off and cell lysates were subjected to immunoblotting using the indicated antibodies.

Figure 12:
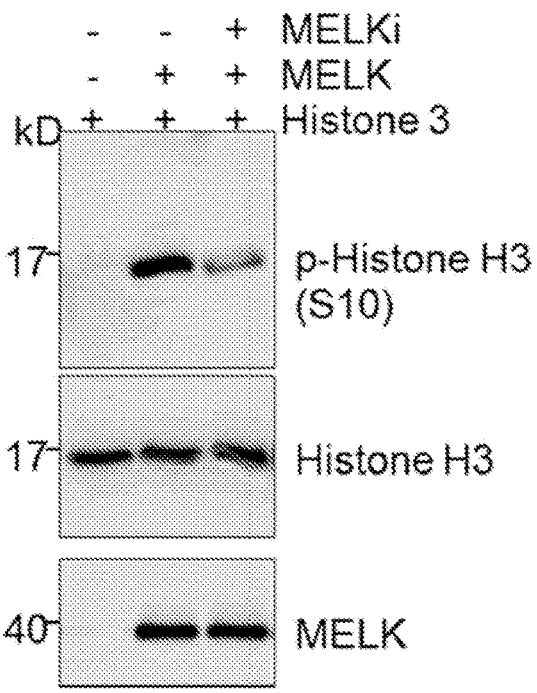

FIG. 12 shows that a MELK inhibitor suppresses MELK-induced phosphorylation of Histone H3 at Ser 10 in vitro. Recombinant Histone H3 was incubated without or with recombinant MELK (kinase domain) for 30 min. at 30° C. in the absence or presence of OTSSP167 (200 ng/ml final). Reactions were terminated by adding SDS sample buffer. Samples were subjected to immunoblotting using the indicated antibodies.

Figure 13:
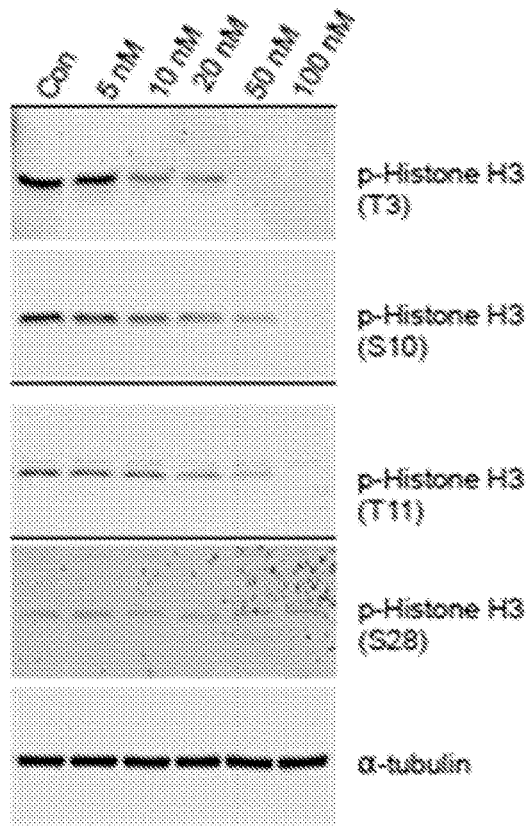

FIG. 13 shows that a MELK inhibition suppresses the mitotic phosphorylation of Histone H3 at Thr-3, Ser-10 and Thr-11, but not Ser-28, in a concentration-dependent manner. Mitotic cells were harvested through nocodazole-induced cell cycle arrest at prometaphase (200 ng/ml nocodazole, 20 hours). Cells were treated with the small chemical inhibitor of MELK, OTSSP167, for 30 min, at the indicated concentrations. Cell lysates were then prepared for immunoblotting.

DETAILED DESCRIPTION OF THE INVENTION

The methods of the present invention relate to the surprising determination that the level of phosphorylation of position 406 (e.g., a serine residue) of human eukaryotic initiation factor 4B (eIF4B), or a corresponding phosphorylatable amino acid of an ortholog thereof, serves as a biomarker for MELK enzymatic (e.g., kinase) and/or oncogenic activity. Specifically, decreased phosphorylation of, for example, Ser-406 of human eIF4B (e.g., by directly or indirectly inhibiting MELK-mediated phosphorylation of Ser-406) corresponds with a reduction in MELK enzymatic activity (e.g., kinase activity) and MELK-mediated oncogenic effects. Such a biomarker is particularly advantageous for preclinical and clinical applications because the phosphorylation state of eIF4B is directly associated with the MELK oncogene itself. Similarly, the methods of the present invention also relate to the surprising determination that the level of phosphorylation of position 10 (e.g., a serine residue) of human Histone H3, or a corresponding phosphorylatable amino acid of an ortholog thereof, and/or the level of phosphorylation of position 11 (e.g., a threonine residue) of human Histone H3, or a corresponding phosphorylatable amino acid of an ortholog thereof, serves as a biomarker for MELK enzymatic (e.g., kinase) and/or oncogenic activity. Specifically, decreased phosphorylation of, for example, Thr-3 of human Histone H3 (e.g., by directly or indirectly inhibiting MELK-mediated phosphorylation of Thr-3) and/or Ser-10 of human Histone H3 (e.g., by directly or indirectly inhibiting MELK-mediated phosphorylation of Ser-10) and/or Thr-11 of human Histone H3 (e.g., by directly or indirectly inhibiting MELK-mediated phosphorylation of Thr-11) corresponds with a reduction in MELK enzymatic activity (e.g., kinase activity) and MELK-mediated oncogenic effects. Such a biomarker is particularly advantageous for preclinical and clinical applications because the phosphorylation state of Histone H3 is directly associated with the MELK oncogene itself. In some embodiments, Ser-406 of human eIF4B, Thr-3 of human Histone H3, Ser-10 of human Histone H3, and/or Thr-11 of human Histone H3, as well as any corresponding phosphorylatable amino acid of an ortholog thereof, including in any combination thereof, are contemplated for use according to the present invention. In other embodiments, Ser-28 of human eIF4B or a corresponding phosphorylatable amino acid of an ortholog thereof is not regulated MELK and is not used according to the present invention.

A. MELK, eIF4B, and Histone H3 Molecules

As used herein, "MELK" refers to the MELK member of the protein kinase superfamily and is alternatively known as "pEG3 kinase," "protein kinase Eg3," "protein kinase," and "serine/threonine-protein kinase MELK." At least nine splice variants encoding nine distinct human MELK isoforms exist. Human MELK transcript variant 1 (NM_014791.3) encodes the long human MELK isoform 1 (NP_55606.1). Human MELK transcript variant 2 (NM_01256685.1) lacks an exon in the 3' coding region compared to transcript variant 1, but maintains the reading frame and results in an isoform (NP_001243614.1) that is shorter than isoform 1. Human MELK transcript variant 3 (NM_001256687.1) lacks an exon in the 5' coding region compared to transcript variant 1, but maintains the reading frame and results in an isoform (NP_001243616.1) that is shorter than isoform 1. Human MELK transcript variant 4 (NM_001256688.1) lacks two consecutive exons in the 5' coding region compared to transcript variant 1, but maintains the reading frame and results in an isoform (NP_001243617.1) that is shorter than isoform 1. Human MELK transcript variant 5 (NM_001256689.1) initiates translation at an alternate start codon and lacks an exon in the 5' coding region compared to transcript variant 1 and thus results in an isoform (NP_001243618.1) that is shorter than and has a distinct N-terminus from isoform 1. Human MELK transcript variant 6 (NM_001256690.1) initiates translation at an alternate start codon and lacks two consecutive exons in the 5' coding region compared to transcript variant 1, but maintains the reading frame and results in an isoform (NP_001243619.1) that is shorter than and has a distinct N-terminus from isoform 1. Human MELK transcript variant 7 (NM_001256691.1) initiates translation at an alternate start codon and lacks two exons in the 5' coding region compared to transcript variant 1, but maintains the reading frame and results in an isoform (NP_001243620.1) that is shorter than and has a distinct N-terminus from isoform 1. Human MELK transcript variant 8 (NM_001256692.1) lacks three exons in the 5' coding region and initiates translation at a downstream, in-frame start codon compared to transcript variant 1 and results in an isoform (NP_001243621.1) that has a shorter N-terminus than isoform 1. Finally, human MELK transcript variant 9 (NM_001256693.1) lacks two consecutive exons the 5' coding region and initiates translation at a downstream, in-frame start codon compared to transcript variant 1 and results in an isoform (NP_001243622.1) that has a shorter N-terminus than isoform 1. The protein domains and structural basis for the regulation of MELK autophosphorylation and activation of kinase activities on target proteins is known (see, at least Cao et al. (2013) *PLoS One* 8:e70031 and Canevari et al. (2013) *Biochemistry* 52:6380-6387).

Mouse MELK nucleic acid (NM_010790.2) and amino acid (NP_034920.2) sequences are publicly available on the GenBank database maintained by the U.S. National Center for Biotechnology Information. Nucleic acid and polypeptide sequences of MELK orthologs in species other than mice and humans are also well known and include, for example, chimpanzee MELK (XM_001169038.3, XP_001169038.1, XM_001168991.3, XP_001168991.1, XM_001168745.3, XP_001168745.1, XM_001168775.3, XP_001168775.1, XM_003951427.1, XP_003951476.1, XM_520578.4, XP_520578.3, XM_801168022.3, XP_001168822.2, XM_003312085.2, XP_003312133.1, XM_003951428.1, XP_003951477.1, XM_003312086.2, and XP_003312134.1), monkey MELK (XM_001115076.2 and XP_001115076.2), dog MELK (XM_003431578.1, XP_003431626.1, XM_538730.3, XP_538730.2, XM_003431579.1, and XP_003431627.1), cow MELK (NM_001111260.1 and NP_001104730.1), rat MELK (NM_001108662.1 and NP_001102132.1), chicken MELK (NM_001031509.1 and NP_001026680.1), and zebrafish MELK (NM_206888.2 and NP_996771.2).

As used herein, "eIF4B" refers to the eukaryotic translation initiation factor 4B member of the eukaryotic translation initiation factor family and is alternatively known as "EIF-4B" and "PRO1843." Human eIF4B nucleic acid (NM_001417.4) and amino acid (NP_001408.2) sequences are publicly available on the GenBank database maintained by the U.S. National Center for Biotechnology Information. Nucleic acid and polypeptide sequences of eIF4B orthologs in species other than humans are also well known and include, for example, mouse eIF4B (NM_145625.3 and NP_663600.2), chimpanzee eIF4B (XM_003313676.1, XP_003313724.1, XM_001142097.3, and XP_001142097.3), monkey eIF4B (NM_001195808.1 and NP_001182737.1), dog eIF4B (XM_853888.2, XP_858981.2, XM_853812.2, and XP_858905.2), cow eIF4B (NM_001035028.2 and NP_001030200.1), rat eIF4B (NM_001008324.1 and NP_001008325.1), and chicken eIF4B (XM_003643408.2 and XP_003643456.2). In addition, "Ser-406" of eIF4B refers to the amino acid numbering of the human eIF4B. Accordingly, a skilled artisan will readily understand that Ser-406 of the human eIF4B polypeptide is conserved across numerous species and that although those specific residues may be referenced herein, the methods of the present invention apply equally well to the corresponding residues (e.g., phosphorylatable amino acids) of isoforms, homologs, and orthologs in other species corresponding to said Ser-406 of human eIF4B.

As used herein, the term "Histone H3" refers to the H3 member of the Histone family, which comprises proteins used to form the structure of nucleosomes in eukaryotic cells. Eukaryotes have chromatin arranged around proteins in the form of nucleosomes, which are the smallest subunits of chromatin and include approximately 146-147 base pairs of DNA wrapped around an octamer of core histone proteins (two each of H2A, H2B, H3, and H4). Mammalian cells have three known sequence variants of Histone H3 proteins, denoted H3.1, H3.2 and H3.3, that are highly conserved differing in sequence by only a few amino acids. Post-translational modification of Histone H3 residues are important in many cellular processes and phosphorylation of serine 10 and/or serine 28 are important for cell division and proliferation regulation. Phosphorylated Histone H3 at serine 10 is a specific biomarker for mitotic cells, similar to other well-known mitosis-specific markers, such as phosphorylated MPM-2, phosphorylated retinoblastoma protein 1 (Rb), phosphorylated cdc2, BubR1, cyclin B1, cdc25c, cdk1, cdc27, and the like. Any serine, threonine, or tyrosine residue can be phosphorylated. In some embodiments, other possible phosphorylation sites include threonine 3, threonine 6, threonine 11, serine 31, tyrosine 41, serine 57, threonine 80, and threonine 107.

As used herein, the term "Histone H3" can refer to H3.1, H3.2, or H3.3 individually or collectively. These amino acid sequences include a methionine as residue number 1 that is cleaved off when the protein is processed. Thus, for example, serine 11 in the Histone H3 amino acid sequences shown in Table 1 below corresponds to serine (Ser) 10 of the present invention. These three protein variants are encoded by at least fifteen different genes/transcripts. Sequences encoding the Histone H3.1 variant are publicly available as HIST1H3A (NM_003529.2; NP_003520.1), HIST1H3B (NM_003537.3; NP_003528.1), HIST1H3C (NM_003531.2; NP_003522.1), HIST1H3D (NM_003530.3; NP_003521.2), HIST1H3E (NM_003532.2; NP_003523.1), HIST1H3F (NM_021018.2; NP_066298.1), HIST1H3G (NM_003534.2; NP_003525.1), HIST1H3H (NM_003536.2; NP_003527.1), HIST1H3I (NM_003533.2; NP_003524.1), and HIST1H3J (NM_003535.2; NP_003526.1). Sequences encoding the Histone H3.2 variant are publicly available as HIST2H3A (NM_001005464.2; NP_001005464.1), HIST2H3C (NM_021059.2; NP_066403.2), and HIST2H3D (NM_001123375.1; NP_001116847.1). Sequences encoding the Histone H3.3 variant are publicly available as H3F3A (NM_002107.3; NP_002098.1) and H3F3B (NM_005324.3; NP_005315.1). See U.S. Pat. Publ. 2012/0202843 for additional details. Moreover, polypeptide sequences for Histone H3 orthologs, as well as nucleic acid sequences that encode such polypeptides, are well-known in many species, and include, for example, Histone H3.1 orthologs in mice (NM_013550.4; NP_038578.2), chimpanzee (XM_527253.4; XP_527253.2), monkey (XM_001088298.2; XP_001088298.1), dog (XM_003434195.1; XP_003434243.1), cow (XM_002697460.1; XP_002697506.1), rat (XM_001055231.2; XP_001055231.1), and zebrafish (NM_001100173.1; NP_001093643.1). Histone H3.2 orthologs in mice (NM_178215.1; NP_835587.1), chimpanzee (XM_524859.4; XP_524859.2), monkey (XM_001084245.2; XP_001084245.1), dog (XM_003640147.1; XP_003640195.1), cow (XM_002685500.1; XP_002685546.1), rat (NM_001107698.1; NP_001101168.1), chicken (XM_001233027.2; XP_001233028.1), and zebrafish (XM_002662732.1; XP_002662778.1). Similarly, Histone H3.3 orthologs in mice (XM_892026.4; XP_897119.3), monkey (XM_001085836.2; XP_001085836.1), cow (NM_001099370.1; NP_001092840.1), rat (NM_053985.2; NP_446437.1), chicken (NM_205296.1; NP_990627.1), and zebrafish (NM_200003.1; NP_956297.1), are well-known. Antibodies for the detection of phosphorylated H3 histone, such as phosphorylated Histone H3 at Thr-3, Ser-10, Thr-11, and other phosphorylatable residues of Histone H3, as well as methods for making such antibodies are known in the art. In addition, for example, "Ser-10" of Histone H3 refers to the amino acid numbering of the human Histone H3. Accordingly, a skilled artisan will readily understand that Ser-10 of the human Histone H3 polypeptide is conserved across numerous species and that although those specific residues may be referenced herein, the methods of the present invention apply equally well to the corresponding residues (e.g., phosphorylatable amino acids)

of isoforms, homologs, and orthologs in other species corresponding to said Ser-10 of human Histone H3. The same applies to Thr-3 and Thr-11.

Representative MELK, eIF4B, and Histone H3 orthologs are provided herein (e.g., at least at Table 1 and the Examples) as follows:

TABLE 1

Human MELK (isoform 1) cDNA Sequence (NM_014791.3)
```
   1 atgaaagatt atgatgaact tctcaaatat tatgaattac atgaaactat tgggacaggt
  61 ggctttgcaa aggtcaaact tgcctgccat atccttactg gagagatggt agctataaaa
 121 atcatggata aaaacacact agggagtgat ttgccccgga tcaaaacgga gattgaggcc
 181 ttgaagaacc tgagacatca gcatatatgt caactctacc atgtgctaga gacagccaac
 241 aaaatattca tggttcttga gtactgccct ggaggagagc tgtttgacta tataatttcc
 301 caggatcgcc tgtcagaaga ggagacccgg gttgtcttcc gtcagatagt atctgctgtt
 361 gcttatgtgc acagccaggg ctatgctcac agggacctca agccagaaaa tttgctgttt
 421 gatgaatatc ataaattaaa gctgattgac tttggtctct gtgcaaaacc caagggtaac
 481 aaggattacc atctacagac atgctgtggg agtctggctt atgcagcacc tgagttaata
 541 caaggcaaat catatcttgg atcagaggca gatgtttgga gcatgggcat actgttatat
 601 gttcttatgt gtggatttct accatttgat gatgataatg taatggcttt atacaagaag
 661 attatgagag gaaaatatga tgttcccaag tggctctctc ccagtagcat tctgcttctt
 721 caacaaatgc tgcaggtgga cccaaagaaa cggatttcta tgaaaaatct attgaaccat
 781 ccctggatca tgcaagatta caactatcct gttgagtggc aaagcaagaa tccttttatt
 841 cacctcgatg atgattgcgt aacagaactt tctgtacatc acagaaacaa caggcaaaca
 901 atggaggatt taatttcact gtggcagtat gatcacctca cggctaccta tcttctgctt
 961 ctagccaaga aggctcgggg aaaaccagtt cgtttaaggc tttcttcttt ctcctgtgga
1021 caagccagtg ctacccccatt cacagacatc aagtcaaata attggagtct ggaagatgtg
1081 accgcaagtg ataaaaatta tgtggcggga taatagact atgattggtg tgaagatgat
1141 ttatcaacag gtgctgctac tccccgaaca tcacagttta ccaagtactg gacagaatca
1201 aatgggtgg aatctaaatc attaactcca gccttatgca gaacacctgc aaataaatta
1261 aagaacaaag aaaatgtata tactcctaag tctgctgtaa agaatgaaga gtactttatg
1321 tttcctgagc caaagactcc agttaataag aaccagcata agagagaaat actcactacg
1381 ccaaatcgtt acactacacc ctcaaaagct agaaaccagt gcctgaaaga aactccaatt
1441 aaaataccag taaattcaac aggaacagac aagttaatga caggtgtcat tagccctgag
1501 aggccggtgcc gctcagtgga attggatctc aaccaagcac atatggagga gactccaaaa
1561 agaaagggag ccaaagtgtt tgggagcctt gaaaggggt tggataaggt tatcactgtg
1621 ctcaccagga gcaaaaggaa gggttctgcc agagacgggc ccagaagact aaagcttcac
1681 tataacgtga ctacaactag attagtgaat ccagatcaac tgttaatgaa aataatgtct
1741 attcttccaa agaagcatgt tgactttgta caaagggtt atacactgaa gtgtcaaaca
1801 cagtcagatt ttgggaaagt gacaatgcaa tttgaattag aagtgtgcca gcttcaaaaa
1861 cccgatgtgg tgggtatcag gaggcagcgg cttaagggcg atgcctgggt ttacaaaaga
1921 ttagtggaag acatcctatc tagctgcaag gtataa (SEQ ID NO:1)
```

Human MELK (isoform 1) Amino Acid Sequence (NP_55606.1)
```
   1 mkdydellky yelbetlgtg gfakcklach iltgemvaik imdkntlgsd lprikteiea
  61 lknlrhqhic qlyhvletan kifmvleycp ggwlfdyils qdrlseeetr vvfrqivsav
 121 ayvhsqgyah rdlkpenllf deyhklklid fglcakpkgn kdyhlqtccg slayaapeli
 181 qgksylgsea dvwsmgilly vlmcgflpfd ddnvmalykk imrgkydvpk wlspssilll
 241 qqmlqvdpkk rismknllnh pwimqdynyp vewqsknpfi hlddcvtel svhhrnnrqt
 301 medlislwqy dhltatylll lakkargkpv rlrlssfscg qasatpftdi ksnnwsledv
 361 tasdknyvag lidydwcedd lstgaatprt sqftkywtes ngvesksltp alcrtpankl
 421 knkenvytpk savkneeyfm fpepktpvnk nqhkreiltt pnryttpska raqclkketpi
 481 kipvnstgtd klmtgvispe rrcrsveldl nqahmeetpk rkgakvfgsl ergldkvitv
 541 ltrskrkgsa rdgprrlklh ynvtttrlvn pdqllneims ilpkkhvdfv qkgytkcqt
 601 qsdfgkvtmq felevcqlqk pdvvgirrqr lkgdawvykr lvedilssck v (SEQ ID NO:2)
```

Human MELK (isoform 2) cDNA Sequence (NM_001256685.1)
```
   1 atgaaagatt atgatgaact tctcaaatat tatgaattac atgaaactat tgggacaggt
  61 ggctttgcaa aggtcaaact tgcctgccat atccttactg gagagatggt agctataaaa
 121 atcatggata aaaacacact agggagtgat ttgccccgga tcaaaacgga gattgaggcc
 181 ttgaagaacc tgagacatca gcatatatgt caactctacc atgtgctaga gacagccaac
 241 aaaatattca tggttcttga gtactgccct ggaggagagc tgtttgacta tataatttcc
 301 caggatcgcc tgtcagaaga ggagacccgg gttgtcttcc gtcagatagt atctgctgtt
 361 gcttatgtgc acagccaggg ctatgctcac agggacctca agccagaaaa tttgctgttt
 421 gatgaatatc ataaattaaa gctgattgac tttggtctct gtgcaaaacc caagggtaac
 481 aaggattacc atctacagac atgctgtggg agtctggctt atgcagcacc tgagttaata
 541 caaggcaaat catatcttgg atcagaggca gatgtttgga gcatgggcat actgttatat
 601 gttcttatgt gtggatttct accatttgat gatgataatg taatggcttt atacaagaag
 661 attatgagag gaaaatatga tgttcccaag tggctctctc ccagtagcat tctgcttctt
 721 caacaaatgc tgcaggtgga cccaaagaaa cggatttcta tgaaaaatct attgaaccat
 781 ccctggatca tgcaagatta caactatcct gttgagtggc aaagcaagaa tccttttatt
 841 cacctcgatg atgattgcgt aacagaactt tctgtacatc acagaaacaa caggcaaaca
 901 atggaggatt taatttcact gtggcagtat gatcacctca cggctaccta tcttctgctt
 961 ctagccaaga aggctcgggg aaaaccagtt cgtttaaggc tttcttcttt ctcctgtgga
1021 caagccagtg ctacccccatt cacagacatc aagttacca agtactggac agaatcaaat
1081 ggggtggaat ctaaatcatt aactccagcc ttatgcagaa cacctgcaaa taaattaaag
1141 aacaagaaa atgtatatac tcctaagtct gctgtaaaga tgaagagta ctttatgttt
1201 cctgagccaa agactccagt taataagaac cagcataaga gagaaatact cactacgcca
1261 aatcgttaca ctacaccctc aaaagctaga aaccagtgcc tgaaagaaac tccaattaaa
1321 ataccagtaa attcaacagg aacagacaag ttaatgacag gtgtcattag ccctgagagg
1381 cggtgccgct cagtggaatt ggatctcaac caagcacata tggaggagac tccaaaaga
1441 aagggagcca agtgtttgg gagccttgaa aggggttgg ataaggttat cactgtgctc
1501 accaggagca aaaggaaggg ttctgccaga gacggggccca gaagactaaa gcttcactat
```

TABLE 1-continued

```
1561 aacgtgacta caactagatt agtgaatcca gatcaactgt tgaatgaaat aatgtctatt
1621 cttccaaaga agcatgttga ctttgtacaa aaggggttata cactgaagtg tcaaacacag
1681 tcagattttg ggaaagtgac aatgcaattt gaattagaag tgtgccagct tcaaaaccc
1741 gatgtggtgg gtatcaggag gcagcggctt aagggcgatg cctgggttta caaaagatta
1801 gtggaagaca tcctatctag ctgcaaggta taa (SEQ ID NO:3)
```

Human MELK (isoform 2) Amino Acid Sequence (NP_001243614.1)
```
  1 mkdydellky yelbetlgtg gfakcklach iltgemvaik imdkntlgsd lprikteiea
 61 lknlrhqhic qlyhvletan kifmvleycp ggwlfdyils qdrlseeetr vvfrqivsav
121 ayvhsqgyah rdlkpenllf deyhklklid fglcakpkgn kdyhlqtccg slayaapeli
181 qgksylgsea dvwsmgilly vlmcgflpfd ddnvmalykk imrgkydvpk wlspssilll
241 qqmlqvdpkk rismknllnh pwimqdynyp vewqsknpfi hldddcvtel svhhrnnrqt
301 medlislwqy dhltatylll lakkargkpv rlrlssfscg qasatpftdi kftkywtesn
361 gveskslttpa lcrtpanklk nkenvytpks avkneeyfmf pepktpvnkn qhkreilttp
421 nryttpskar nqclketpik ipvnstgtdk lmtgvisper rcrsveldln qahmeetpkr
481 kgakvfgsle rgldkvitvl trskrkgsar dgprrlklhy nvtttrlvnp dqllneimsi
541 lpkkhvdfvq kgytlkcqtq sdfgkvtmqf elevcqlqkp dvvgirrqrl kgdawvykrl
601 vedllssckv (SEQ ID NO:4)
```

Human MELK (isoform 3) cDNA Sequence (NM_001256687.1)
```
  1 atgaaagatt atgatgaact tctcaaatat tatgaattac atgaaactat tgggacaggt
 61 ggctttgcaa aggtcaaact tgcctgccat atccttactg gagagatggt agctataaaa
121 atcatggata aaacacact agggagtgat ttgccccgga tcaaaacgga gattgaggcc
181 ttgaagaacc tgagacatca gcatatatgt caactctacc atgtgctaga gacagccaac
241 aaaatattca tggttcttga ggaaaatttg ctgtttgatg aatatcataa attaaagctg
301 attgactttg gtctctgtgc aaaacccaag ggtaacaagg attaccatct acagacatgc
361 tgtgggagtc tggcttatgc agcacctgag ttaataaag gcaaatcata tcttggatca
421 gaggcagatg tttggagcat gggcatactg ttatatgttc ttatgtgtgg atttctacca
481 tttgatgatg ataatgtaat ggctttatac aagaagatta tgagaggaaa atatgatgtt
541 cccaagtggc tctctcccag tagcattctg cttcttcaac aaatgctgca ggtggaccca
601 aagaaacgga tttctatgaa aaatctattg aaccatccct ggatcatgca agattacaac
661 tatcctgttg agtggcaaag caagaatcct tttattcacc tcgatgatga ttgcgtaaca
721 gaactttctg tacatcacag aaacaacagg caaacaatgg aggatttaat ttcactgtgg
781 cagtatgatc acctcacggc tacctatctt ctgcttctag ccaagaaggc tcggggaaaa
841 ccagttcgtt taaggctttc ttctttctcc tgtggacaag ccagtgctac cccattcaca
901 gacatcaagt caaataattg gagtccggaa gatgtgaccg caagtgataa aaattatgtg
961 gcgggattaa tagactatga ttggtgtgaa gatgatttat caacaggtgc tgctactccc
1021 cgaacatcac agtttaccaa gtactggaca gaatcaaatg gggtgaatc taaatcatta
1081 actccagcct tatgcagaac acctgcaaat aaattaaaga acaaagaaaa tgtatatact
1141 cctaagtctg ctgtaaagaa tgaagagtac tttatgtttc ctgagccaaa gactccagtt
1201 aataagaacc agcataagg agaaatactc actacgccaa atcgttacac tacaccctca
1261 aaagctagaa accagtgcct gaaagaaact ccaattaaaa taccagtaaa ttcaacagga
1321 acagacaagt taatgacagg tgtcattagc cctgagaggc ggtgccgctc agtggaattg
1381 gatctcaacc aagcacatat ggaggagact ccaaaaagaa agggagccaa agtgtttggg
1441 agccttgaaa gggggttgga taaggttatc actgtgctca ccaggagcaa aaggaagggt
1501 tctgccagag acgggcccag aagactaaag cttcactata acgtgactac aactagatta
1561 gtgaatccag atcaactgtt gaatgaaata atgtctattc ttccaaagaa gcatgttgac
1621 tttgtacaaa agggttatac actgaagtgt caaacacagt cagattttgg gaaagtgaca
1681 atgcaatttg aattagaagt gtgccagctt caaaaacccg atgtggtggg tatcaggagg
1741 cagcggctta agggcgatgc ctgggttac aaaagattag tggaagacat cctatctagc
1801 tgcaaggtat aa (SEQ ID NO:5)
```

Human MELK (isoform 3) Amino Acid Sequence (NP_001243616.1)
```
  1 mkdydellky yelhetlgtg gfakvklach iltgemvaik imdkntlgsd lprikteiea
 61 lknlrhqhic qlyhvletan kifmvleenl lfdeyhklkl idfglcakpk gnkdyhlqtc
121 cgslayaape liqgksylgs eadvwsmgil lyvlmcgflp fdddnvmaly kkimrgkydv
181 pkwlspssil liqqmlqvdp kkrismknll nhpwimqdyn ypvewqsknp fihldddcvt
241 elsvhhrnnr qtmedlislw qydhltatyl lllakkargk pvrlrlssfs cgqasatpft
301 diksnnwsle dvtasdknyv aglidydwce ddlstgaatp rtsqftkywt esngveskss l
361 tpalcrtpan klknkenvyt pksavkneey fmfpepktpv nknqhkreil ttpnryttps
421 karnqclket pikipvnstg tdklmtgvis perrcrsvel dlnqahmeet pkrkgakvfg
481 slergldkvi tvltrskrkg sardgprrlk lhynvtttrl vnpdqllnei msilpkkhvd
541 fvqkgytlkc qtqsdfgkvt mqfelevcql qkpdvvgirr qrlkgdawvy krlvedilss
601 ckv (SEQ ID NO:6)
```

Human MELK (isoform 4) cDNA Sequence (NM_001256688.1)
```
  1 atgaaagatt atgatgaact tctcaaatat tatgaattac atgaaactat tgggacaggt
 61 ggctttgcaa aggtcaaact tgcctgccat atccttactg gagagatggt agctataaaa
121 atcatggata aaacacact agggagtgat ttgccccgga tcaaaacgga gattgaggcc
181 ttgaagaacc tgagacatca gcatatatgt caactctacc atgtgctaga gacagccaac
241 aaaatattca tggttcttga gggtaacaag gattaccatc tacagacatg ctgtgggagt
301 ctggcttatg cagcacctga gttaataaca ggcaaatcat atcttggatc agaggcagat
361 gtttggagca tgggcatact gttatatgtt cttatgtgtg gatttctacc atttgatgat
421 gataatgtaa tggctttata caagaagatt atgagaggaa atatgatgt tcccaagtgg
481 ctctctccca gtagcattct gcttcttcaa caaatgctgc aggtggaccc aaagaaacgg
541 atttctatga aaaatctatt gaaccatccc tggatcatgc aagattacaa ctatcctgtt
601 gagtggcaaa gcaagaatcc ttttattcac ctcgatgatg attgcgtaac agaacttttct
661 gtacatcaca gaaacaacag gcaaacaatg gaggatttaa tttcactgtg gcagtatgat
721 cacctcacgg ctacctatct tctgcttcta gccaagaagg ctcggggaaa accagttcgt
781 ttaaggcttt cttctttctc ctgtggacaa gccagtgcta ccccattcac agacatcaag
```

TABLE 1-continued

```
 841 tcaaataatt ggagtctgga agatgtgacc gcaagtgata aaaattatgt ggcgggatta
 901 atagactatg attggtgtga agatgattta tcaacaggtg ctgctactcc ccgaacatca
 961 cagtttacca agtactggac agaatcaaat ggggtggaat ctaaatcatt aactccagcc
1021 ttatgcagaa cacctgcaaa taaattaaag aacaaagaaa atgtatatac tcctaagtct
1081 gctgtaaaga atgaagagta cttttatgttt cctgagccaa agactccagt taataagaac
1141 cagcataaga gagaaatact cactacgcca aatcgttaca ctacaccctc aaaagctaga
1201 aaccagtgcc tgaaagaaac tccaattaaa ataccagtaa attcaacagg aacagacaag
1261 ttaatgacag gtgtcattag ccctgagagg cggtgccgct cagtggaatt ggatctcaac
1321 caagcacata tggaggagac tccaaaaaga aagggagcca aagtgtttgg gagccttgaa
1381 aggggggttgg ataaggttat cactgtgctc accaggagca aaaggaaggg ttctgccaga
1441 gacgggccca aagactaaa gcttcactat aacgtgacta caactagatt agtgaatcca
1501 gatcaactgt tgaatgaaat aatgtctatt cttccaaaga agcatgttga ctttgtacaa
1561 aagggttata cactgaagtg tcaaacacag tcagattttg ggaaagtgac aatgcaattt
1621 gaattagaag tgtgccagct tcaaaaaccc gatgtggtgg gtatcaggag gcagcggctt
1681 aagggcgatg cctgggttta caaaagatta gtggaagaca tcctatctag ctgcaaggta
1741 taa (SEQ ID NO:7)
```

Human MELK (isoform 4) Amino Acid Sequence (NP_001243617.1)
```
  1 mkdydellky yelhetigtg gfakvklach iltgemvaik imdkntlgsd lprikteiea
 61 lknlrhqhic qlyhvletan kifmvlegnk dyhlqtccgs layaapeliq gksylgsead
121 vwsmgillyv lmcgflpfdd dnvmalykki mrgkydvpkw lspssilllq qmlqvdpkkr
181 ismknllnhp wimqdynypv ewqsknpfih ldddcvtels vhhrnnrqtm edlislwqyd
241 hltatyllll akkargkpvr lrlssfscgq asatpftdik snnwsledvt asdknyvagl
301 idydwceddl stgaatprts qftkywtesn gvesksltpa lcrtpanklk nkenvytpks
361 avkneeyfmf pepktpvnkn qhkreilttp nryttpskar nqclketpik ivpnstgtdk
421 lmtgvisper rcrsveldln qahmeetpkr kgakvfgsle rgldkvitvl trskrkgsar
481 dgprrlklhy nvtttrlvnp dqllneimsi lpkkhvdfvq kgytlkcqtq sdfgkvtmqf
541 elevcqlqkp dvvgirrqr kgdawvykrl vedilssckv (SEQ ID NO:8)
```

Human MELK (isoform 5) cDNA Sequence (NM_001256689.1)
```
   1 atgatgaact tctcaaatat tatgaattac atgaaactat tgggacagag tgatttgccc
  61 cggatcaaaa cggagattga ggccttgaag aacctgagac atcagcatat atgtcaactc
 121 taccatgtgc tagagacagc caacaaaata ttcatggttc ttgagtactg ccctggagga
 181 gagctgtttg actatataat ttcccaggat cgcctgtcag aagaggagac ccgggttgtc
 241 ttccgtcaga tagtatctgc tgttgcttat gtgcacagcc agggctatgc tcacagggac
 301 ctcaagccag aaaatttgct gtttgatgaa tatcataaat taaagctgat tgactttggt
 361 ctctgtgcaa aacccaaggg taacaaggat taccatctac agacatgctg tgggagtctg
 421 gcttatgcag cacctgagtt aatacaaggc aaatcatatc ttggatcaga ggcagatgtt
 481 tggagcatgg gcatactgtt atatgttctt atgtgtggat ttcaccatt tgatgatgat
 541 aatgtaatgg ctttatacaa gaagattatg agaggaaaat atgatgttcc caagtggctc
 601 tctcccagta gcattctgct tcttcaacaa atgctgcagg tggacccaaa gaaacggatt
 661 tctatgaaaa atctattgaa ccatccctgg atcatgcaag attacaacta tctgttgag
 721 tggcaaagca agaatccttt tattcacctc gatgatgatt gcgtaacaga acttttctgta
 781 catcacagaa acaacaggca aacaatggag gatttaattt cactgtggca gtatgatcac
 841 ctcacggcta cctatcttct gcttctagcc aagaaggctc gggggaaacc agttcgtttta
 901 aggcttttctt cttttctcctg tggacaagcc agtgctaccc cattcacaga catcaagtca
 961 aataattgga gtctggaaga tgtgaccgca agtgataaaa attatgtggc gggattaata
1021 gactatgatt ggtgtgaaga tgatttatca acaggtgctg ctactccccg aacatcacag
1081 tttaccaagt actggacaga atcaaatggg gtggaactaa atcattaac tccagcctta
1141 tgcagaacac ctgcaaataa attaaagaac aaagaaatg tatatactcc taagtctgct
1201 gtaaagaatg aagagtactt tatgttcct gagccaaaga ctccagttaa taagaaccag
1261 cataagagag aaatactcac tacgccaaat cgttacacta cacccctcaa agctagaaac
1321 cagtgcctga agaaactcc aattaaaata ccagtaaatt caacaggaac agacaagtta
1381 atgacaggtg tcattagccc tgagaggcgg tgccgctcag tggaattgga tctcaaccaa
1441 gcacatatgg aggagactcc aaaaagaaag ggagccaaag tgtttgggag ccttgaaagg
1501 ggggttgata aggttatcac tgtgctcacc aggagcaaaa ggaagggttc tgccagagac
1561 gggcccagaa gactaaagct tcactataac gtgactacaa ctagattagt gaatccagat
1621 caactgttga tgaataat gtctattctt ccaaagaagc atgttgactt tgtacaaaag
1681 ggttatacac tgaagtgtca aacacagtca gattttggga aagtgacaat gcaatttgaa
1741 ttagaagtgt gccagcttca aaaacccgat gtggtgggta tcaggaggca gcggcttaag
1801 ggcgatgcct gggtttacaa agattagtgg aagacatcct atctagctg caaggtataa
     (SEQ ID NO:9)
```

Human MELK (isoform 5) Amino Acid Sequence (NP_001243618.1)
```
  1 mmnfsnimny mkllgqsdlp rikteiealk nlrhqhicql yhvletanki fmvleycpgg
 61 elfdyiisqd rlseeetrvv frqivsavay vhsqgyahrd lkpenllfde yhklklidfg
121 lcakpkgnkd yhlqtccqsl ayaapeliqg ksylgseadv wsmgillyvl mcgflpfddd
181 nvmalykkim rgkydvpkwl spssilllqq mlqvdpkkri smknllnhpw imqdynypve
241 wqsknpfihl dddcvtelsv hhrnnrqtme dlislwqydh ltatyllla kkargkpvrl
301 rlssfscgqa satpftdiks nnwsledvta sdknyvagli dydwceddls tggatprtsq
361 ftkywtesng vesksltpal crtpanklkn kenvytpksa vkneeyfmfp epktpvnknq
421 hkreilttpm ryttpskarn qclketpiki pvnstgtdkl mtgvisperr crsveldlnq
481 ahmeetpkrk gakvfgsler gldkvitvlt rskrkgsard gprrlklhyn vtttrlvnpd
541 qllneimsil pkkhvdfvqk gytlkcqtqs dfgkvtmqfe levcqlqkpd vvgirrqrlk
601 gdaqvykrlv edilssckv (SEQ ID NO:10)
```

Human MELK (isoform 6) cDNA Sequence (NM_001256690.1)
```
  1 atgatgaact tctcaaatat tatgaattac atgaaactat tgggacagta ctgccctgga
 61 ggagagctgt ttgactatat aatttcccag gatcgcctgt cagaagagga gacccgggtt
121 gtcttccgtc agatagtatc tgctgttgct tatgtgcaca gccagggcta tgctcacagg
```

TABLE 1-continued

```
 181 gacctcaagc cagaaaattt gctgtttgat gaatatcata aattaaagct gattgacttt
 241 ggtctctgtg caaaacccaa gggtaacaag gattaccatc tacagacatg ctgtgggagt
 301 ctggcttatg cagcacctga gttaatacaa ggcaaatcat atcttggatc agaggcagat
 361 gtttggagca tgggcatact gttatatgtt cttatgtgtg gatttctacc atttgatgat
 421 gataatgtaa tggctttata caagaagatt atgagaggaa aatatgatgt tcccaagtgg
 481 ctctctccca gtagcattct gcttcttcaa caaatgctgc aggtggaccc aaagaaacgg
 541 atttctatga aaaatctatt gaaccatccc tggatcatgc aagattacaa ctatcctgtt
 601 gagtggcaaa gcaagaatcc ttttattcac ctcgatgatg attgcgtaac agaactttct
 661 gtacatcaca gaaacaacag gcaaacaatg gaggatttaa tttcactgtg gcagtatgat
 721 cacctcacgg ctacctatct tctgcttcta gccaagaagg ctcgggaaa accagttcgt
 781 ttaaggcttt cttctttctc ctgtggacaa gccagtgcta cccattcac agacatcaag
 841 tcaaataatt ggagtctgga agatgtgacc gcaagtgata aaaattatgt ggcgggatta
 901 atagactatg attggtgtga agatgattta tcaacaggtg ctgctactcc ccgaacatca
 961 cagtttacca agtactggac agaatcaaat gggggtggaa ctaaatcatt aactccagcc
1021 ttatgcagaa cacctgcaaa taattaaag aacaaagaaa atgtatatac tcctaagtct
1081 gctgtaaaga atgaagagta ctttatgttt cctgagccaa agactccagt taataagaac
1141 cagcataaga gagaaatact cactacgcca aatcgttaca ctacaccctc aaaagctaga
1201 aaccagtgcc tgaaagaaac tccaattaaa ataccagtaa attcaacagg aacagacaag
1261 ttaatgacag gtgtcattag ccctgagagg cggtgccgct cagtggaatt ggatctcaac
1321 caagcacata tggaggagac tccaaaaaga aagggagcca aagtgttttgg gagccttgaa
1381 agggggttgg ataaggttat cactgtgctc accaggagca aaaggaaggg ttctgccaga
1441 gacgggccca aagactaaa gcttcactat aacgtgacta caactagatt agtgaatcca
1501 gatcaactgt tgaatgaaat aatgtctatt cttccaaaga agcatgttga ctttgtacaa
1561 aagggttata cactgaagtg tcaaacacag tcagattttg ggaaagtgac aatgcaattt
1621 gaattagaag tgtgccagct tcaaaaaccc gatgtggtgg gtatcaggag gcagcggctt
1681 aagggcgatg cctgggttta caaagatta gtggaagaca tcctatctag ctgcaaggta
1741 taa (SEQ ID NO:11)
```

Human MELK (isoform 6) Amino Acid Sequence (NP_001243619.1)
```
   1 mmnfsnlmny mkllgqycpg gelfdyiisq drlseeetrv vfrqivsava yvhsqgyahr
  61 dlkpenllfd eyhklklidf glcakpkgnk dyhlqtccgs layaapelig gksylgsead
 121 vwsmgillyv lmcgflpfdd dnvmalykki mrgkydvpkw lspssillllq qmlqvdpkkr
 181 ismknllnhp wimqdynypv ewqsknpfih ldddcvtels vhhrnnrqtm edlislwqyd
 241 hltatylllll akkargkpvr lrlssfscgq asatpftdik snnwsledvt asdknyvagl
 301 idydwceddl stgaatprts qftkywtesn gveskslltpa lcrtpanlkl nkenvytpks
 361 avkneeyfmf pepktpvnkn qhkrellttp nryttpskar nqclketpil ipvnstgtdk
 421 lmtqvisper rcrsveldln qahmeetpkr kgakvfgsle rgldkvitvl trskrkgsar
 481 dgprrlklhy nvttrlvnp dqllneimsi lpkkhvdfvg kgytlkcqtq sdfgkvtmqf
 541 elevcqlqkp dvgirrqrl kgdawvykrl vedilsscky (SEQ ID NO:12)
```

Human MELK (isoform 7) cDNA Sequence (NM_001256691.1)
```
   1 atgatgaact tctcaaatat tatgaattac atgaaactat tgggacagag tgatttgccc
  61 cggatcaaaa cggagattga ggccttgaag aacctgagac atcagcatat atgtcaactc
 121 taccatgtgc tagagacagc caacaaaata ttcatggttc ttgaggaaaa tttgctgttt
 181 gatgaatatc ataaattaaa gctgattgac tttggtctct gtgcaaaacc caagggtaac
 241 aaggattacc atctacagac atgctgtggg agtctggctt atgcagcacc tgagttaata
 301 caaggcaaat catatcttgg atcagaggca gatgtttgga gcatgggcat actgttatat
 361 gttctttatgt gtggatttct accatttgat gatgataatg taatggcttt atacaagaag
 421 attatgagag gaaaatatga tgttcccaag tggctctctc ccagtagcat tctgcttctt
 481 caacaaatgc tgcaggtgga cccaaagaaa cggatttcta tgaaaaatct attgaaccat
 541 ccctcgatca tgcaagatta caactatcct gttgagtggc aaagcaagaa tcctttttatt
 601 cacctcgatg atgattgcgt aacagaactt tctgtacatc acagaaacaa caggcaaaca
 661 atggaggatt taatttcact gtggcagtat gatcacctca cggctaccta tcttctgctt
 721 ctagccaaga aggctcgggg aaaaccagtt cgtttaaggc tttcttcttt ctcctgtgga
 781 caagccagtg ctaccccatt cacagacatc aagtcaaata attggagtct ggaagatgtg
 841 accgcaagtg ataaaaatta tgtggcggga ttaatagact atgattggtg tgaagatgat
 901 ttatcaacag gtgctgctac tccccgaaca tcacagttta ccaagtactg gacagaatca
 961 aatgggggtgg aatctaaatc attaactcca gccttatgca gaacacctgc aaataaaatta
1021 aagaacaaag aaaatgtata tactcctaag tctgctgtaa agaatgaaga gtactttatg
1081 tttcctgagc caaagactcc agttaataag aaccagcata gagagaaat actcactacg
1141 ccaaatcgtt acactacacc ctcaaaagct agaaaccagt gcctgaaaga aactccaatt
1201 aaaataccag taaattcaac aggaacagac aagttaatga caggtgtcat tagccctgag
1261 aggcggtgcc gctcagtgga attggatctc aaccaagcac atatggagga gactccaaaa
1321 agaaagggag ccaaagtgtt tgggagcctt gaaagggggt tggataaggt tatcactgtg
1381 ctcaccagga gcaaaaggaa gggtctgcc agagacgggc ccaaagact aaagcttcac
1441 tataacgtga ctacaactag attagtgaat ccagatcaac tgttgaatga aataatgtct
1501 attcttccaa agaagcatgt tgactttgta caaaagggtt atacactgaa gtgtcaaaca
1561 cagtcagatt ttgggaaagt gacaatgcaa tttgaattag aagtgtgcca gcttcaaaaa
1621 cccgatgtgg tgggtatcag gaggcagcgg cttaagggcg atgcctgggt ttacaaaaga
1681 ttagtggaag acatcctatc tagctgcaag gtataa (SEQ ID NO:13)
```

Human MELK (isoform 7) Amino Acid Sequence (NP_001243620.1)
```
   1 mmnfsnimny mkllgqsdlp rikteiealk nlrhqhicql yhvlecanki fmvleenllf
  61 deynklklid fglcakpkgn kdyhlgtccg slayaapeli qgksylgsea dvwsmgilly
 121 vlmcgflpfd ddnvmalykk imrgkydvpk wlspssilll qqmlqvdpkk rismknllnh
 181 pwimqdynyp vewqsknpfi hldddcvtel svhhrnnrqt medlislwqy dhltatyllll
 241 lakkargkpv rlrlssfscg qasatpftdi ksnnwsledv tasdknyvag lidydwcedd
 301 lstgaatpst sqftkywtes ngvesksltp alcrtpankl knkenvytpk savkneeyfm
 361 fpepktpvnk nqkkreiltt pnryttppska rnqclketpi kipvnstgtd klmtqgvispe
 421 rrcrsveldl nqahmeetpk rkgakvfgsl ergldkvitv ltrskrkgsa rdprrlklh
```

TABLE 1-continued 481 ynvtttrlvn pdqllneims ilpkknvdfv qkgyfgvtmp qsdfgkvtmg felevcqlqk
541 pdvvgirrqr lkgdawvykr lvedilssck v (SEQ ID NO:14)

Human MELK (isoform 8) cDNA Sequence (NM_001256692.1)
```
    1 atggttcttg aggaaaattt gctgtttgat gaatatcata aattaaagct gattgactttt
   61 ggtctctgtg caaaacccaa gggtaacaag gattaccata tacagacatg ctgtgggagt
  121 ctggccttatg cagcacctga gttaatacaa ggcaaatcat atcttggatc agaggcagat
  181 gtttggagca tgggcatact gttatatgtt cttatgtgtg gatttctacc atttgatgat
  241 gataatgtaa tggctttata caagaagatt atgagaggaa aatatgatgt tcccaagtgg
  301 ctctctccca gtagccattc gcttcttcaa caaatgctgc aggtggaccc aaagaaacgg
  361 atttctatga aaaatctatt gaaccatccc tggatcatgc aagattacaa ctatcctgtt
  421 gagtggcaaa gcaagaatcc ttttattcac ctcgatgatg attgcgtaac agaactttct
  481 gtacatcaca gaaacaacag gcaaacaatg gaggatttaa tttcactgtg gcagtatgat
  541 cacctcacgg ctacctatct tctgcttcta gccaagaagg ctcgggaaa accagttcgt
  601 ttaaggcttt cttctttctc ctgtggacaa gccagtgcta ccccattcac agacatcaag
  661 tcaaataatt ggagtcggaa gatgtgacc gcaagtgata aaaattatgt ggcgggatta
  721 atagactatg attggtgtga agatgattta tcaacaggtg ctgctactcc ccgaacatca
  781 cagtttacca agtactggac agaatcaaat gggtgaat ctaaatcatt aactccagcc
  841 ttatgcagaa cacctgcaaa taaattaaag aacaaagaaa atgtatatac tcctaagtct
  901 gctgtaaaga atgaagagta ctttatgttt cctgagccaa agactccagt taataagaac
  961 cagcataaga gagaaatact cactacgcca aatcgttaca ctacaccctc aaaagctaga
 1021 aaccagtgcc tgaaagaaac tccaattaaa ataccagtaa attcaacagg aacagacaag
 1081 ttaatgacag gtgtcattag ccctgagagg cggtgccgct cagtggaatt ggatctcaac
 1141 caagcacata tggaggagac tccaaaaga aagggagcca aagtgtttgg gagccttgaa
 1201 aggggttgg ataaggttat cactgtgctc accaggagca aaggaaggg ttctgccaga
 1261 gacgggccca gaagactaaa gcttcactat aacgtgacta caactagatt agtgaatcca
 1321 gatcaactgt tgaatgaaat aatgtctatt cttccaaaga agcatgttga ctttgtacaa
 1381 aagggttata cactgaagtg tcaaacacag tcagattttg ggaaagtgac aatgcaattt
 1441 gaattagaag tgtgccagct tcaaaaaccc gatgtggtgg gtatcaggag gcagcggctt
 1501 aagggcgatg cctgggttta caaagatta gtggaagaca tcctatctag ctgcaaggta
 1561 taa (SEQ ID NO:15)
```

Human MELK (isoform 8) Amino Acid Sequence (NP_001243621.1)
```
    1 mvleenllfd eyhklklidf glcakpkgnk dyhlqtccgs layaapeliq gksylgsead
   61 vwsmgillyv lmcgflpfdd dnvmalykkl mrgkydvpkw lspssilllq qmlqvdpkkr
  121 ismknllnhp wimqdynypv ewqsknpfih ldddcvtels vhhrnnrqtm edlislwqyd
  181 hltatyllll akkargkpvr lrlssfscgq asatpftdik snnwsledvt asdknyvagl
  241 idydwceddl stgaatprts qftkywtesn gveskslltpa lcrtpanklk nkenvytpks
  301 avkneeyfmf pepktpvnkn qhkreilttp nryttpskar nqclketpik ipvnstgtdk
  361 lmtgvisper rcrsveldln qahmeetpkr kgakvfgsle rgldkvitvl trskrkgsar
  421 dgprrlklhy nvtttrlvnp dqllneimsi lpkkhvdfvq kgytlkcqtq sdfgkvtmqf
  481 elevcqlqkp dvvgirrqrl kgdawvykrl vedilsscky (SEQ ID NO:16)
```

Human MELK (isoform 9) cDNA Sequence (NM_001256693.1)
```
    1 atgggcatac tgttatatgt tcttatgtgt ggatttctac catttgatga tgataatgta
   61 atggctttat acaagaagat tatgagagga aaatatgatg ttcccaagtg gctctctccc
  121 agtagcattc tgcttcttca acaaatgctg caggtggacc caaagaaacg gatttctatg
  181 aaaaatctat tgaaccatcc ctggatcatg caagattaca actatcctgt tgagtggcaa
  241 agcaagaatc cttttattca cctcgatgat gattgcgtaa cagaactttc tgtacatcac
  301 agaaacaaca ggcaaacaat ggaggattta atttcactgt ggcagtatga tcacctcacg
  361 gctacctatc ttctgcttct agcaagaag gctcggggaa aaccagttcg tttaaggctt
  421 tcttctttct cctgtggaca agccagtgct accccattca cagacatcaa gtcaaataat
  481 tggagtctgg aagatgtgac cgcaagtgat aaaaattatg tggcgggatt aatagactat
  541 gattggtgtg aagatgattt atcaacaggt gctgctactc cccgaacatc acagtttacc
  601 aagtactgga cagaatcaaa tggggtggaa tctaaatcat taactccagc cttatgcaga
  661 acacctgcaa ataaattaaa gaacaaagaa aatgtatata ctcctaagtc tgctgtaaag
  721 aatgaagagt actttatgtt tcctgagcca agactccag ttaataagaa ccagcataag
  781 agagaaatac tcactacgcc aaatcgttac actacaccct caaaagctag aaaccagtgc
  841 ctgaaagaaa ctccaattaa ataccagta aattcaacag gaacagacaa gttaatgaca
  901 ggtgtcatta gccctgagag gcggtgccgc tcagtggaat tggatctcaa caagcacat
  961 atggaggaga ctccaaaaag aaagggagcc aaagtgtttg gagccttga aggggggttg
 1021 gataaggtta tcactgtgct caccaggagc aaaggaagg gttgccag agacgggccc
 1081 agaagactaa agcttcacta taacgtgact acaactagat tagtgaatcc agatcaactg
 1141 ttgaatgaaa taatgtctat tcttccaaag aagcatgttg actttgtaca aaagggttat
 1201 acactgaagt gtcaaacaca gtcagatttt gggaaagtga caatgcaatt tgaattagaa
 1261 gtgtgccagc ttcaaaaacc cgatgtggtg gtatcagga ggcagcggct taagggcgat
 1321 gcctgggttt acaaaagatt agtggaagac atcctatcta gctgcaaggt ataa
          (SEQ ID NO:17)
```

Human MELK (isoform 9) Amino Acid Sequence (NP_001243621.1)
```
    1 mgillyvlmc gflpfdddnv malykkimrg kydvpkwlsp ssilllqqml qvdpkkrism
   61 knllnhpwim qdynypvewq sknpfihldd dcvtelsvhh rnnrqtmedl islwqydhlt
  121 atylllakk argkpvrlrl ssfscgqasa tpftdiksnn wsledvtasd knyvaglidy
  181 dwceddlstg aatprtsqft kywtesngve skslltpalcr tpanklknke nvytpksavk
  241 neeyfmfpep ktpvnknqhk reilttpnry ttpskarnqc lketpikipv nstgtdklmt
  301 givsperrcr sveldlngah meetpkrkga kvfgslergl dkvitvltrs krkgsardgp
  361 rrlklhynvt ttrlvnpdql lneimsilpk khvdfvqkgy tlkcqtqsdf qkvtmqfele
  421 vcqlqkpdvv girrqrlkgd awvykrlived ilssckv (SEQ ID NO:18)
```

TABLE 1-continued

Mouse MELK cDNA Sequence (NM_010790.2)
```
   1 atgaaagatt atgacgaact cctcaaatac tatgaactat atgaaacgat tgggacaggt
  61 ggctttgcaa aggtcaaact ggcctgccat gtcctcactg gagagatggt agctatataa
 121 atcatggata aggatgcgct agggagtgat ttgccccgag tcaaaactga gatcgatgcg
 181 ctgaagagtc tgagacatca gcacatatgt cagctctacc atgtgctgga gacaaagaac
 241 aaaatattca tggttctgga gtactgtcca ggaggagagc tgtttgacta cataatctcc
 301 caggatcgcc tgtcggaaga ggagacccgg gtcgtcttcc gtcagatact gtctgcagtt
 361 gcgtatgtcc acagccaggg ctatgcccac agggacctca aaccagaaaa tttattattt
 421 gatgaaaatc ataagctaaa gctgattgac tttggtcttt gtgcaaaacc caagggcaac
 481 aaggactacc atctgcagac gtgctgtggg agcctgctc atgcagctcc tgaactaata
 541 caagggaagt cgtaccttgg atcagaggca gatgtttgga gcatgggcat cctcctgtat
 601 gtgctcatgt gtggatttct accatttgat gatgataatg tcatggcttt gtacaagaag
 661 ataatgagag ggaaatacga agttcctaag tggctctctc ccagtagcat tctgcttctc
 721 cagcagatgt tgcaggtgga cccaaagaaa cggatttcta tgagaaatct cctgaaccat
 781 ccctgggtca tgcaagatta cagctgtccc gtggagtggc aaagcaagac tcctttgact
 841 cacctcgatg aggattgcgt gacagagctt tctgtacatc accgcagcag caggcagaca
 901 atggaggatt taatttcgtc gtggcagtac gatcacctca cagccaccta cctctgcttt
 961 ctagccaaga aggcccgggg gaagccggct cgtcacagc tcctgtcctt ctcttgtgga
1021 accgccagca ccactccaaa gtcaaagaat ctgagcctgg aagatatgag cacaagtgat
1081 gataactgtg tggctggatt gatagactat gaattgtgtg aagataaatt attagctccc
1141 aagacgccac aggttaccaa acacttggca gaatcaaatc acgcagcatc taaatcacca
1201 gcgccagggg tacgcagagc agtggcaaat aaattaatgg acaaagaaaa tgtgtgcact
1261 cccaagtctt ctgtgaagaa tgaagaacag tttgtatttt ctgagccgaa gattccagtt
1321 agtaagaacc agtataagag agaaataccc gcctcaccaa cccgtttcc aacacctgca
1381 aaagctagag cccagtgcct gagagaagcc ccggttagaa caccagggaa ttccgcagga
1441 gcagacacac taacgacagg tgtcattagc cccgagagga ggtgccgttc aatggacgtg
1501 gatctcaacc aggcacacat ggaggatacc ccgaaaaaga aggaaccaa tgtgtttggg
1561 agccttgaga ggactggaa taaggttctc actgcgctca caaggaacaa gaagaagggc
1621 tctgccagag atggaccaag aaagcgaaag ctgcactaca atgtgactac aactcgcctg
1681 gtgaaccccg accagctcct gagcgaaatc atggctattc ttccaaagaa gaacgtggac
1741 ttcgtacaga aaggttacac tctaaagtgt caaacgcagt gtgatttgg caagtgaca
1801 atgcagtttg aactggaagt gtgccagctg cagagacctg acgtggtagg catccggaga
1861 cagcggctga agggtgatgc ctgggtttac aagagattag tggaagatat cttgtctggc
1921 tgcaagatgt ga (SEQ ID NO:19)
```

Mouse MELK Amino Acid Sequence (NP_034920.2)
```
   1 mkdydellky yelyetigtg gfakvklach vltgemvaik imdknalgsd lprvkteida
  61 lkslrhqhic qlyhvletkn kifmvleycp ggelfdyiis qdrlseeetr vvfrqilsav
 121 ayvhsqgyah rdlkpenllf denhklklid fglcakpkgn kdyhlqtccg slayaapeli
 181 qgksylgsea dvwsmgilly vlmcgflpfd ddnvmalykk imrgkyevpk wlspssilll
 241 qqmlqvdpkk rismrnllnh pwvmqdyscp vewqsktplt hldedcvtel svhhrssrqt
 301 medlisswqy dhltatylll lakkargkpa rlqllsfscg tasttpkskn lsledmstsd
 361 dncvaglidy elcedkllap ktpqvtkhla esnhaasksp apgvrravan klmdkenvct
 421 pkssvkneeq fvfsepkipv sknqykreip asptrfptpa karaqclrea pvrtpgnsag
 481 adtlttgvis perrcrsmdv dlngahmedt pkkkgtnvfg slergldkvl taltrnkkkg
 541 sardgprkrk lhynvtttrl vnpdqllsei mailpkknvd fvqkgytlkc qtqsdfgkvt
 601 mqfeleveql qrpdvvgirr qrlkgdawvy krlvedilsg ckm (SEQ ID NO:20)
```

Human eIF4B cDNA Sequence (NM_001417.4)
```
   1 atggcggct cagcaaaaaa gaagaataag aaggggaaga ctatctccct aacagacttt
  61 ctggctgagg atggggtac tggtggagga agcacctatg tttccaaacc agtcagctgg
 121 gctgatgaaa cggatgacct ggaaggagat gtttcgacca cttggcacag taacgatgac
 181 gatgtgtata gggcgcctc aattgaccgt tccatccttc ccactgctcc acgggctgct
 241 cgggaaccca atatcgaccg gagccgtctt cccaaatcgc caccctacac tgcttttcta
 301 ggaaacctac cctatgatgt tacagaagag tcaattaagg aattctttcg aggattaaat
 361 atcagtgcag tgcgtttacc acgtgaaccc agcaatccag agaggttgaa aggttttggt
 421 tatgctgaat tgaggacct ggattccctg ctcagtgccc tgagtctcaa tgaagagtct
 481 ctaggtaaca ggaagaattcg agtggacgtt gctgatcaag cacaggataa agactggagg
 541 gatcgttctt ttggccgtga tagaaatcgg gattctgaca aaacagatac agactggagg
 601 gctcgtcctg ctacagacga ctttgatgac taccaccta aagagagtga tgatagctttt
 661 ggagacaagt atcgagatcg ttatgattca gaccggtatc gggatgggta tcgggatggg
 721 tatcgggatg gcccacgccg ggatatggat cgatatggtg gccgggatcg ctatgatgac
 781 cgaggcagtg gagactatga tagggctat gattcccgga taggcagtgg cagaagagca
 841 tttggcagtg ggtatcgcag ggatgatgac tacagaggag gcggggaccg ctatgaagac
 901 cgatatgaca gacgggatga tcggtcgtgg agtccagag atgattctc tcgggatgat
 961 tataggcgtg atgataagg tccccccaa agacccaaac tgaatctaaa gcctcggagt
1021 actcctaagg aagatgattc ctctgctagt acctcccagt ccactcgagc tgcttctatc
1081 tttggagggg caaagcctgt tgacacagct gctagagaaa gaagtagaa agaacggcta
1141 cagaaggaac aagagaagtt gcgcgtcag ctggatgagc caaaactaga acgacggcct
1201 cgggagagac acccaagctg gcgaagtgaa gaaactcagg aacgggaacg gtcgaggaca
1261 ggaagtgagt catccaaaac tgggacctcc accacatcta gcagaaatgc acgaaggaga
1321 gagagtgaga agtctctaga aatgaaaca ctcaataagg aggaagattg ccactctcca
1381 acttctaaac ctctcaaatc tgatcagccc ctaaaggtaa tgcagccc tccaccaaag
1441 gagaatgctt gggtgaagcg aagttctaac cctcctgctc gatctcagag ctcagacaca
1501 gagcagcagt cccctacaag tggtggggga aaagtagctc cagtcaacc atctgaggaa
1561 ggaccaggaa ggaaagatga aaataaagta gatgggatga atgcccaa aggcaaact
1621 gggaactcta gccgtggtcc aggagacggg gggacagag accactggaa ggagtcagat
1681 aggaaagatg gcaaaaagga tcaagactcc agatctgcac ctgagccaaa gaaacctgag
```

TABLE 1-continued

```
1741 gaaaatccag cttccaagtt cagttctgca agcaagtatg ctgctctctc tgttgatggt
1801 gaagatgaaa atgagggaga agattatgcc gaatag (SEQ ID NO:21)
```

Human eIF4B Amino Acid Sequence (NM_001408.2)
```
  1 maasakkknk kgktisltdf laedggtggg styvskpvsw adetddlegd vsttwhsndd
 61 ctagctgagg atggaggaac tggtggagga agcacctatg tccccaaacc agtcagctgg
121 isavrlprep snperlkgfg yaefedldsl lsalslnees lgnrrirvdv adqaqdkdrd
181 drsfgrdrnr dsdktdtdwr arpatdsfdd ypprrgddsf gdkyrdryds dryrdgyrdg
241 yrdgprrdmd ryggrdrydd rgsrdyrdgy dsrigsgrra fgsgyrrddd yrgggdryed
301 rydyyddrsw ssrddysrdd yrrddrgppq rpklnlkprs tpkeddssas tsqstraasi
361 fggakpvdta arereveerl qkeqeklqrg ldepklerrp rerhpswrse etqerersrt
421 gsessqtgts ttssrnarrr esekslenet lnkeedchsp tskppkpdqp lkvmpapppk
481 enawvkrssn pparsqssdt eqqsptsggg kvapaqpsee gpgrkdenkv dgmnapkgqt
541 gnssrgpgdg gnrdhwkesd rkdgkkdqds rsapepkkpe enpaskfssa skyaalsvdg
601 edenegedya e (SEQ ID NO:22)
```

Human eIF4B cDNA Sequence (NM_145625.3)
```
    1 atggcggcct cagcaaaaaa gaagaataag aaggggaaga ccatctccct aacggacttt
   61 ctagctgagg atggaggaac tggtggagga agcacctatg tccccaaacc agtcagctgg
  121 gctgatgaaa cagacgatct ggaaggagat gtgtcaacaa cttggcatag taacgatgat
  181 gacgtgtaca gggcgcctcc aattgaccgt tccatccttc ccactgctcc acgggctgct
  241 cgggaaccca atattgaccg gagccgtctt cccaagtcgc caccctacac tgctttccta
  301 gggaatctgc cctatgatgt gacagaagac tccattaagg atttctttag aggattaaat
  361 atcagcgctg tacgcttacc acgggaaccc agcaatccag acaggttgaa aggtttcggc
  421 tacgcagaat ttgaggacct ggattctgtc ctcagtgctc tgagtctcaa tgaagagtct
  481 ctaggtaaca ggagaattcg tgtggatgtt gctgatcaag cacaggataa agacagggat
  541 gaccgttctt ttggtcgaga tagaaatcgg gattctgaca aaacagacac agactggagg
  601 gcccgtccca ccacagacag ttttgatgac tacccaccta agagggcga tgatagcttt
  661 ggagacaagt atcgagatcg ttacgattca gaccggtatc gggatgggta tagggacgga
  721 tatcgggacg gcccacgcag agacatggac cgctatgggg gccgggatcg ctatgatgac
  781 cgaggcagca gagactatga ccgaggctat gactccagga taggcagtgg cagaagggca
  841 ttttggaagtg ggtaccggag agatgatgac tacagaggag gtggggaccg ctatgaagac
  901 cgctatgaca gacgggatga tcggtcgtgg agctccaggg atgactactc tcgggatgat
  961 tataggcgtg atgacagagg tccccccag agacccgac tgaacctcaa gcctcgaagc
 1021 gctcctaagg aggatgacgc ctccgccagc acctccagt ccagccggc agcctccatc
 1081 ttttggagggg cgaagcctgt tgacacagct gctagggaaa gagaagtaga ggagcggcta
 1141 cagaaggagc aggagaagct gcagcgtcag ctggatgagc aaaactaga ccgccggccc
 1201 cgggagagac acccaagctg gcgaagtgaa gaaactcagg aaagagaacg gtcaaggaca
 1261 ggaagtgagt catcgcagac tggggcctca gccacatctg gcagaaatac acgaaggaga
 1321 gagagtgaga agtctctaga aaatgaaacc ctcaataaag aagaagactg tcactctcca
 1381 acctctaagc ctcctaaacc tgaccagcct gtaaaggtaa tgccagcccc tccaccaaag
 1441 gagaatgcgt gggtgaagcg aagctctaac cctcctgccc gatctcagag ctcagacaca
 1501 gagcagccgt ccctacaag tggtggaggg aaagtagctg cagtccagcc cctgaggaa
 1561 ggaccatcaa gaaaagatgg aaataaagtg gatgtggtgg gtgccacaca aggccaagct
 1621 ggaagctgca gccgtggtcc cggggatgga gggagcagag accactggaa ggacttggat
 1681 aggaaggatg gcaaaaaaga tcaagactcc agatctgcgc ctgagccaaa gaaacctgag
 1741 gagaacccag cctctaagtt cagctctgca agcaagtacg ctgctctgtc tgtggatggc
 1801 gaggatgagg atgagggcga cgactgcact gagtag (SEQ ID NO:23)
```

Human eIF4B Amino Acid Sequence (NM_663600.2)
```
  1 maasakkksk kgktisltdf laedggtggg styvpkpvsw adetddlegd vsttwhsndd
 61 dvyrappidr silptapraa repnidrsrl pksppytafl gnlpydvted sikdffrgln
121 isavrlprep snprlkgfg yaefedldsl lsalslnees lgarrlrvdv adqaqdkdrd
181 drsfgrdrnr dsdktdtdwr arpttdsfdd ypprrgddsf gdkyrdryds dryrdgyrdg
241 yrdgprrdmd ryggrdrydd rgsrdydrgy dsrigsgrra fgsgyrrddd yrgggdryed
301 rydrrdddrsw ssrddysrdd yrrddrgppq rprlnlkprs apkeddasas tsqssraasi
361 fggakpvdta arereveerl qkeqeklqrq ldepkldrrp rerhpswrse etqerersrt
421 qsessqtgas pparsqssdt esekslenet lnkeedchsp tskppkpdqp lkvmpapppk
481 enawvkrssn pparsqssdt eqpsptsggg kvaavqppee gpsrkdgnkv dvvgatqgqa
541 gscsrgpgdg gsrdhwkdld rkdgkkdqds rsapepkkpe enpaskfssa skyaalsvdg
601 ededegddct e (SEQ ID NO:24)
```

Human eIF4B cDNA Sequence (NM_001195808.1)
```
    1 ctctcccaac atggcggcct cagcaaaaaa gaagaataag aaggggaaga ctatctccct
   61 aacagacttt ctagctgagg atggggggtac tggtggagga agcacctatg tttccaaacc
  121 agtcagctgg gctgatgaaa cggatgacct ggaaggagat gtttcaacaa cgtggcacag
  181 taatgacgac gatgtgtaca gggcgcctcc aattgaccgt tccatccttc ccactgctcc
  241 acgggctgct cgggaaccca atattgaccg gagccgtctt cccaaatcgc caccctacac
  301 tgcttttccta gggaacctac cctatgatgt gacagaagaa tcaattaagg aattctttag
  361 aggattaaat atcagtgcag tgcgtttacc acgtgaaccc agcaatccag agaggttgaa
  421 aggttttggt tatgctgaat tgaggacct ggattccctg ctcagtgccc tgagtctcaa
  481 tgaagagtct ctaggtaaca ggagaattcg agtggacgtt gctgatcaag cacaggataa
  541 agacagggat gatcgttctt ttggccgtga tagaaatcgg gattctgaca aaacagatac
  601 agactggagg gctcgtcctg ctacagacag cttttgatgac tacccaccta agagggtga
  661 tgatagcttt ggagacaagt atcgagatcg ttatgattca gaccggtatc gggatgggta
  721 tcgggatgga ccacgccggg atatggatcg atatggtggc cgggatcgct atgatgaccg
  781 aggcagcaga gactatgata ggctatga ttccggata ggcagtgca gaaagcatt
  841 tggcagtggg tatcgcaggg atgatgacta cagaggaggc ggggaccgat atgaagaccg
  901 atacgacaga cgggatgatc ggtcgtggag ctccagagat gattactctc gggatgatta
  961 taggcgcgat gacagaggtc cccctcaaag acccaaactg aatctaaagc ctcggagtac
```

TABLE 1-continued

```
1021 tcctaaggaa gatgattcct ctgctagtac ctcccagtcc agtagagctg cttctatctt
1081 tggaggggca aagcctgttg acacagctgc tagagaaaga gaagtagaag aacggctaca
1141 gaaggaacaa gagaagttgc agcgtcagct ggatgagcca aaactagaac gacggcctcg
1201 ggagagacac ccaagctggc gaagtgaaga aactcaggaa cgggaacggt cgaggacagg
1261 aagtgagtca tcacagactg ggacctccgc cacatctggc agaaatgcac gaaggagaga
1321 gagtgagaag tctctagaaa atgaaacact caataaggag gaagattgtc actctccaac
1381 ttctaaacct cccaaacctg atcagcccct aaaggtaatg ccagcccctc caccaaagga
1441 gaatgcttgg gtgaagcgaa gttctaaccc tccagctcga tctcagagct cagacacaga
1501 gcagcaatcc cctacaagtg gtgggggaaa agtagctcca gctcaaccat ctgaggaagg
1561 accagcaagg aaagatgaaa ataaagtaga tgggatgaat gtcccaaaag gccaaactgg
1621 gacctctagc cgtggaccag gagacggagg gaacaaagac cactggaagg agtcagatag
1681 gaaagatggc aaaaaggatc aagactccag atctgcacct gagccaaaga aacctgagga
1741 aaatccagct tcgaagttca gttctgcaag caagtatgct gctctctctg ttgatggtga
1801 agatgaaaac gagggagaag attatgccga atagacctct acatcctgtg ctttctccta
1861 gtttctctcc accctggaac attcgagagc aaatcaaaac ctctatccag acaagacaaa
1921 ataaaactca ccatctcctg aagacctttc ttacctttt ttaaaaacaa aaaatgaaat
1981 tattttgcat gctgctgcag cctttaaagt attaaagtaa ctggagaatc gccaatatag
2041 ccagagagaa agggactaca gcttttagaa ggaagagttg tggtgtgtta (SEQ ID NO:25)
```

Monkey eIF4B Amino Acid Sequence (NP_001182737.1)

```
  1 maasakkknk kgktisltdf laedggtggg styvskpvsw adetddlegd vsttwhsndd
 61 dvyrappidr silptapraa repnidrsrl pksppytafl gnlpydvtee sikeffrgln
121 isavrlprep snperlkgfg yaefedldsl lsalslnees lgnrrirvdv adqaqdkdrd
181 drsfgrdrnr dsdktdtdwr arpatdsfdd ypprrgddsf gdkyrdryds dryrdgyrdg
241 prrdmdrygg rdryddrgsr dydrgydsrl gsgrrafgsg yrrdddyrgg gdryedrydr
301 rddrswssrd dysrddyrrd drgppqrpkl nlkprstpke ddssastsqs sraasifgga
361 kpvdtaarer eveeerlqkeq eklqrqldep klerrprerh pswrseetqe rersrtgses
421 sqtgtsatsg rnarrresek slenetlnke edchsptdkp pkpdqplkvm papppkenaw
481 vkrssnppar sqssdteqqs ptsgggkvap aqpseeqpar kdenkvdgmn vpkgqtgtss
541 rgpgdggnkd hwkesdrkdg kkdqdsrsap epkkpeenpa skfssaskya alsvdgeden
601 egedyae (SEQ ID NO:26)
```

Cow eIF4B cDNA Sequence (NM_001035028.2)

```
  1 atggcggcct cagcgaaaaa gaagaataag aaggggaaga ctatctccct aacagacttt
 61 ctggctgagg atggagggac tggtggaggc agcacctatg tccccaaacc agtcagctgg
121 gctgatgaaa cagacgatct ggaaggggat gtttcaacca cttggcatag taatgatgat
181 gatgtgtatc gggcacctcc aattgaccgt tccatcctgc ccactgctct acgggctgct
241 cgggaaccca atatcgaccg gagccgtctt cccaaatctc caccctacac tgcttttcta
301 gggaacctgc cctatgatgt gacagaagac tccattaagg aattctttag aggattaaat
361 atcagtgcag tgcgtttacc gcgtgaaccc agcaatcctg agaggttaaa agttttggt
421 tatgcagagt ttgaggacct ggattccttg ctcagtgcct tgagcctcaa cgaagagtct
481 ctaggtaaca ggagaattcg agtggacgtt gctgatcaag cacaggataa agacaggat
541 gatcgttctt ttggccgaga tagaaatcgt gattctgaca aaacagatac agactgagg
601 gcccgtcctg ctgcagacag ctttgatgac tacccgccca gaagggggtga tgatagcttt
661 ggagacaagt atcgagatcg ttacgattca gacagatatc gtgatgggta tcgggacagt
721 taccgtgatg gcccacgccg ggacatggat cgatacgggg gccgagatcg ctatgatgac
781 cgaggtggca gagactatga cagaggctac gattccagga taggcagtgg cagaagagca
841 ttcggtagcg ggtaccggag ggatgatgac tacagaggag gcggggaccg ctatgaagac
901 agatacgaca gacgagatga ccggtcctgg agttccagag atgattactc tcgggatgat
961 tacaggcggg atgatagagg tccccctcaa agacccaaac tgaacctaaa gcctcggagt
1021 actcctaagg aagatgattc ctccgctagc acctcccagt ccagtcgtgc agcctctatc
1081 ttttggagggg caaagcctgt tgacacagct gctagagaac gagaagtaga agagcggcta
1141 cagaaggaac aggagaaact gcagcgtcag ctggatgagc caaaactaga acgacggcct
1201 cgggagagac acccaagctg gcgaagtgaa gaaactcagg aacgggaacg atcgaggaca
1261 ggaagtgagt catcacagac tgggacctca gccacatctg gcagaaatgc aagaagaaga
1321 gagagtgaga agtctttaga aaatgaaacc cccaataaag aggaagactg tcagtctcca
1381 acttctaagc ctcccaaacc tgaacagcct ctaaaggtaa tgccagcccc tccaccaaag
1441 gagaatgctt gggtgaagcg aagttctaac cctcctgctc gatctcagag ctcagacaca
1501 gagcagcagt ccctacaag tggtggaggg aaagtagttc cagctcaact atctgaggaa
1561 ggatcagcaa ggaaagatga aaataaagta gatgggggtga gtgccccaaa aggccaaagt
1621 gggagctcca gccgtggtcc gggagatggg gggaacaaag accactggaa ggaggcagac
1681 aggaaaagatg gcaaaaagga tcacgactcc agatctgcac ctgagccaaa gaaagctgaa
1741 gaaaatccag cctcgaagtt cagatctgca agcaagtacg ctactctcgc cattgacggt
1801 gaagatgaaa atgagggaga ttacaccgaa tag (SEQ ID NO:27)
```

Cow eIF4B Amino Acid Sequence (NP_001030200.1)

```
  1 maasakkknk kgktisltdf laedggtggg styvpkpvsw adetddlegd vsttwhsndd
 61 dvyrappidr silptapraa repnidrsrl pksppytafl gnlpydvted sikeffrgln
121 isavrlprep snperlkgfg yaefedldsl lsalslnees lgnrrirvdv adqaqdkdrd
181 drsfgrdrnr dsdktdtdwr arpaadsfdd ypprrgddsf gdkyrdryds dryrdgyrds
241 yrdgprrdmd ryggrdrydd rggrdydrgy dsrigsgrra fgsgyrrddd yrgggdryed
301 rydrrdrsw ssrddysrdd yrrddrgppq rpklnlkprs tpkeddssas tsqssraasi
361 fggakpvdta arereveerl qkeqeklqrg ldepklerrp rerhpswrse etqerersrt
421 gsessqtgts atsgrnarrr eseksletlet pnkeedcqsp tskppkpeqp lkvmpapppk
481 enawvkrssn pparsqssdt eqqsptsggg kvvpaqlsee qsarkdenkv dgvsapkgqs
541 qsssrgpgdg gnkdhwkead rkdgkkdhds rsapepkkae enpaskfrsa skyatlaidg
601 edenegdyte (SEQ ID NO:28)
```

TABLE 1-continued

Rat eIF4B cDNA Sequence (NM_001008324.1)
```
   1 atggcggcct cagcaaaaaa gaagaataag aaggggaaga ccatctccct aacagacttt
  61 ctagctgagg atgggggaac tggtggagga agcacctatg tccccaaacc agtcagctgg
 121 gctgatgaaa cagacgatct ggaaggagat gtgtcaacaa cttggcatag taacgatgac
 181 gatgtgtaca gggcacctcc tattgaccgt tccatccttc ccactgctcc acgggctgct
 241 cgggaaccca atattgatcg agccgtctt cccaagtcac caccctacac tgctttccta
 301 gggaatctgc cctatgatgt gacagaagac tctattaagg atttctttag aggattaaat
 361 atcagcgctg tacgcttgcc gcgtgagccc agcaatccag acaggttgaa aggttttggc
 421 tatgccgaat ttgaggatct ggattctctg ctcagtgctc tgagtctcaa tgaagagtct
 481 ctaggtaaca ggagaattcg ggtggatgtt gctgatcaag cacaggataa agacagggat
 541 gaccgttctt ttggtcgaga tagaaatcgg gattctgaca agacagacac agactggagg
 601 gcccgtcctg ccacagacag cttttgatgac tacccaccta gacgaggtga tgacagcttc
 661 ggagacaagt atcgagatcg ttacgagtca gaccggtatc gggatgggta taggdacgga
 721 tatcgggacg gcccacgcag agacatggac cgctatgggg gccgggatcg ctatgatgac
 781 cgaggcagca gagactatga ccgaggctat gactccagga taggcagtgg cagaagagca
 841 ttttggaagtg ggtaccggag ggatgacgac tacagaggag gtggggaccg ctatgaagat
 901 cgctatgaca gacgggacga tcggtcatgg agctccaggg acgattactc tcgggacgat
 961 tacatggcgtg atgacagagg tccccccccaa agacccaaac tgaatctaaa gcctcggagt
1021 actcctaaag aagatgattc ctctgctagc acctccccagt ccagccgagc ggcttctatc
1081 ttttggagggg cgaagcctgt tgacacagct gctagagaaa gagaagtaga ggagcggcta
1141 cagaaggagc aggagaagct gcagcgtcag ctgatgagc caaaactaga ccgccggccc
1201 cgggagagac acccaagttg gcgaagtgaa gaaactcagg aaagagaacg gtcgaggaca
1261 ggaagtgagt catccgcagac tgggacctca gccacatctg gcagaaatac acgaaggaga
1321 gagagtgaga agtcctagata aaatgaaacc ctcaataaag aagaagactg tcactctcca
1381 acctccaagc ctcctaaacc tgaccagcct ctaaaggtaa tgccagcccc tccaccaaag
1441 gagaatgcgt gggtgaagcg aagctctaac cctcctgctc gatctcagag ctcagacaca
1501 gagcagccgt cccctacaag tggtggaggg aaagttgctc cagctcagcc ctctgaggaa
1561 ggaccatcaa ggaaagatga aactaaagtg gatggggtga gcaccaccaa aggccagact
1621 ggacactcca gccgtggtcc tggggatgga gggagcagag accactggaa ggagttggat
1681 aggaaggacg gcaaaaaaga tcaagactcc agatctgcac ctgagccaaa gaaatctgag
1741 gagaaccgag cctctaagtt cagttctgca agcaagtacg ctgctctgtc tgtggacggt
1801 gaggatgagg atgagggaga cgactgcact gagtag (SEQ ID NO:29)
```

Rat eIF4B Amino Acid Sequence (NP_001008325.1)
```
   1 maasakkknk kgktisltdf laedggtggg styvpkpvsw adetddlegd vsttwhsndd
  61 dvyrappidr silptapraa repnidrsrl pksppytafl gnlpydvted sikdfffrgln
 121 isavrlprep snpdrlkgfg yaefedldsl lsalslnees lgnrrirvdv adqaqdkdrd
 181 drsfgrdrnt dsdktdtdwr arpatdsfdd ypprrgddsf gdkyrdryes dryrdgyrdg
 241 yrdgprrdmd ryggrdrydd rgsrdydrgy dsrigsgrra fgsgyrrddd yrgggdryed
 301 rydrrddrsw ssrddysrdd yrrddrgppq rpklnlkprs tpkeddssas tsqssraasi
 361 fggakpvdta arereveerl qkeqeklqrq ldepkldrrp rerhpswrse etqerersrt
 421 qsessqtqts atsgrntrrr eseksllenet lnkeedchsp tskppkpdqp lkvmpapppk
 481 enawvkrssn pparsqssdt eqpsptsggg kvapaqpsee gpsrkdetkv dgvsttkgqt
 541 ghssrgpgdg gsrdhwkeld rkdgkkdqds rsapepkkse enraskfssa skyaalsvdg
 601 ededegddct e (SEQ ID NO:30)
```

Human Histone H3.1 Amino Acid Sequence (NP_003520.1)
```
   1 martkqtark stggkaprkq latkaarksa patggvkkph ryrpgtvalr eirryqkste
  61 llirklpfqr lvreiaqdfk tdlrfqssav malqeaceay lvglfedtnl caihakrvti
 121 mpkdiqlarr irgera (SEQ ID NO:31)
```

Mouse Histone H3.1 Amino Acid Sequence (NP_038578.2):
```
   1 martkqtark stggkaprkq latkaarksa patggvkkph ryrpgtvalr eirryqkste
  61 llirklpfqr lvreiaqdfk tdlrfqssav malqeaceay lvglfedtnl caihakrvti
 121 mpkdiqlarr irgera (SEQ ID NO:32)
```

Human Histone H3.2 Amino Acid Sequence (NP_001005464.1):
```
   1 martkqtark stggkaprkq latkaarksa patggvkkph ryrpgtvalr eirryqkste
  61 llirklpfqr lvreiaqdfk tdlrfqssav malqeaseay lvglfedtnl caihakrvti
 121 mpkdiqlarr irgea (SEQ ID NO:33)
```

Mouse Histone H3.2 Amino Acid Sequence (NP_835587.1):
```
   1 martkqtark stggkaprkq latkaarksa patggvkkph ryrpgtvalr eirryqkste
  61 llirklpfqr lvreiaqdfk tdlrfqssav malqeaseay lvglfedtnl caihakrvti
 121 mpkdiqlarr irgera (SEQ ID NO:34)
```

Human Histone H3.3 Amino Acid Sequence (NP_002098.1):
```
   1 martkqtark stggkaprkq latkaarksa pstggvkkph ryrpgtvalr eirryqkste
  61 llirklpfqr lvreiaqdfk tdlrfqsaai galqeaseay lvglfedtnl caihakrvti
 121 mpkdiqlarr irgera (SEQ ID NO:35)
```

Mouse Histone H3.3 Amino Acid Sequence (NP_032237.1):
```
   1 martkqtark stggkaprkq latkaarksa pstggvkkph ryrpgtvalr eirryqkste
  61 llirklpfqr pvreiaqdfk tdlrfqsaal galqeaseay lvglfedtnl caihakrvti
 121 mpkdiqlarr irgera (SEQ ID NO:36)
```

Nucleic acid and protein molecules (e.g., those of MELK, eIF4B, and orthologs thereof across species) that differ due to degeneracy of the genetic code or due to encoding or having "non-essential", "conservative", "stereoisomers", or "unconventional" amino acids that do not appreciably alter the enzymatic (e.g., kinase) and/or eIF4B Ser-406-regulatory ability of MELK are included within the scope of the invention. A "conservative amino acid substitution" is one in which the amino acid residue is replaced with an amino acid residue having a similar side chain. Stereoisomers (e.g., D-amino acids) of the twenty conventional amino acids, unnatural amino acids such as alpha,alpha-disubstituted amino acids, N-alkyl amino acids, lactic acid, and other unconventional amino acids may also be suitable components for polypeptides described herein. There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, CC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, G) | TGC, TGT |
| Gitamic acid (Glu, E) | GAA, GAG |
| Glutamine (Gln, Q) | CAA, CAG |
| Glycine (Gly, G) | GGA, CCC, CCC, GGT |
| Histidine (His, H) | CAC, CAT |
| Isoleucine (Ile, I) | ATA, ATC, ATT |
| Leucine (Leu, L) | GTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Theonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, CTG, GTT |
| Termination signal (end) | TAA, TAG, TGA |

An important and well known feature of the genetic code is its redundancy, whereby, for most of the amino acids used to make proteins, more than one coding nucleotide triplet may be employed (for example, illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid. In addition, a skilled artisan will understand how to mutate nucleotides of a specific codon so as to specifically alter an encoded amino acid based on the relevant codon chart. Additional desired nucleic acid and/or amino acid modifications can be engineered using site-directed mutagenesis and PCR-mediated mutagenesis techniques.

The "nucleic acid" can take any of a number of forms (e.g., DNA, mRNA, cDNA) that encode a biomarker described herein. For example, such biomarker nucleic acid molecules include DNA (e.g., genomic DNA and cDNA) comprising the entire or a partial sequence of a desired gene or the complement or hybridizing fragment of such a sequence. The biomarker nucleic acid molecules also include RNA comprising the entire or a partial sequence of a desired gene or the complement of such a sequence, wherein all thymidine residues are replaced with uridine residues. A "transcribed polynucleotide" is a polynucleotide (e.g., an RNA, a cDNA, or an analog of one of an RNA or cDNA) which is complementary to or homologous with all or a portion of a mature RNA made by transcription of a biomarker of the present invention, at least in part, and normal post-transcriptional processing (e.g., splicing), if any, of the transcript, and reverse transcription of the transcript.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantial homology" refers to homology of at least 50%, at least 60%, at least 65%, at least 70%, at least 75%, at least 80%, at least 85%, at least 90%, at least 95% or more (e.g., about 96%, 96.5%, 97%, 97.5%, 98%, 98.5%, 99%, 99.5%, 99.6%, 99.7%, 99.8%, 99.9% or more). In one embodiment, biomarker nucleic acid molecules encode a protein or portion thereof which includes an amino acid sequence which is sufficiently homologous to an amino acid sequence described herein such that the protein or portion thereof maintains, for example, the ability to phosphorylate eIF4B, to phosphorylate Histone H3, and/or the ability to be phosphorylated by MELK.

The comparison of sequences and determination of percent homology between two sequences can be accomplished using a mathematical algorithm. The alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5. Similarly, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

Methods for the production of nucleic acids (e.g., MELK, eIF4B, and/or mRNAs translated from nucleic acids having structured 5' regions are known in the art and include standard hybridization, PCR, and/or synthetic nucleic acid techniques. The nucleic acid so amplified can be cloned into an appropriate vector and characterized by DNA sequence analysis.

A "biomarker protein" is a protein encoded by or corresponding to a biomarker of the present invention. The terms "protein" and "polypeptide" are used interchangeably herein. In one embodiment, the protein is at least 50%, 60%, 70%, 80%, 90%, and 95% or more (e.g., 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or more) homologous to the entire amino acid sequence of a MELK and/or eIF4B and/or Histone H3 protein described herein. In addition, biologically active portions of MELK and/or eIF4B and/or Histone H3 proteins described herein are included which have at least 50%, 60%, 70%, 80%, 90%, and 95% or more (e.g., 95.5%, 96%, 96.5%, 97%, 97.5%, 98%, 98.5%, 99%, 99.1%, 99.4%, 99.5%, 99.6%, 99.7%, 99.8%, 99.9% or more) homology to a fragment of a MELK and/or eIF4B and/or Histone H3 protein described herein, e.g., a domain or motif, and that is capable of phosphorylating eIF4B, phosphorylating Histone H3, or being phosphorylated by MELK. Typically, biologically active portions (peptides, e.g., peptides which are, for example, 5, 10, 15, 20, 30, 35, 36, 37, 38, 39, 40, 50, 100, 150, 200, 250, 300, 350, 400, 450, or more amino acids in length) comprise a domain or motif, e.g., a MELK kinase domain, eIF4B domain encompassing an amino acid residue phosphorylatable by MELK such as a MELK-mediated phosphorylation substrate motif having an arginine at −3 amino acid residue positions relative to serine/threonine (e.g., Ser406 or Ser422 of human eIF4B), or Histone H3 domain encompassing an amino acid residue phosphorylatable by MELK such as a human Histone H3 region comprising Ser10. Moreover, other biologically active portions, in which other regions of the protein are deleted, can be prepared by recombinant techniques and evaluated for one or more of the activities described herein.

Methods for the production of proteins (e.g., MELK and/or eIF4B and/or Histone H3) are known in the art and include e.g., the expression of the protein in appropriate cells starting from a cDNA or the production by subsequent addition of amino acids to a starting amino acid (see Current Protocols, John Wiley & Sons, Inc., New York). Furthermore, methods for the production of protein fragments are known in the art and include the cleavage of the protein with appropriate proteases or the generation of nucleic acid fragments encoding the protein fragments and subsequent expression of the fragments in appropriate cells. Methods for the production of mutated proteins, e.g., by exchanging and/or deleting one or more amino acids, are known in the art.

B. Diagnostic Methods

Methods are provided for identifying agents, such as small molecules and antibodies, which inhibit oncogenic and/or kinase activity of human MELK or an ortholog thereof, comprising: a) contacting a sample comprising i) human MELK or an ortholog thereof and ii) human eukaryotic initiation factor 4B (eIF4B) or an ortholog thereof, with the agent; and b) determining the ability of the agent to inhibit Ser-406 phosphorylation of human eIF4B or a corresponding phosphorylatable amino acid in the ortholog of human eIF4B, wherein decreased phosphorylation identifies an agent which inhibits kinase or oncogenic activity of human MELK or the ortholog thereof. Similarly, methods are provided for identifying agents, such as small molecules and antibodies, which inhibit oncogenic and/or kinase activity of human MELK or an ortholog thereof, comprising: a) contacting a sample comprising i) human MELK or an ortholog thereof and ii) human Histone H3 or an ortholog thereof, with the agent; and b) determining the ability of the agent to inhibit Thr-3 phosphorylation and/or Ser-10 phosphorylation and/or Thr-11 phosphorylation of human Histone H3, or a corresponding phosphorylatable amino acid in the ortholog of human Histone H3, wherein decreased phosphorylation identifies an agent which inhibits kinase or oncogenic activity of human MELK or the ortholog thereof. These methods are also referred to herein as drug screening assays and typically include the step of screening a candidate/test compound or agent for the ability to interact with (e.g., bind to) a MELK and/or eIF4B and/or Histone H3 protein, to modulate the phosphorylation of eIF4B by MELK, to modulate the interaction of a phosphorylatable residue of eIF4B with a MELK-mediated intracellular signaling target, to modulate the phosphorylation of Histone H3 by MELK, and/or to modulate the interaction of a phosphorylatable residue of Histone H3 with a MELK-mediated intracellular signaling target. Test compounds or agents which have one or more of these abilities can be used as drugs to treat disorders characterized by aberrant, abnormal, and/or unwanted MELK and/or eIF4B and/or Histone H3 nucleic acid expression and/or protein activity, such as cancer. Candidate/test compounds include, for example, small organic and inorganic molecules (e.g., molecules obtained from combinatorial and natural product libraries). Similarly, antibody agents that, for example bind to MELK in a manner that modulates phosphorylation of a residue by MELK, modulates eIF4B activity normally driven by MELK-mediated phosphorylation, and/or modulates Histone H3 activity normally driven by MELK-mediated phosphorylation, can be useful agents. The skilled artisan can also readily make other modulatory agents, such as aptamers, antisense RNA, siRNA, that are capable of interacting with MELK nucleic acids and/or proteins to affect MELK-mediated phosphorylation of eIF4B or Histone H3 (see, at least Chung et al. (2012) 3:1629-1640; WO 2013/109388; WO 2012/016082; WO 2013/045539: each of which is incorporated herein in its entirety by this reference.

The term "sample," "tissue sample," "subject sample," "subject cell or tissue sample" or "specimen" each refer to a collection of similar cells obtained from a tissue of a subject or subject either as in vitro (e.g., cultured), ex vivo, or in vivo (e.g., isolated primary cells) samples. The source of the tissue sample may be solid tissue as from a fresh, frozen and/or preserved organ, tissue sample, biopsy, or aspirate, blood or any blood constituents, bodily fluids such as whole blood, serum, plasma, buccal scrape, saliva, cerebrospinal fluid, urine, stool, and bone marrow, amniotic fluid, peritoneal fluid or interstitial fluid; or cells from any time in gestation or development of the subject. The tissue sample may contain compounds that are not naturally intermixed with the tissue in nature such as preservatives, anticoagulants, buffers, fixatives, nutrients, antibiotics or the like. The sample may further comprise cancer cells, such as ovarian, lung, breast, and multiple myeloma cancer cells or any cancer in which MELK and/or eIF4B and/or Histone H3 is amplified or overexpressed, has an activating mutation, or is activated by other kinases.

The terms "subject" and "patient" are used interchangeably. As used herein, the terms "subject" and "subjects" refer to an animal, e.g., a mammal including a non-primate (e.g., a cow, pig, horse, donkey, goat, camel, cat, dog, guinea pig, rat, mouse, sheep) and a primate (e.g., a monkey, such as a cynomolgous monkey, gorilla, chimpanzee and a human).

The term "inhibit" refers to a statistically significant decrease in a metric of interest, such as the reduction of Thr-3 phosphorylated and/or Ser-10-phosphorylated and/or Thr-11-phosphorylated Histone H3, Ser-406-phosphorylated eIF4B, MELK enzymatic activity (e.g., kinase activity), cancer progression, and the like. Such statistically significant decrease can be at least 10%, 20%, 30%, 40%, 50%, 60%, 70%, 80%, 90%, or more relative to a control. For example, a test compound administered and analyzed according to the methods described herein can comprise a bona fide inhibitor of MELK enzymatic activity (e.g., kinase activity) by decreasing Ser-406-phosphorylated eIF4B amounts, Thr-3 phosphorylated Histone H3 amounts, Ser-10-phosphorylated Histone H3 amounts, and/or Thr-11-phosphorylated Histone H3 amounts by at least 10%, 20%, 30%, 40%, 50%, 60%, 70%, 80%, 90% or more relative to that of no MELK ligand administration or over a given amount of time. In one embodiment, the term "MELK inhibitor" is a substance, such as a small molecule, antibody, antisense nucleic acid, small interfering nucleic acid, which interferes with the phosphorylation of human eIF-4B Ser-406 or at a corresponding phosphorylation site in an eIF-4B ortholog thereof the phosphorylation of human Histone H3 at Thr-3 or at a corresponding phosphorylation site in a Histone ortholog thereof, the phosphorylation of human Histone H3 at Ser-10 or at a corresponding phosphorylation site in a Histone H3 ortholog thereof and/or the phosphorylation of human Histone H3 at Thr-11 or at a corresponding phosphorylation site in a Histone H3 ortholog thereof. Exemplary MELK inhibitors are well known in the art, such as OTSSP167, siomycin A, thiostrepton, and anti-MELK antibodies are disclosed, for example, in Chung et al. (2012) Oncotarget 3:1629-1640; WO 2013/045539; WO 2013/109388; and WO 2012/016082; each of which is incorporated in its entirety herein by this reference.

The term "altered amount" of a biomarker or "altered level" of a biomarker refers to increased or decreased expression, modification, and/or activity of a biomarker of the present invention, at least in part in a sample as compared to that in a control sample.

The amount of a biomarker in a subject is "significantly" higher or lower than the normal amount of a biomarker, if the amount of the biomarker is greater or less, respectively, than the normal level by an amount greater than the standard error of the assay employed to assess amount, or at least two, three, four, five, ten or more times that amount. Alternatively, the amount of the biomarker in the subject can be considered "significantly" higher or lower than the normal amount if the amount is at least about two, at least about three, at least about four, or at least about five times, higher or lower, respectively, than the normal amount of the biomarker (e.g., in a control sample or the average expression level of the biomarkers of the present invention in several control samples).

"Likely to," as used herein, refers to an increased probability, that an item, object, thing or person will occur such as at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, or more (or any range inclusive). Thus, in one embodiment, an agent that is likely to inhibit MELK-mediated phosphorylation of eIF4B has an increased probability of inhibiting Ser-406 phosphorylation of human eIF4B or a corresponding phosphorylatable amino acid in an ortholog of human eIF4B. In another embodiment, an agent that is likely to inhibit MELK-mediated phosphorylation of Histone H3 has an increased probability of inhibiting Thr-3 phosphorylation, Ser-10 phosphorylation, and/or Thr-11 phosphorylation of human Histone H3, or a corresponding phosphorylatable amino acid in an ortholog of human Histone H3.

Test compounds of the present invention, at least in part, can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 19:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91; 11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390): (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, the inhibition of Ser-406 phosphorylation of human eIF4B or a corresponding phosphorylatable amino acid in an ortholog of human eIF4B is determined by comparing the amount of Ser-406 phosphorylated human eIF4B or a corresponding phosphorylatable amino acid in the ortholog of human eIF4B, in the sample relative to a control. The control can be the amount of amount of Ser-406 phosphorylated human eIF4B or a corresponding phosphorylatable amino acid in the ortholog of human eIF4B in the sample relative to said amount in the absence of the agent or at an earlier timepoint after contact of the sample with the agent. The phosphorylation level of eIF4B is generally determined by measuring the amount of phosphorylated eIF4B protein and, optionally, of unphosphorylated eIF4B, and normalizing the amount of phosphorylated protein to the total protein in the sample being analyzed. The calculated response phosphorylation level in the presence of the test compound and the basal or background phosphorylation levels (e.g., in the absence of the test compound or at a earlier timepoint after test compound administration) are thus not affected by differences in the absolute quantity of the indicator protein at a given time.

The discriminatory time point, or predetermined time after administering the test compound to cells, can be selected to achieve a calibrated statistically significant difference between Ser-406 phosphorylation levels in the sample relative to controls. The difference may be maximal at the predetermined time but that is not required and depends on other parameters of the test. In addition, whereas the calculation of ratios as described herein is beneficial in providing useful comparative numbers, calculation of absolute differences between phosphorylated eIF4B levels upon administration of test compounds relative to controls, and between test subjects and control subjects, could also be employed and would be effective.

In some embodiments, the methods described above can further comprise determining the amount of determining the amount of a protein translated from an mRNA with highly structured 5' untranslated region (5'UTR), optionally wherein the protein is selected from the group consisting of cellular myelocytomatosis oncogene (c-Myc), X-linked inhibitor of apoptosis protein (XIAP), and ornithine decarboxylase (ODC1). It is known that eIF4B stimulates the helicase activity of eIF4A for unwinding the secondary structure of 5'UTR of mRNA and that eIF4B is important for the translation of mRNA with structured 5'UTR (Dmitriev et al. (2003) *Mol. Cell Biol.* 23:8925-8933 and Shahbazian et al. (2010) *Mol. Cell Biol.* 30 1478-1485). The skilled artisan is well aware of mRNA with structured 5'UTR encoding oncogenic proteins, such as c-Myc, XIAP (X-linked inhibitor of apoptosis protein), ODC (ornithine decarboxylase), VEGF, HIF-1alpha, and the like (see, at least Bert et al. (2006) *RNA* 12:1074-1083).

Phosphorylation is a biochemical reaction in which a phosphate group is added to Ser, Thr or Tyr residues of a protein and is catalyzed by protein kinase enzymes. Phosphorylation normally modifies the functions of target proteins, often causing activation. As part of the cell's homeostatic mechanisms, phosphorylation is only a transient process that is reversed by other enzyme called phosphatases. Therefore, protein phosphorylation levels change over time and can be evaluated in a number of well-known manners, including, for example, by immunological approaches. For example, the amount of Ser-406 phosphorylated human eIF4B or a corresponding phosphorylatable amino acid in ortholog of human eIF4B is determined by an immunoassay using a reagent which specifically binds with Ser-406 phosphorylated human eIF4B or corresponding phosphorylated ortholog of human eIF4B. Such an immunoassay comprise a number of well known forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with NMR, MALDI-TOF, LC-MS/MS, are known to those of ordinary skill in the art.

In one embodiment, the enzyme immunoassay is a sandwich enzyme immunoassay using a capture antibody or fragment thereof which specifically binds with human eIF4B or corresponding ortholog of human eIF4B and a detection antibody or fragment thereof which specifically binds with Ser-406 phosphorylated human eIF4B or a corresponding phosphorylated ortholog of human eIF4B. Such an enzyme immunoassay is particularly advantageous because identifying differences in protein levels between related kinase family members or isoforms given the relatively high homology between kinases among themselves and also among their phosphorylated forms.

Immunological reagents for identifying eIF4B in both phosphorylated and non-phosphorylated forms, as well as for detecting MELK, are well known in the art and can be generated using standard techniques, such as by inoculating host animals with appropriate eIF4B phosphor-peptides. Such anti-MELK, anti-eIF4B, and/or anti-phospho-eIF4B antibody reagents (e.g., monoclonal antibody) can be used to isolate and/or determine the amount of the respective proteins such as in a cellular lysate. Such reagents can also be used to monitor protein levels in a cell or tissue, e.g., white blood cells or lymphocytes, as part of a clinical testing procedure, e.g., in order to monitor an optimal dosage of an inhibitory agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}I$; $^{131}I$, $^{35}S$ or $^{3}H$.

The screening assays described above can further be adapted to identify candidate/test compounds which modulate (e.g., stimulate or inhibit) the interaction (and most likely MELK and eIF4B oncogenic activity as well) between an eIF4B protein and a target eIF4B protein with which the eIF4B protein normally interacts or modulates to verify that MELK-mediated enzymatic activity has been reduced in accordance with the reduced amounts of phosphorylated eIF4B levels. Examples of such target molecules or substrates include certain protein encoded by mRNA with structured 5'UTR, such as those described further herein.

As described above for the identification of eIF4B phosphorylation, Thr-3 phosphorylation, Ser-10 phosphorylation, and/or Thr-11 phosphorylation of human Histone H3, or a corresponding phosphorylatable amino acid in an ortholog of human Histone H3, and modulation (e.g., inhibition) thereof, can similarly be determined.

In another embodiment, the invention provides assays for screening candidate/test compounds which interact with (e.g., bind to) MELK and/or eIF4B and/or Histone H3 protein. "Binding compound" shall refer to a binding composition, such as a small molecule, an antibody, a peptide, a peptide or non-peptide ligand, a protein, an oligonucleotide, an oligonucleotide analog, such as a peptide nucleic acid, a lectin, or any other molecular entity that is capable of specifically binding to a target protein or molecule or stable complex formation with an analyte of interest, such as a complex of proteins. "Binding moiety" means any molecule to which molecular tags can be directly or indirectly attached that is capable of specifically binding to an analyte. Binding moieties include, but are not limited to, antibodies, antibody binding compositions, peptides, proteins, nucleic acids and organic molecules having a molecular weight of up to about 1000 daltons and containing atoms selected from the group consisting of hydrogen, fluoride, carbon, oxygen, nitrogen, sulfur and phosphorus. Typically, the assays are cell-based assays. The cell, for example, can be of mammalian origin expressing MELK and/or eIF4B and/or Histone H3, e.g., a cancer cell.

In other embodiments, the assays are cell-free assays which include the steps of combining a MELK and/or eIF4B and/or Histone H3 protein or a biologically active portion thereof, and a candidate/test compound, e.g., under conditions which allow for interaction of (e.g., binding of) the candidate/test compound to the MELK and/or eIF4B and/or Histone H3 protein or biologically active portion thereof to form a complex, and detecting the formation of a complex, in which the ability of the candidate compound to interact with (e.g., bind to) the MELK and/or eIF4B and/or Histone H3 polypeptide or biologically active fragment thereof is indicated by the presence of the candidate compound in the complex. Formation of complexes between the MELK and/or eIF4B and/or Histone H3 protein and the candidate compound can be quantitated, for example, using standard immunoassays. Such analyses would identify test compounds as MELK and/or eIF4B and/or Histone H3 ligands.

To perform the above drug screening assays, it can be desirable to immobilize either MELK and/or eIF4B and/or Histone H3 or its target molecule to facilitate separation of complexes from uncomplexed forms of one or both of the proteins, as well as to accommodate automation of the assay. Interaction (e.g., binding of) MELK and/or eIF4B and/or Histone H3 to a target molecule, in the presence and absence of a candidate compound, can be accomplished in any vessel suitable for containing the reactants. Examples of such vessels include microtitre plates, test tubes, and microcentrifuge tubes. In one embodiment, a fusion polypeptide can be provided which adds a domain that allows the polypeptide to be bound to a matrix. For example, glutathione-S-transferase-MELK, -Histone H3, and/or -eIF4B fusion polypeptides can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of MELK-, Histone H3-, and/or eIF4B-binding polypeptide found in the bead fraction quantitated from the gel using standard electrophoretic techniques.

Other techniques for immobilizing polypeptides on matrices can also be used in the exemplary drug screening assays of the invention. For example, MELK and/or eIF4B and/or Histone H3 or its target molecule can be immobilized utilizing conjugation of biotin and streptavidin. Biotinylated MELK and/or eIF4B and/or Histone H3 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with MELK and/or eIF4B and/or Histone H3, but which do not interfere with binding of the polypeptide to its target molecule can be derivatized to the wells of the plate, and MELK and/or eIF4B and/or Histone H3 trapped in the wells by antibody conjugation. As described above, preparations of a MELK- and/or eIF4B-binding polypeptide and a candidate compound are incubated in the MELK- and/or eIF4B- and/or Histone H3-presenting wells of the plate, and the amount of complex trapped in the well can be quantitated. Methods for detecting such complexes, in addition to those described above for the GST-immobilized complexes, include immunodetection of complexes using antibodies reactive with the MELK and/or eIF4B and/or Histone H3 target molecule, or which are reactive with MELK and/or eIF4B and/or Histone H3 polypeptide and compete with the target molecule; as well as enzyme-linked assays which rely on detecting an enzymatic activity associated with the target molecule.

In another aspect, a method for assessing the efficacy of an agent for inhibiting kinase activity of human MELK or an ortholog thereof in a subject, comprising: a) detecting in a subject sample at a first point in time, the amount of Ser-406 phosphorylated human eIF4B or the amount of a human eIF4B ortholog phosphorylated at a corresponding amino acid of human eIF4B; b) repeating step a) during at one or more subsequent points in time after administration of the agent; and c) comparing the amount of phosphorylated human eIF-4B ortholog thereof detected in step a) with said amount detected in step b), wherein a higher amount of Ser-406 phosphorylated human eIF4B or the amount of the human eIF4B ortholog phosphorylated at a corresponding amino acid of human eIF4B in the first point in time relative to at least one subsequent point in time, indicates that the agent inhibits kinase activity of MELK or the ortholog thereof, is provided. Similarly, a method for assessing the efficacy of an agent for inhibiting kinase activity of human MELK or an ortholog thereof in a subject, comprising: a) detecting in a subject sample at a first point in time, the amount of Thr-3 phosphorylated, Ser-10 phosphorylated, and/or Thr-11 phosphorylated human Histone H3, or the amount of a human Histone H3 ortholog phosphorylated at a corresponding amino acid of human Histone H3; b) repeating step a) during at one or more subsequent points in time after administration of the agent; and c) comparing the amount of phosphorylated human Histone H3 or ortholog thereof detected in step a) with said amount detected in step b), wherein a higher amount of Thr-3 phosphorylated, Ser-10 phosphorylated, and/or Thr-11, phosphorylated human Histone H3, or the amount of the human Histone H3 ortholog phosphorylated at a corresponding amino acid of human Histone H3 in the first point in time relative to at least one subsequent point in time, indicates that the agent inhibits kinase activity of MELK or the ortholog thereof, is provided.

As used herein, "time course" shall refer to the amount of time between an initial event and a subsequent event. For example, with respect to a subject's cancer progression, time course may relate to a subject's disease and may be measured by gauging significant events in the course of the disease, wherein the first event may be diagnosis and the subsequent event may be proliferation, metastasis, etc.

Once binding is confirmed, additional assays, such as kinase assays to determine inhibition of phosphorylation effects, can be performed according to well-known methods in the art. For example, assays for determining MELK kinase activity are well known in the art (see, for example, the publications described herein and incorporated by reference in their entirety). Briefly, MELK can be incubated with a suitable substrate in a buffer allowing phosphorylation of eIF4B or Histone H3. Phosphorylation of the substrate can be detected using a labeled phosphate group, such as the use of the radioactive label $^{32}P$ present as the ATP source in the buffer. Alternatively, antibodies specific for the phosphorylated products of eIF4B catalytic activity can be used to detect activity. As will be apparent to those of ordinary skill in the art, the assays are easily amenable to high through-put technologies using robotics and automated processes. Alternatively, the MELK kinase activity can be assayed using a synthetic substrate, such as a peptide library. MELK activity can also be assayed by detecting downstream targets of the kinase such as those described herein.

Ser-406-phosphorylated eIF4B can be analyzed according to any of the methods and using any of the samples described herein (e.g., single subject samples or pooled subject samples). Candidate compounds which produce a statistically significant change in phosphorylated-eIF4B-dependent responses (e.g., inhibition of human eIF4B phosphorylation at Ser-406 or a corresponding phosphorylatable amino acid residue in an eIF4B ortholog thereof) can be identified. Such statistically significant changes can be measured according to a number of criteria and/or relative to a number of controls. For example, significant modulation of phosphorylation Ser-406 can be assessed if the output under analysis is inhibited by 1.1-, 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-, 3.4-, 3.5-, 3.6-, 3.7-, 3.8-, 3.9-, 4.0-, 4.1-, 4.2-, 4.3-, 4.4-, 4.5-, 4.6-, 4.7-, 4.8-, 4.9-, 5.0-, 5.5-, 6.0, 6.5-, 7.0-, 7.5-, 8.0-, 8.5-, 9.0-9.5-, 10-, 11-, 12-, 13-, 14-, 15-, 16-, 17-, 18-, 19-, 20-fold or more different (including any range inclusive), relative to a control. In one embodiment, between the first point in time and the subsequent point in time, the subject has undergone treatment for cancer, has completed treatment for cancer, and/or is in remission from cancer.

As described above for the identification and/or analysis of eIF4B phosphorylation, Thr-3 phosphorylated, Ser-10 phosphorylated, and/or Thr-11 phosphorylated Histone H3, or a corresponding phosphorylatable amino acid in an ortholog of human Histone H3, and modulation (e.g., inhibition) thereof, can similarly be identified and/or analyzed.

The term "cancer" refers to the presence of cells possessing characteristics typical of cancer-causing cells, such as uncontrolled proliferation, immortality, metastatic potential, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Also included are any cancers in which the gene encoding MELK, and/or eIF4B and/or Histone H3 is amplified or overexpressed, or has an activating mutation, or the MELK and/or eIF4B and/or Histone H3 is hyper-activated by other kinases. In some embodiments, ovarian cancers, including serous cystadenocarcinoma, head and neck cancers, including non-small cell lung cancer (NSCLC), squamous cell carcinoma, pancreatic cancer, colon cancer, prostate cancer, and/or gliomas can be preferred.

"Treat," "treatment," and other forms of this word refer to the administration of an agent that inhibits the ability of 1) MELK to phosphorylate eIF4B and/or Histone H3 and/or 2) the ability of eIF4B or Histone H3 to be phosphorylated by MELK, to cause a cancer to be ameliorated, to extend the expected survival time of the subject and/or time to progression of a cancer or the like.

"Responsiveness," to "respond" to treatment, and other forms of this verb, as used herein, refer to the reaction of a subject to treatment with an agent capable of inhibiting the ability of 1) MELK to phosphorylate eIF4B or Histone H3 and/or 2) the ability of eIF4B or Histone H3 to be phosphorylated by MELK. As an example, a subject responds to treatment of the subject cell thereof with an agent if the assayed condition is modulated by at least 10%, 20%, 30%, 40%, 50%, 60%, 70%, 80%, 90% or more relative to that of no administration of the agent or over a given amount of time.

C. Treatment Methods

MELK and/or eIF4B and/or Histone H3 inhibitors described herein can be used to treat cancer. In one embodiment, a method of treating a subject afflicted with cancer comprising administering to the subject an agent that inhibits Ser-406 phosphorylation of human eIF4B or a corresponding phosphorylatable amino acid in an ortholog of human eIF4B, for example an agent that specifically modulates Ser-406 phosphorylation, thereby treating the subject afflicted with the cancer. In another embodiment, such MELK and/or eIF4B and/or Histone H3 inhibitors can also be used to determine the efficacy, toxicity, or side effects of treatment with such an agent. These methods of treatment generally include the steps of administering modulators in a pharmaceutical composition, as described further below, to a subject in need of such treatment, e.g., a subject with cancer or at risk for developing cancer.

The term "administering" is intended to include routes of administration which allow the agent to perform its intended function of inhibiting the ability of MELK to phosphorylate eIF4B, the ability of eIF4B to be phosphorylated by MELK, the ability of MELK to phosphorylate Histone H3, and/or the ability of Histone H3 to be phosphorylated by MELK. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "effective amount" of an agent inhibiting the ability of MELK to phosphorylate eIF4B and/or the ability of eIF4B to be phosphorylated by MELK is that amount necessary or sufficient to inhibit the ability of MELK to phosphorylate eIF4B and/or the ability of eIF4B to be phosphorylated by MELK in the subject or population of subjects is measured, for example, by the levels of Ser-406-phosphorylated human eIF4B or a corresponding phosphorylatable residue in an eIF4B ortholog thereof according to the methods described above. The same analysis applies to inhibiting the ability of MELK to phosphorylate Histone H3 and/or the ability of Histone H3 to be phosphorylated by MELK. The effective amount can vary depending on such factors as the type of therapeutic agent(s) employed, the size of the subject, or the severity of the disorder.

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to: the pharmacodynamic characteristics of the particular agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages that are less than the effective dose of the compound. Thereafter, in one embodiment, the dosage should be increased by small increments until the optimum effect under the circumstances is reached. For convenience, the total daily dosage may be divided and administered in portions during the day if desired.

The effectiveness of any particular agent to treat cancers can be monitored by comparing two or more samples obtained from subjects undergoing cancer treatment. In general, a first sample is obtained from the subject prior to beginning therapy and one or more samples during treatment. In such a use, a baseline of expression of cells from subjects with cancer prior to therapy is determined and then changes in the baseline state of expression of cells from subjects with cancer is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with metabolic disorders is increasing or decreasing.

MELK and/or eIF4B and/or Histone H3 inhibitors can be administered in pharmaceutically acceptable compositions which comprise a therapeutically-effective amount of the inhibitor formulated together with one or more pharmaceutically acceptable carriers (additives) and/or diluents. For example, formulations can be adapted for (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin, buccal, or sublingual surfaces; (4) intravaginally or intrarectally, for example, as a pessary, cream or foam; or (5) nasal/aerosol, for example, as an aqueous aerosol, liposomal preparation or solid particles containing the compound, based on well-known methods in the pharmaceutical arts.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate: (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that reduce the phosphorylation levels of PKC-iota and/or activity encompassed by the invention. These salts can be prepared in situ during the final isolation and purification of the agents, or by separately reacting a purified agents agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In addition, the methods described herein can further comprise treating subjects with MELK and/or eIF4B and/or Histone H3 inhibitors in addition to administering one or more additional anti-cancer agents and/or use samples from subjects exposed to such anti-cancer agents. Anti-cancer agents are well known to the skilled artisan and include, without limitation, chemotherapy and radiation, as well as immunotherapy, hormone therapy, and gene therapy using nucleic acid molecules and/or proteins that are linked to the initiation, progression, and/or pathology of a tumor or cancer.

Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs; mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen), benzamide (U.S. Pat. Re. 36,397); and NU1025 (Bowman et al.). In still another embodiment, the chemotherapeutic agents are platinum compounds, such as cisplatin, carboplatin, oxaliplatin, nedaplatin, and iproplatin. Other antineoplastic platinum coordination compounds are well known in the art, can be modified according to well-known methods in the art, and include the compounds disclosed in U.S. Pat. Nos. 4,996, 337, 4,946,954, 5,091,521, 5,434,256, 5,527,905, and 5,633, 243, all of which are incorporated herein by reference. The foregoing examples of chemotherapeutic agents are illustrative, and are not intended to be limiting.

Radiation therapy can also comprise an additional anti-cancer agent. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, Pd-103, Ir-192), intravenous administration of radioisotopes such as strontium-89, thoracic radiation therapy, intraperitoneal $^{32}$P radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

Additional anti-cancer agents include immunotherapy, hormone therapy, and gene therapy. Such therapies include, but are not limited to, the use of antisense polynucleotides, ribozymes, RNA interference molecules, triple helix polynucleotides and the like, where the nucleotide sequence of such compounds are related to the nucleotide sequences of DNA and/or RNA of genes that are linked to the initiation, progression, and/or pathology of a tumor or cancer. For example, oncogenes, growth factor genes, growth factor receptor genes, cell cycle genes, DNA repair genes, and others, may be targeted in such therapies.

Immunotherapy may comprise, for example, use of cancer vaccines and/or sensitized antigen presenting cells. Immunotherapy can also involve derepression of immunoinhibitory pathways, such as by targeting PD-L1, PD-L2, PD-1, CTLA-4, and the like. The immunotherapy can involve passive immunity for short-term protection of a host, achieved by the administration of an antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs, antigestagens (e.g., mifepristone, onapristone), or antiandrogens (e.g., cyproterone acetate).

In one embodiment, anti-cancer therapy used for cancers whose phenotype is determined by the methods of the invention can comprise one or more types of therapies described herein including, but not limited to, chemotherapeutic agents, immunotherapeutics, anti-angiogenic agents, cytokines, hormones, antibodies, polynucleotides, radiation and photodynamic therapeutic agents. For example, combination therapies can comprise one or more chemotherapeutic agents and radiation, one or more chemotherapeutic agents and immunotherapy, or one or more chemotherapeutic agents, radiation and chemotherapy.

EXEMPLIFICATION

This invention is further illustrated by the following examples, which should not be construed as limiting.

Example 1: Materials and Methods for Examples 2-3 a. Plasmids

Human eIF4B was cloned from the reverse transcription products of total RNA extracted from human mammary epithelial cells (HMECs), using the primers (forward: ATG-GCGGCCTCAGCAAAAAAG (SEQ ID NO:37); reverse: CTATTCGGCATAATCTTCTC (SEQ ID NO:38)). The 1.8 kb PCR product was then used as template for amplifying Flag-tagged or HA-tagged eIF4B with restriction sites. The constructs (pWzl-Flag-eIF4B, pTrex-eIF4B-HA) were verified by sequencing. Site-directed mutagenesis of eIF4B was performed using QuickChange XL (Stratagene), and all mutant constructs were confirmed by sequencing.

To generate pLKO-tet-on shRNA targeting human eIF4B, synthesized oligonucleotides were annealed and ligated with digested pLKO vector. The sequences for scramble, sh-eIF4B-1, sh-eIF4B-2 are GTGGACTCTTGAAAGTAC-TAT (SEQ ID NO:39), GGACCAGGAAGGAAAGATGAA (SEQ ID NO:40), and GCGGAGAAACACCTTGATCTT (SEQ ID NO:41), respectively.

b. Retroviral and Lentiviral Gene Delivery

Retroviruses were generated by transfecting HEK293T cells with retroviral plasmids and packaging DNA. Generally, 1.6 µg pWzl DNA, 1.2 µg pCG-VSVG and 1.2 µg pCG-gap/pol, 12 ul lipid of Metafectene Pro (Biontex) were used. DNA and lipid were diluted in 300 µl PBS respectively and mixed. After 15 minutes (min.) of incubation, they were added to one 6-cm dish that was seeded with 3 million HEK293T cells one day earlier. Viral supernatant was collected 48 hours (h) and 72 hours post-transfection. The supernatant was filtered through 0.45 µm membrane, and was added to target cells in the presence of 8 µg/ml polybrene (Millipore). Lentiviruses were generated with a similar approach with the exception of HEK293T cells that were transfected with 2 µg pLKO DNA, 1.5 µg pCMV-dR8.91, and 0.5 µg pMD2-VSVG. Cells were selected with antibiotics starting 72 h after initial infection. Puromycin and blasticidin were used at the final concentration s of 1.5 µg/ml and 4 µg/ml respectively.

c. Immunoblotting

For treatment with nocodazole, cells were refreshed with medium containing nocodazole (200 ng/ml). Twenty hours after treatment, floating mitotic cells were harvested by gental shake-off. For drug treatment, cells were seeded in multi-well plate, in the presence of OTSSP167 (ChemExpress, HY15512; 10 mM stock made in DMSO).

Cells were harvested and lysed with RIPA buffer (25 mM Tris, pH 7.4, 150 mM NaCl, 1% Nonidet P-40, 0.5% sodium deoxycholate, and 0.1% sodium dodecyl sulfate) supplemented with protease inhibitors cocktail (Roche) and phosphatase inhibitors cocktail (Thermo Scientific). Cleared lysates were analyzed for protein concentration using a BCA kit (Thermo Scientific). Equal amount of protein (10-20 µg) was resolved on SDS-PAGE, and was subsequently transferred onto a nitrocellulose or polyvinylidene difluoride membrane (Amersham). The membrane was blocked with 5% non-fat milk and was then incubated with primary antibodies overnight at 4° C. After washing, the membrane was incubated with fluorophore-conjugated secondary antibodies for 1 h at room temperature. The membrane was then washed and scanned with an Odyssey® Infrared scanner (Li-Cor Biosciences).

The following antibodies were used for immunoblotting or immunoprecipitation, MELK (Epitomics, 2916), p-eIF4B (S406) (Cell Signaling, 8151), p-eIF4B (S422) (Cell Signaling, 3591), eIF4B (Cell Signaling, 3592), c-Myc (Cell Signaling, 5605), XIAP (Cell Signaling, 2045), p-Akt (S473) (Cell Signaling, 4060), p-MAPK (T202/Y204) (Cell Signaling, 4370), cleaved PARP (Asp214) (Cell Signaling, 9541), Aurora A (Cell Signaling, 4718), Aurora B (Cell Signaling, 3094), p-Aurora A (T288)/Aurora B (T232)/Aurora C (T198) (Cell Signaling, 2914), p-Histone H3 (T3) (Cell Signaling, 13576), p-Histone H3 (S10) (Cell Signaling, 3377), p-Histone H3 (T11) (Cell Signaling, 9767), p-Histone H3 (S28) (Cell Signaling, 9713), ODC (Sigma, O1136), Vinculin (Sigma, V9131), alpha-tubulin (Sigma, T9016), anti-HA magnetic beads (Pierce, 88836), anti-Flag magnetic beads (Sigma, M8823). Secondary antibodies used were Alexa Fluor 680 goat anti-rabbit IgG (Invitrogen A-21109) and IRDye800-conjugated anti-mouse IgG (Rockland).

d. In Vitro Kinase Assay

Flag-tagged eIF4B or Flag-eIF4B (S406A) was transfected into HEK293T cells (4 µg DNA for cells in one 60 mm dish). Thirty-six hours after transfection, cells were lysed with IP buffer (100 mM NaCl, 50 mM Tris, pH 7.5, 0.5% NP-40, 0.5% Sodium deoxycholate, supplemented with protease/phosphatase inhibitor cocktail). Lysates were cleared via incubating with anti-mouse IgG conjugated to magnetic beads (4° C., 30 min), and then immunoprecipitated with anti-Flag M2 magnetic beads (Sigma) (4° C., 120 min). The beads with bound antigens were washed 5 times with IP buffer. Beads during the last wash were aliquoted into 1.5 ml microcentrifuge tubes. After removal of IP buffer, the beads were washed once with 1× kinase buffer without ATP (5 mM Tris, pH 7.5, 5 mM-βglycerophosphate, 2 mM dithiothreitol, 0.1 mM Na3VO4, 10 mM MgCl2; Cell Signaling). After the wash, 40 µl 1× kinase buffer with 200 mM ATP was added to each tube, followed by 5 ul buffer without or with 500 ng recombinant MELK. The reaction was incubated at 30° C. for 30 min, and terminated by adding 40 ul 2×SDS sample buffer. The samples were then boiled and subjected to immunoblotting. In vitro kinase assays with Histone H3 were performed as above, except that recombinant Histon H3.1 (New England BioLabs, M2503S) was used (50 ng per reaction).

e. Positional Scanning Peptide Library Screen

Active full-length human MELK was purified from insect cells. The positional scanning peptide library screen was performed as described in Turk et al. (2006) *Nat. Protocol.* 1:375. Briefly, a set of 180 (or 198) biotin-conjugated peptides with the following sequence, Y-A-X-X-X-X-X-S/T-X-X-X-X-A-G-K-K (SEQ ID NO:42)-biotin, was used. In the sequence, S/T means an equimolar mixture of Ser and Thr. For each peptide, one of the nine X positions represents one of the twenty total amino acids. Peptides were arrayed in a 384-well plates in buffer containing 50 mM HEPES, pH 7.5, 20 mM MgCl2, 0.02 mg/ml BSA, 0.01% Brij 35, 5 mM DTT, 0.5 mM EGTA, and active MELK and γ-[$^{32}$P]ATP was added to wells (final [peptide]=50 µM, and [ATP]=100 µM, 0.025 µCi/µl in each well). After incubating for 2 h at 30° C., aliquots of the reactions were spotted onto a streptavidin membrane. The membrane was quenched, washed extensively, dried, and exposed to a phosphor storage screen.

Figure 1:
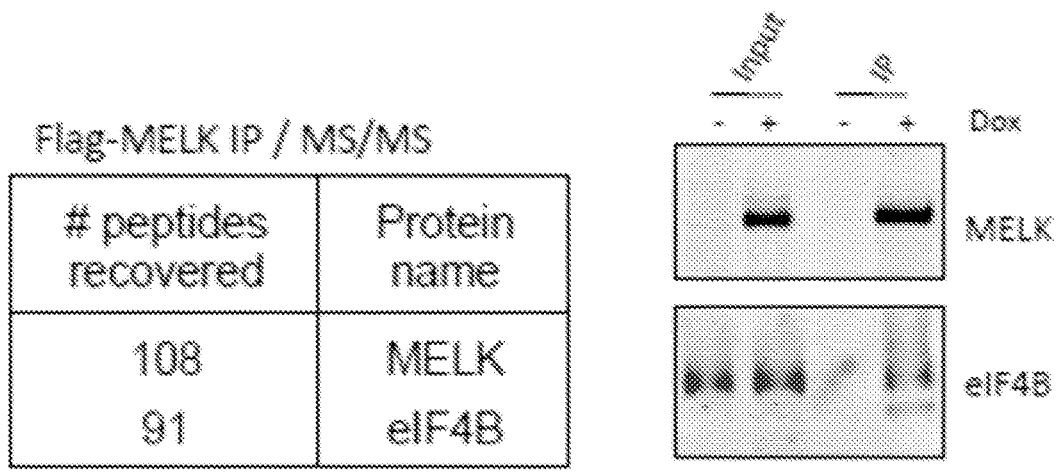
FIG. 1 shows that MELK interacts with eIF4B. Flag-MELK was conditionally expressed in MDA-MB-468 cells. Mitotic lysates were subjected to anti-Flag immunoprecipitation followed by tandem mass spectrometric analysis. The left panel shows the number of peptides recovered from the immunoprecipitates. The right panel shows validation of the interaction between MELK and eIF4B during mitosis. Note that Flag-MELK is doxycycline-inducible.
Figure 2:
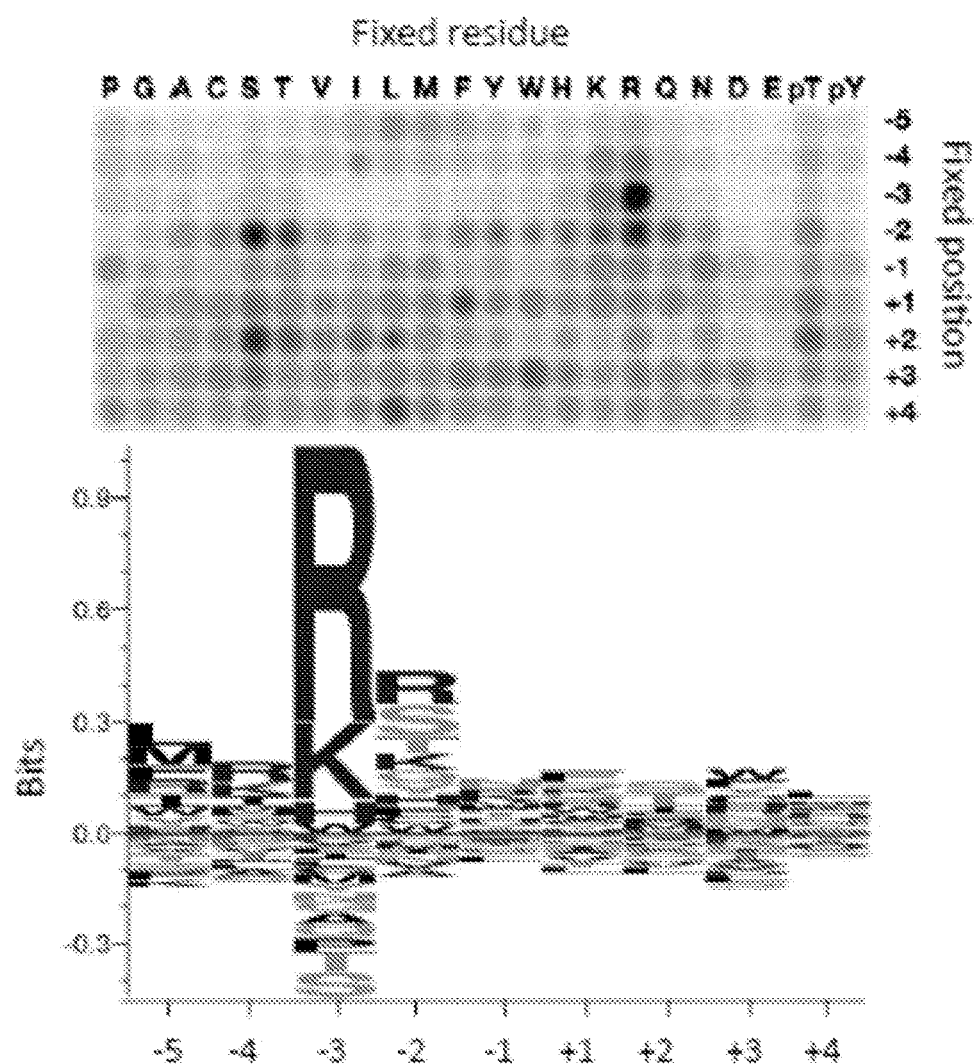
FIG. 2 shows the results of peptide library screening to identify an optimal substrate motif for MELK. The top panel shows the results of a spatially arrayed peptide library subjected to in vitro phosphorylation using recombinant full-length MELK. Each peptide contains one residue fixed at one of nine positions relative to the centrally fixed phosphoacceptor (i.e., serine or threonine). Reactions were spotted onto the membrane and the spots were exposed to a phosphor storage screen. The bottom panel shows a sequence logo generated using quantified and normalized data from the screen. Note that MELK has a strong selection for arginine at the −3 position relative to the phosphoacceptor site.

Example 2: Phosphorylation Status of eIF4B is a Biomarker of MELK Enzymatic and Oncogenic Activity To seek a potential molecular mechanism underlying the importance of MELK for cancer (such as basal-like breast cancer (BBC)), multiple experimental approaches, including immunoprecipitation-tandem mass spectrometry, and phospho-peptide mapping, were explored. When Flag-tagged MELK was immunoprecipitated in mitotic cell lysates and subsequently subject to mass spectrometry analysis, it was found that a translation initiation factor, eIF4B, had a strong association with MELK during mitosis (FIG. 1). Using positional phospho-peptide mapping, an optimal substrate motif for MELK was identified having a strong selection for arginine at the −3 position relative to serine/threonine (FIG. 2).

Figure 3:
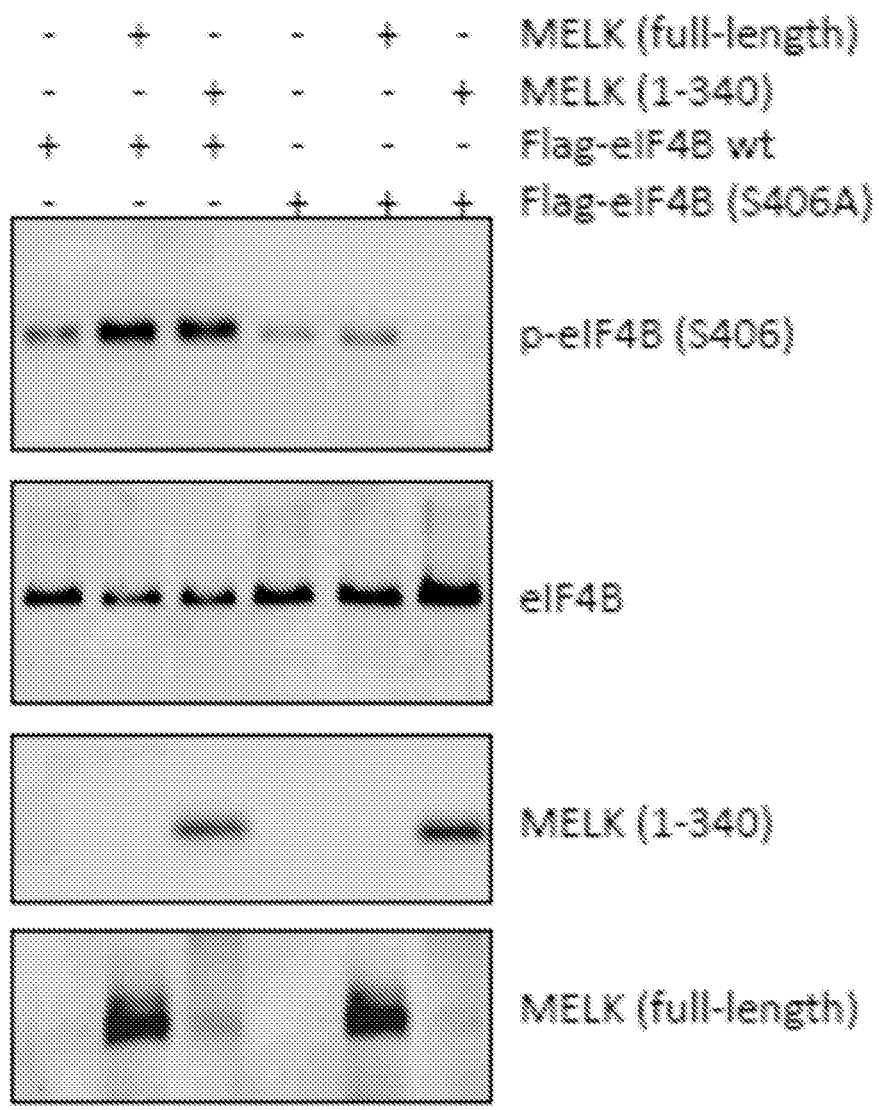
FIG. 3 shows that MELK phosphorylates eIF4B at S406 in vitro. Recombinant full-length MELK or the kinase domain of MELK was subjected to in vitro kinase assays using immunoprecipitated Flag-eIF4B (wild type) or Flag-eIF4B (S406A). Robust phosphorylation of eIF4B at S406 was observed in the presence of MELK. This phosphorylation was abolished when wild type (wt) eIF4B was replaced with a mutant eIF4B (S406A).
Figure 4:
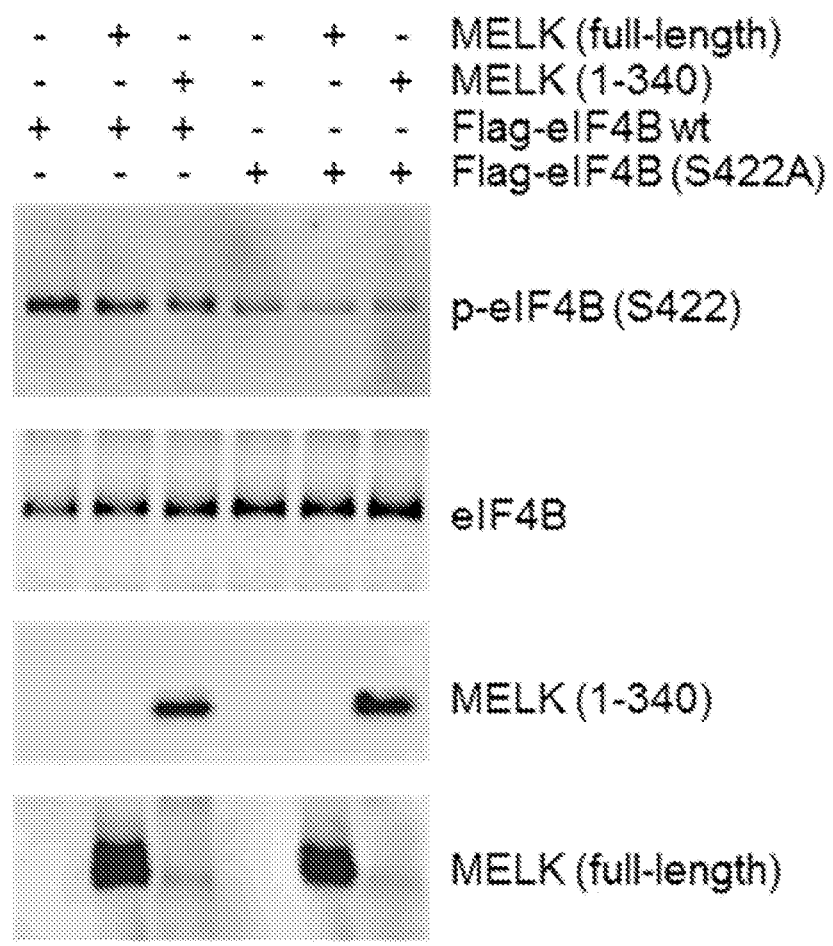
FIG. 4 shows that MELK does not phosphorylates eIF4B at S422 in vitro. Recombinant full-length or kinase domain of MELK was subjected to in vitro kinase assay using immunoprecipitated Flag-eIF4B (wild type) or Flag-eIF4B (S422A). Reactions were analyzed by immunoblotting.
Figure 5:
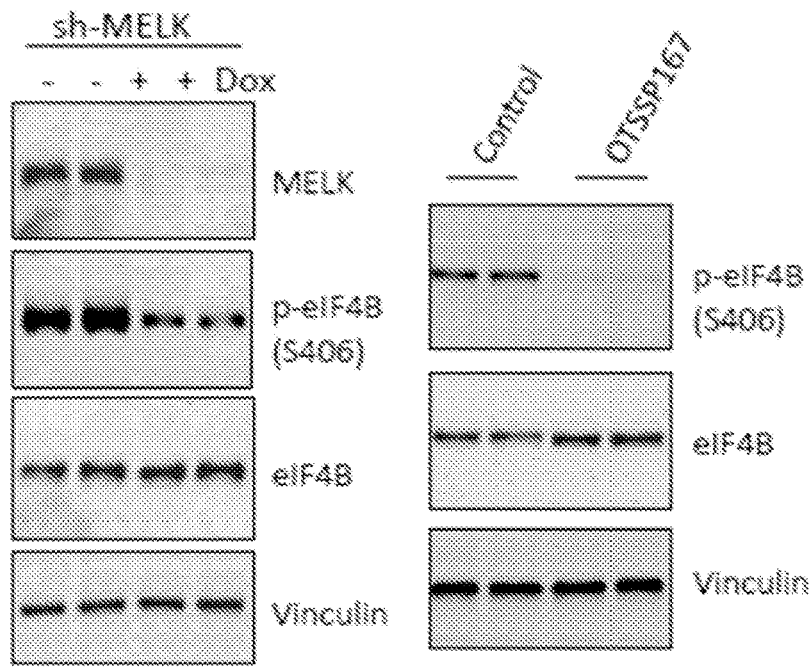
FIG. 5 shows that MELK regulates phosphorylation of eIF4B at S406 in vivo. Left panels show MELK knockdown impairs the phosphorylation of eIF4B at S406. MDA-MB-468 cells stably expressing tetracycline-inducible (tet-on) small hairpin MELK (shMELK) in the presence or absence of doxycycline were harvested through treatment of nocodazole, and subjected to immunoblotting. Right panels show that a MELK inhibitor impairs the phosphorylation of eIF4B at S406. Mitotic MDA-MB-468 cells were treated for 30 min with vehicle or 200 nM OTSSP167, a MELK inhibitor (Chung et al. (2012) *Oncotarget* 3:1629-1640). Lysates were used for immunoblotting.
Figure 6:
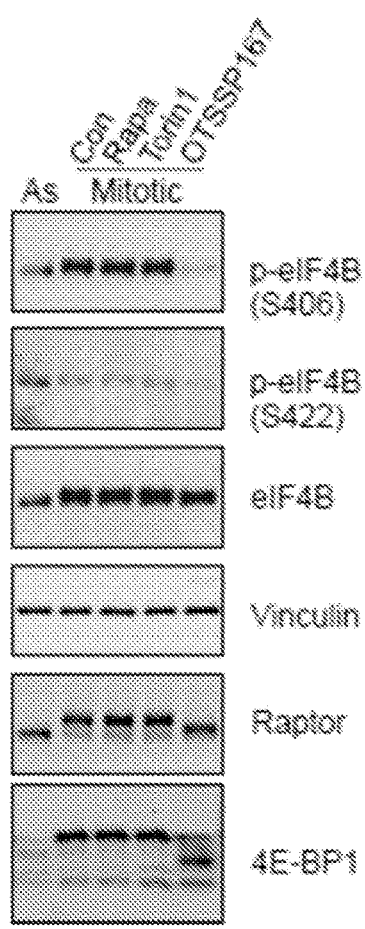
FIG. 6 shows the results of treating mitotic cells for 30 min with mTOR inhibitors (e.g., Rapamycin and Torin 1) versus treating such cells with MELK inhibitors (e.g., OTSSP67). The results indicate that MELK inhibition, but not mTOR inhibition, suppressed the phosphorylation of eIF4B at S406.

There are two regions flanking the residues of human eIF4B at Ser406 and Ser422), which contain the MELK phosphorylation motif (FIGS. 3 and 4). To test whether MELK is capable of phosphorylating human eIF4B at these two sites, in vitro kinase assays were performed using purified recombinant MELK with immunoprecipitated eIF4B. It was found that Ser406, but not Ser422, of human eIF4B was readily phosphorylated by full-length MELK or the kinase domain of MELK, and that the observed phosphorylation was abolished when the serine at 406 of human eIF4B was mutated to alanine or other manipulations of MELK (FIGS. 3-5). These results are specifically dependent upon MELK, as inhibition of mitotic cells with mTOR inhibitors, such as rapamycin and torins, do not produce the same results (FIG. 6; van Gorp et al. (2009) Oncogene 28:95-106). These data indicate that MELK is a kinase that phosphorylates human eIF4B at S406 and that eIF4B orthologs in other species are similarly phosphorylated due to the highly conserved sequence and structural composition of the eIF4B polypeptide region harboring the phosphorylation site (Table 2).

TABLE 2

| eIF 4B S406 | | |
|---|---|---|
| Human | S406 | RERHPSWRSE (SEQ ID NO:43) |
| Chimpanzee | S406 | RERHPSWRSE (SEQ ID NO:43) |
| Monkey | S402 | RERHPSWRSE (SEQ ID NO:43) |
| Cattle | S406 | RERHPSWRSE (SEQ ID NO:43) |
| Dog | S406 | RERHPSWRSE (SEQ ID NO:43) |
| Mouse | S406 | RERHPSWRSE (SEQ ID NO:43) |
| Rat | S406 | RERHPSWRSE (SEQ ID NO:43) |
| Zebrafish | S403 | RERHPSWRSE (SEQ ID NO:43) |
| Fission yeast | S315 | RERSTSRKPS (SEQ ID NO:44) |

Figure 7:
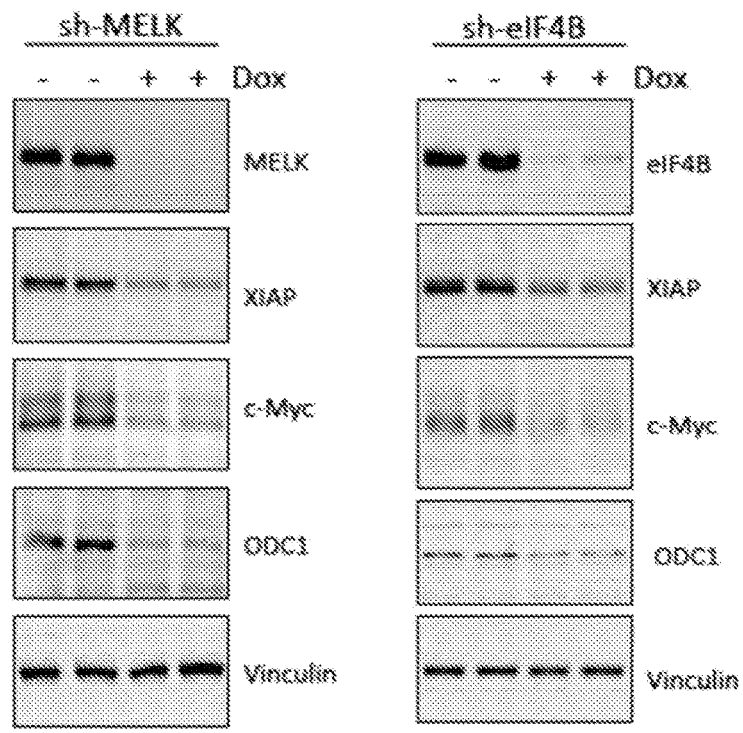
FIG. 7 shows that knocking down MELK or eIF4B decreases the protein abundance of XIAP, c-Myc, and ODC1 during mitosis. MDA-MB-468 and MDA-MB-231 cells stably expressing tet-on shMELK or sh-eIF4B were treated with doxycycline or vehicle control. Mitotic cells were harvested by nocodazole-induced arrest at prometaphase. Note that the mRNA of XIAP, c-Myc, and ODC1 have been shown to contain structured 5'UTR and their total levels remain unchanged.
Figure 8:
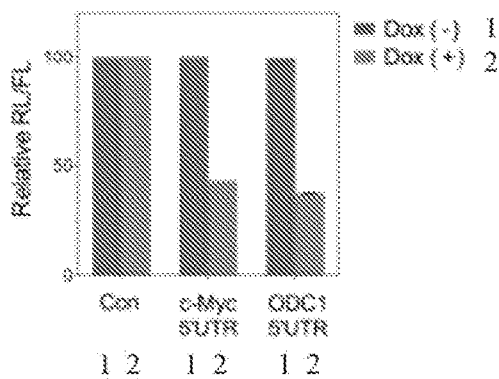
FIG. 8 shows that knocking down MELK decreases the translation of luciferase driven by the 5' UTR of c-Myc or ODC1 during mitosis. MDA-MB-231 cells stably expressing tet-on shMELK were transfected with the indicated bicistronic vector in the presence or absence of doxycycline. Nocodazole-arrested mitotic cells were harvested two days after transfection and subjected to a luciferase assay. The ratio of *Renilla* luciferase to firefly luciferase (RL/FL) was normalized to the value of control vector. Note that the left bar corresponds to Dox (−) and the right bar corresponds to Dox (+) for each pair of bars shown in the graph reporting relative RL/FL ratios.
Figure 8:
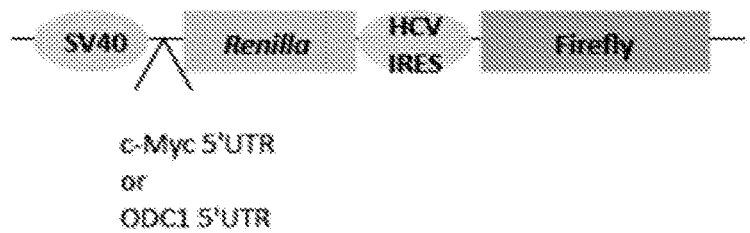

It is known that eIF4B stimulates the helicase activity of eIF4A for unwinding the secondary structure of 5'UTR of mRNA (Dmitriev et al. (2003) Mol. Cell Biol. 23:925-8933 and Shahbazian et al. (2010) Mol. Cell Biol. 30 1478-1485). Many of these mRNAs encode oncogenic proteins, such as c-Myc, XIAP (X-linked inhibitor of apoptosis protein) and ODC (ornithine decarboxylase). It was determined herein that down-regulation of MELK reduced phosphorylation of eIF4B (p-eIF4B) at S406 in MDA-MB-468 cells during mitosis, which also resulted in markedly reduced levels of c-Myc, XIAP and ODC1 (FIGS. 7 and 8). Thus, MELK-mediated S406 phosphorylation of eIF4B during mitosis, is functionally important for the optimal translation of mRNAs with highly structured 5'UTR, many of which are known to be oncogenic, such as c-Myc, XIAP, and ODC1. Together, these data indicate that MELK is a novel kinase that regulates eIF4B during mitosis and thereby mediates the translation of mRNAs that harbor structured 5'-UTR and are important for the survival and proliferation of cancer cells. Thus, the level of eIF4B phosphorylation mediated by MELK is a target engagement biomarker for MELK oncogenic activity useful for preclinical and clinical applications.

Example 3: Phosphorylation Status of Histone H3 is a Biomarker of MELK Enzymatic and Oncogenic Activity Since MELK protein abundance is highest during mitosis, a cell cycle phase when Histon H3 is heavily phosphorylated, a link between MELK and Histone H3 phosphorylation was suggested. In fact, the region flanking the residues of human Histone H3 at Thr-11 contains the optimal MELK phosphorylation motif described in Example 2 above.

Figure 9:
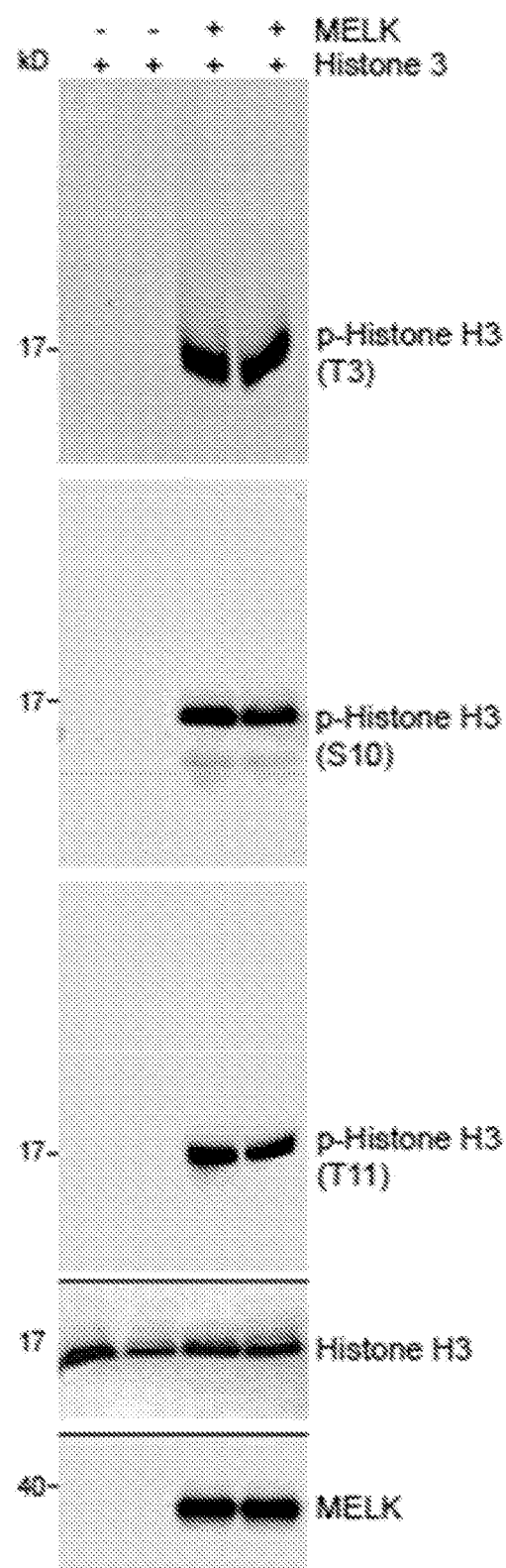
FIG. 9 shows that MELK phosphorylates Histone H3 at Thr-3, Ser-10 and Thr-11 in vitro. Recombinant Histone H3 was incubated with or without recombinant MELK (kinase domain) for 30 min. at 30° C. in the presence of ATP. Reactions were terminated by adding SDS sample buffer. Samples were then subjected to immunoblotting using the indicated antibodies.

To test whether MELK is capable of phosphorylating human Histone H3 at threonine 3 (Thr3), serine 10 (Ser10) and threonine 11 (Thr11), in vitro kinase assays were performed using a purified recombinant kinase domain of human MELK, and human Histone H3. It was found that Thr3, Ser10, and Thr11 of human Histone H3 were readily phosphorylated by the kinase domain of MELK (FIG. 9).

Figure 10:
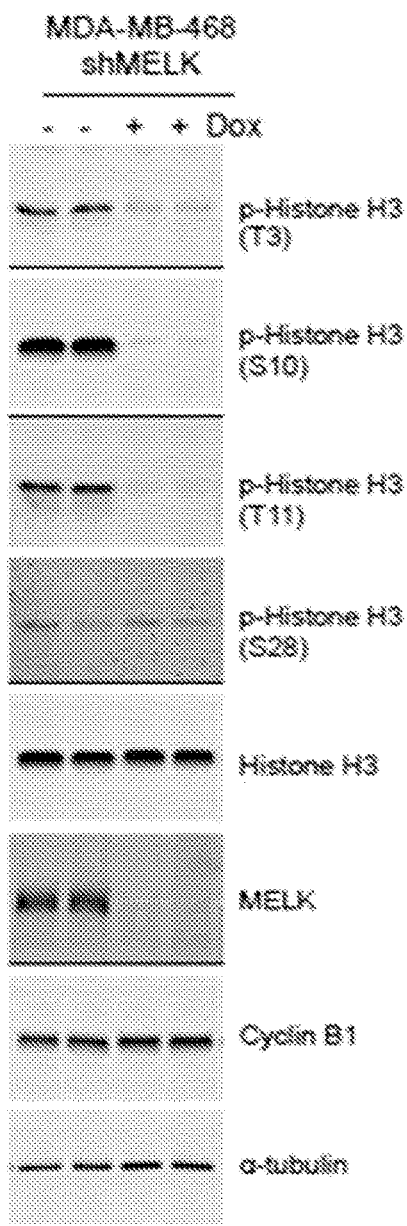
FIG. 10 shows that knocking down MELK decreases the mitotic phosphorylation of Histone H3 at Thr-3, Ser-10 and Thr-11, but not Ser-28. MDA-MB-468 cells stably transduced with tet-on shMELK were untreated or treated with doxycycline (200 ng/ml) in order to induce gene silencing. Cells were then treated with nocodazole (200 ng/ml) for 20 hours. Mitotic cells were harvested by shake-off and cell lysates were subjected to immunoblotting using the indicated antibodies.

Down-regulation of MELK reduced phosphorylation of Histone H3 at Thr3, Ser10 and Thr11 in MDA-MB-468 cells during mitosis, but did not affect the phosphorylation of Aurora kinases A, B, or C, which are known kinases that phosphorylate Histone H3 at Ser10 (FIGS. 10 and 11). Similarly, inhibition of MELK using the small chemical MELK inhibitor, OTSSP167, in MDA-MB-468 cells reduced phosphorylation of Histone H3 at Thr3/Ser10/Thr11 (FIG. 12). An OTSSP167 concentration-dependent reduction in phosphorylation of Histone H3 at Thr3. Ser10 and Thr11, but not Ser28, was also observed (FIG. 13).

These data indicate that MELK is a kinase that phosphorylates human Histone H3 at least at Thr3, Ser10 and Thr11, but not Ser28, and that Histone H3 orthologs in other species are similarly phosphorylated due to the highly conserved sequence and structural composition of the Histone H3 polypeptide region harboring the phosphorylation site (Table 3).

TABLE 3

| Histone H3 | | |
|---|---|---|
| Human | T3/S10/T11 | MARTKQTARKSTGGKA (SEQ ID NO:45) |
| Chimpanzee | T3/S10/T11 | MARTKQTARKSTGGKA (SEQ ID NO:45) |
| Monkey | T3/S10/T11 | MARTKQTARKSTGGKA (SEQ ID NO:45) |
| Cattle | T3/S10/T11 | MARTKQTARKSTGGKA (SEQ ID NO:45) |
| Dog | T3/S10/T11 | MARTKQTARKSTGGKA (SEQ ID NO:45) |
| Moose | T3/S10/T11 | MARTKQTARKSTGGKA (SEQ ID NO:45) |
| Rat | T3/S10/T11 | MARTKQTARKSTGGKA (SEQ ID NO:45) |
| Zebrafish | T3/S10/T11 | MARTKQTARKSTGGKA (SEQ ID NO:45) |
| Fission yeast | T3/S10/T11 | MARTKQTARKSTGGKA (SEQ ID NO:45) |

Together, these data indicate that MELK is a novel kinase that regulates Histone H3 phosphorylation during mitosis and is therefore potentially important for the proliferation of cells (e.g., cancer cells). Thus, the level of Histone H3 phosphorylation mediated by MELK is a target engagement biomarker for MELK oncogenic activity useful for preclinical and clinical applications.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of identifying an agent which inhibits kinase or oncogenic activity of human maternal embryonic leucine zipper kinase (MELK), comprising:
   a) contacting a sample comprising i) human MELK and ii) human eukaryotic initiation factor 4B (eIF4B) or human Histone H3, with the agent; and
   b) determining the ability of the agent to inhibit Ser-406 phosphorylation of human eIF4B, or to inhibit Thr-3 and/or Thr-11 phosphorylation of human Histone H3, wherein decreased phosphorylation identifies an agent which inhibits kinase or oncogenic activity of human MELK.

2. The method of claim 1, wherein the inhibition of said phosphorylation of human eIF4B or Histone H3, is determined by comparing
   i) the amount of phosphorylated human eIF4B or Histone H3 in the sample relative to a control; and/or
   ii) the ratio of the amount of phosphorylated human eIF4B or Histone H3 in the sample relative to the total amount of human eIF4B or Histone H3 to a control.

3. The method of claim 2, wherein the control is
   i) the amount of phosphorylated human eIF4B or Histone H3 in the sample relative to said amount in the absence of the agent or at an earlier timepoint after contact of the sample with the agent; or
   ii) the ratio of the amount of phosphorylated human eIF4B or Histone H3 in the sample relative to said ratio in the absence of the agent or at an earlier timepoint after contact of the sample with the agent.

4. The method of claim 1, further comprising:
   i) determining the amount of a protein translated from an RNA with highly structured 5'UTR, optionally wherein the protein is selected from the group consisting of cellular myelocytomatosis oncogene (c-Myc), X-linked inhibitor of apoptosis protein (XIAP), and ornithine decarboxylase (ODC1);
   ii) determining whether the agent directly binds said human eIF4B or Histone H3, or said human MELK; and/or
   iii) determining the amount of a mitosis-specific protein.

5. The method of claim 1, wherein the sample comprises cells.

6. The method of claim 5, wherein the cells are cancer cells.

7. The method of claim 1, wherein the amount of phosphorylated human eIF4B or Histone H3 is determined by an immunoassay using a reagent which specifically binds to phosphorylated human eIF4B or Histone H3.

8. The method of claim 1, wherein the agent is a small molecule, or an antibody or antigen-binding fragment thereof.

9. The method of claim 1, wherein the human MELK comprises the kinase domain of the amino acid sequence as set forth in SEQ ID NO:2.

10. The method of claim 1, wherein the human MELK comprises an amino acid sequence selected from the group consisting of sequences set forth in SEQ ID NOs: 2, 4, 6, 8, 10, 12, 14, 16, 18, and 20.

11. The method of claim 1, wherein the human MELK comprises the amino acid sequence as set forth in SEQ ID NO:2.

12. The method of claim 1, wherein the sample is selected from the group consisting of in vitro, ex vivo, and in vivo samples.

13. The method of claim 1, wherein the sample is selected from the group consisting of tissue, whole blood, serum, plasma, buccal scrape, saliva, cerebrospinal fluid, urine, stool, and bone marrow.

14. The method of claim 5, wherein the cells are obtained from a subject.

15. The method of claim 6, wherein the cancer is selected from the group consisting of any cancer in which MELK or eIF4B or Histone H3 is amplified or overexpressed, any cancer having an activating mutation of MELK or eIF4B or Histone H3, and any cancer in which MELK or eIF4B or Histone H3 is activated by other kinases.

16. The method of claim 7, wherein the immunoassay is a radioimmunoassay, a Western blot assay, a proximity ligation assay, an immunofluorescence assay, an enzyme immunoassay, an immunoprecipitation assay, a chemiluminescence assay, an immunohistochemical assay, a dot blot assay, or a slot blot assay.

17. The method of claim 16, wherein the enzyme immunoassay is a sandwich enzyme immunoassay using a capture antibody or fragment thereof which specifically binds with human eIF4B or Histone H3, and a detection antibody or fragment thereof which specifically binds with Ser-406 phosphorylated human eIF4B or Thr-3 and/or Thr-11 phosphorylated human Histone H3.

18. The method of claim 1, wherein the agent decreases the amount of phosphorylated human eIF4B or Histone H3 by at least 50%.

* * * * *